US005576500A

United States Patent [19]
Cage et al.

[11] Patent Number: 5,576,500
[45] Date of Patent: Nov. 19, 1996

[54] CORIOLIS MASS FLOW RATE METER HAVING MEANS FOR MODIFYING ANGULAR VELOCITY GRADIENT POSITIONED WITHIN A CONDUIT

[75] Inventors: Donald R. Cage; Steven W. Campbell; David T. Hahn, all of Longmont, Colo.

[73] Assignee: Direct Measurement Corporation, Longmont, Colo.

[21] Appl. No.: 419,360

[22] Filed: Apr. 10, 1995

Related U.S. Application Data

[62] Division of Ser. No. 326,751, Oct. 20, 1994, Pat. No. 5,448,921, and a continuation of Ser. No. 83,975, Jun. 28, 1993, abandoned, and a continuation-in-part of Ser. No. 167,719, Dec. 15, 1993, Pat. No. 5,373,745, and a continuation of Ser. No. 843,519, May 8, 1992, abandoned, and a continuation-in-part of Ser. No. 651,301, Feb. 5, 1991, abandoned.

[51] Int. Cl.$^6$ ....................................................... G01F 1/84
[52] U.S. Cl. .............................. 73/861.357; 73/861.355
[58] Field of Search ........................ 73/861.351, 861.352, 73/861.353, 861.354, 861.355, 861.356, 861.357

[56] References Cited

U.S. PATENT DOCUMENTS

| | | | |
|---|---|---|---|
| Re. 31,450 | 11/1983 | Smith | 73/861.38 |
| 3,444,723 | 5/1969 | Wakefield | 73/32 |
| 3,485,098 | 12/1969 | Sipin | 73/194 |
| 3,927,565 | 12/1975 | Pavlin et al. | 73/194 |
| 4,009,616 | 3/1977 | Wonn | 73/398 R |
| 4,109,524 | 8/1978 | Smith | 73/194 |
| 4,420,983 | 12/1983 | Langdon | 73/861.18 |
| 4,422,338 | 12/1983 | Smith | 73/861.38 |
| 4,490,009 | 12/1984 | Nakai et al. | 350/96.23 |
| 4,491,025 | 1/1985 | Smith et al. | 73/861.38 |

(List continued on next page.)

FOREIGN PATENT DOCUMENTS

| | | |
|---|---|---|
| 30109218 | 5/1984 | European Pat. Off. . |
| 40119638 | 9/1984 | European Pat. Off. . |
| 0210308 | 2/1987 | European Pat. Off. . |
| 0261435 | 3/1988 | European Pat. Off. . |
| 0272758 | 6/1988 | European Pat. Off. . |
| 0316908 | 5/1989 | European Pat. Off. . |
| 0375300 | 6/1990 | European Pat. Off. . |
| 2598801 | 11/1987 | France . |
| 3505166C2 | 8/1987 | Germany . |
| 8814606 U | 9/1989 | Germany . |
| 57-137818 | 8/1982 | Japan . |
| 62-180741 | 8/1987 | Japan . |
| 1008-617-A | 2/1980 | Sudan . |
| 2171200 | 8/1986 | United Kingdom . |
| WO85/05677 | 12/1985 | WIPO . |
| WO87/06691 | 11/1987 | WIPO . |

OTHER PUBLICATIONS

Publication entitled "Direkte Massedurchflussmessung, Insbesonderemit Coriolisverfahren" by Von W. Steffen und Dr. W. Stumm; Part II; pp. 301–305; Published in Messen Prüfen Automatisieren vol. 23 (1987) May, No. 5, pp. 301–305; Bad Wörishofen, W. Germany.

*Primary Examiner*—Richard Chilcot
*Assistant Examiner*—Harshad Patel
*Attorney, Agent, or Firm*—Hitt Chwang & Gaines, P.C.

[57] ABSTRACT

A flow meter apparatus for measuring attributes of a fluid using the Coriolis principle is disclosed. The apparatus comprises (1) a body capable of being inserted into and surrounded by the fluid, (2) an actuator, disposed within the body, for vibrating a surface of the body in a radial mode of vibration, the vibrating surface developing Coriolis forces within the fluid, (3) a detector, coupled to the surface, for measuring motion of the surface, the motion being a function of Coriolis forces developed in the fluid and (4) a circuit, coupled to the measuring detector, for determining an attribute of the fluid as a function of the motion of the surface. In a preferred embodiment of the invention, a conduit surrounds the apparatus and is coupled to the detector. The apparatus allows precise detection of mass flow rate, pressure, density and viscosity of the fluid surrounding the apparatus.

24 Claims, 37 Drawing Sheets

U.S. PATENT DOCUMENTS

| | | | |
|---|---|---|---|
| 4,574,639 | 3/1986 | Ward | 73/702 |
| 4,622,858 | 11/1986 | Mizerak | 73/861.38 |
| 4,628,744 | 12/1986 | Lew | 73/861.38 |
| 4,653,332 | 3/1987 | Simonsen | 73/861.38 |
| 4,680,974 | 7/1987 | Simonsen et al. | 73/861.38 |
| 4,691,578 | 9/1987 | Herzl | 73/861.38 |
| 4,711,132 | 12/1987 | Dahlin | 73/861.38 |
| 4,716,771 | 1/1988 | Kane | 73/861.38 |
| 4,729,243 | 3/1988 | Friedland et al. | 73/861.38 |
| 4,733,569 | 3/1988 | Kelsey et al. | 73/861.38 |
| 4,756,197 | 7/1988 | Herzl | 73/861.38 |
| 4,768,384 | 9/1988 | Flecken et al. | 73/861.02 |
| 4,776,220 | 10/1988 | Lew | 73/861.38 |
| 4,793,191 | 12/1988 | Flecken et al. | 73/861.38 |
| 4,798,091 | 1/1989 | Lew | 73/861.38 |
| 4,803,867 | 2/1989 | Dahlin | 73/32 |
| 4,811,606 | 3/1989 | Hasegawa et al. | 73/861.38 |
| 4,813,289 | 3/1989 | Lew | 73/861.38 |
| 4,823,614 | 4/1989 | Lew | 73/861.38 |
| 4,829,832 | 5/1989 | Lew | 73/861.38 |
| 4,831,885 | 5/1989 | Dahlin | 73/861.38 |
| 4,852,410 | 8/1989 | Corwon et al. | 73/861.38 |
| 4,856,346 | 8/1989 | Kane | 73/861.38 |
| 4,869,097 | 9/1989 | Tittmann et al. | 73/52 |
| 4,879,910 | 11/1989 | Lew | 73/861.37 |
| 4,882,935 | 11/1989 | Lew | 73/861.38 |
| 4,891,991 | 1/1990 | Mattar et al. | 73/861.38 |
| 4,934,195 | 6/1990 | Hussain | 73/861.38 |
| 4,949,583 | 8/1990 | Lang et al. | 73/861.37 |
| 5,024,104 | 6/1991 | Dames | 73/861.37 |
| 5,040,415 | 8/1991 | Barkhoudarian | 73/198 |
| 5,044,207 | 9/1991 | Atkinson et al. | 73/861.37 |
| 5,069,075 | 12/1991 | Hansen et al. | 73/861.38 |
| 5,226,330 | 7/1993 | Lew | 73/861.38 |
| 5,230,254 | 7/1993 | Craft | 73/861.38 |
| 5,373,745 | 12/1994 | Cage | 73/861.37 |
| 5,448,921 | 9/1995 | Cage et al. | 73/861.357 |

CORIOLIS MASS FLOW RATE METER HAVING MEANS FOR MODIFYING ANGULAR VELOCITY GRADIENT POSITIONED WITHIN A CONDUIT

CROSS REFERENCE TO RELATED APPLICATIONS

This is a divisional of application Ser. No. 08/326,751, filed on Oct. 20, 1994 now U.S. Pat. No. 5,448,921, a continuation of application Ser. No. 08/083,975, filed on Jun. 28, 1993 now abandoned, a continuation-in-part of application Ser. No. 08/167,719, filed on Dec. 15, 1993 now U.S. Pat. No. 5,373,745, a continuation of application Ser. No. 07/843,519, filed on May 8, 1992 now abandoned, a continuation-in-part of application Ser. No. 07/651,301, filed on Feb. 5, 1991 now abandoned, all of which are commonly assigned with the present invention and are incorporated herein by reference.

TECHNICAL FIELD OF THE INVENTION

This invention relates to Coriolis mass flow rate meters and, in particular, to Coriolis mass flow rate meters that are insertable in a single straight flow conduit to measure mass flow rate.

BACKGROUND OF THE INVENTION

In the art of Coriolis mass flow rate meters it is well known that a vibrating flow conduit carrying mass flow causes Coriolis forces which deflect the flow conduit away from its normal vibration path proportionally related to mass flow rate. These deflections or their effects can then be measured as an accurate indication of mass flow rate.

This effect was first made commercially successful by Micro Motion Inc. of Boulder Colorado. Early designs employed a single vibrating U-shaped flow conduit which was cantilever mounted from a base. With nothing to counter-balance the vibration of the flow conduit, the design was highly sensitive to mounting conditions and so was redesigned to employ another mounted vibrating arrangement which acted as a counter-balance for the flow conduit similar to that disclosed in their U.S. Pat. Nos. RE-31,450 and 4,422,338 to Smith. Problems occurred however since changes in the specific gravity of the process-fluid were not matched by changes on the counter-balance, an unbalanced condition could result causing errors. Significant improvement was later made by replacing the counter-balance arrangement by another U-shaped flow conduit identical to the first and splitting the flow into parallel paths, flowing through both conduits simultaneously. This parallel path Coriolis mass flow rate meter (U.S. Pat. No. 4,491,025 to Smith et al.) solves this balance problem and has thus become the premier method of mass flow measurement in industry today.

Many other flow conduit geometries have been invented which offer various performance enhancements or alternatives. Examples of different flow conduit geometries are the dual S-tubes of U.S. Pat. Nos. 4,798,091 and 4,776,220 to Lew, the omega shaped tubes of U.S. Pat. No. 4,852,410 to Corwon et al., the B-shapes tubes of U.S. Pat. No. 4,891,991 to Mattar et al., the helically wound flow conduits of U.S. Pat. No. 4,756,198 to Levien, figure-8 shaped flow conduits of U.S. Pat. No. 4,716,771 to Kane, the dual straight tubes of U.S. Pat. No. 4,680,974 to Simonsen et al. and others. All of these geometries employ the basic concept of two parallel flow conduits vibrating in opposition to one another to create a balanced resonant vibrating system.

Although the parallel path Coriolis mass flow rate meter has been a tremendous commercial success, several problems remain. Most of these problems are a consequence of using flow splitters and two parallel flow conduits in order to maintain a balanced resonant system. In addition, most designs employ flow conduits that are curved into various shapes as previously described to enhance the sensitivity of the device to mass flow rate. These two common design features cause a number of problems which preclude the use of Coriolis technology in many applications that would benefit from its use.

Among the problems caused by the flow splitters and curved flow conduits are: (1) excessive fluid pressure-drop caused by turbulence and drag forces as the fluid passes through the flow splitters and curves of the device, (2) difficulty in lining or plating the inner surface of geometries having flow splitters and curved flow conduits, with corrosive resistant materials, (3) inability to meet food and pharmaceutical industry sanitary requirements such as polished surface finish, non-plugable, self-draining, and visually inspectable, (4) difficulty in designing a case to surround dual curved flow conduits which can contain high rated pressures, (5) difficulty in designing flow meters for 6" diameter and larger pipelines and (6) difficulty in reducing the cost of current designs due to the added value of flow splitters, dual flow conduits and curved flow conduit fabrication.

It is therefore recognized that a Coriolis mass flow rate meter employing a single straight flow conduit would be a tremendous advancement in the art.

Ser. No. 07/651,301, filed on Feb. 5, 1991, and entitled "Single Path Radial Mode Coriolis Mass Flow Meter," is directed to a meter employing a single straight flow conduit designed to be vibrated in a radial mode to thereby provide a means by which to measure mass flow rate of fluids within the conduit. Ser. No. 07/843,519, filed on May 8, 1992, entitled "Improved Coriolis Mass Flow Meter" and a continuation-in-part of Ser. No. 07/651,301 is directed, inter alia, to a mass flow meter capable of measuring pressure and viscosity of the fluid within the conduit and to an alternative construction of a mass flow meter employing a vibrating surface on an otherwise rigid conduit to measure mass flow and other fluid attributes.

What is still needed in the art is a torpedo-type device that is insertable into a conduit to allow measurement of mass flow and other attributes of a fluid within the conduit.

SUMMARY OF THE INVENTION

According to the object of the present invention, an apparatus for measuring attributes of a fluid taking advantage of the Coriolis principle is provided. The apparatus comprises: (1) a body capable of being inserted into and surrounded by the fluid, (2) means (in a preferred embodiment, an actuator), disposed within the body, for vibrating a surface of the body in a radial mode of vibration, the vibrating surface developing Coriolis forces within the fluid, (3) means (in a preferred embodiment, a detector), coupled to the surface, for measuring motion of the surface, the motion being a function of Coriolis forces developed in the fluid and (4) means (in a preferred embodiment, a circuit), coupled to the measuring means, for determining an attribute of the fluid as a function of the motion of the surface.

A further object of the present invention is to provide an apparatus wherein the vibrating means vibrates the surface in two radial modes of vibration.

A further object of the present invention is to provide an apparatus wherein the measuring means measures a change in phase of the motion of the surface.

A further object of the present invention is to provide an apparatus wherein the measuring means measures a change in amplitude of the motion of the surface.

A further object of the present invention is to provide an apparatus wherein the body is elongated and the fluid flows along a longitudinal axis of the body.

A further object of the present invention is to provide an apparatus wherein the body is elongated and the fluid flows along a transverse axis of the body.

A further object of the present invention is to provide an apparatus wherein the apparatus is disposed within a conduit, the fluid is capable of being disposed between the apparatus and the conduit and the means for measuring is coupled to the conduit.

A further object of the present invention is to provide an apparatus further comprising means for vibrating the conduit.

A further object of the present invention is to provide an apparatus further comprising means for sensing a change in motion of the conduit.

A further object of the present invention is to provide an apparatus wherein the attribute is any one or more of the following attributes: a mass flow rate, a pressure, a density and a viscosity of the fluid. Throughout the following discussion, reference is made to a meter for measuring mass flow. Those ordinarily skilled in the art should understand that pressure, density, viscosity or other attributes of the fluid are readily ascertainable by the same structure and function and that ascertainment of these other attributes is within the scope of the present invention.

The apparatus herein uses a single straight flow conduit and a unique vibration method, thereby eliminating the problems caused by flow splitters and curved flow conduits while retaining the current advantages of balance and symmetry.

The basic operation of a commercially available Coriolis mass flow rate meter according to current art will now be described. Normally two process-fluid filled flow conduits are employed in a parallel-path or serial-path configuration. The two flow conduits form a balanced resonant system and as such are forced to vibrate in a prescribed oscillatory bending-mode of vibration. If the process-fluid is flowing, the combination of fluid motion and conduit vibration causes Coriolis forces which deflect the conduits away from their normal (no flow) paths of vibration proportionally related to mass flow rate. These deflections, or their effects, are then measured as an accurate indication of mass flow rate.

As previously described, only one flow conduit is necessary for measuring mass flow rate in this manner. However, to achieve the superior performance afforded by a balanced resonant system, it is necessary to counter-balance the reaction forces from the forced vibration, thus a second flow conduit is normally employed. For very small meter designs the mass and stiffness properties of the mounting conditions can be sufficiently great to counteract the reaction forces from the forced vibration thereby allowing the use of only one flow conduit. Accordingly, Micro Motion Inc. presently offers only their two smallest flow meters, the model D6 (1/16" line size) and the model D12 (1/8" line size) in a single curved flow conduit configuration.

A single straight flow conduit while solving the aforementioned problems caused by flow splitters and curved conduits, has therefore not been commercially successful in Coriolis mass flow rate meter designs, especially for large flow conduits. This failure is due to the inherent imbalance of a single straight flow conduit in any natural bending-modes of vibration. A straight flow conduit fixedly mounted at both ends has a number of natural bending-modes of vibration wherein the center-line of the conduit deflects or rotates away from its rest position in a number of half sine-shaped waves along the length of the conduit. Higher frequency bending-modes involve increasing numbers of these half sine-shaped waves in integer multiples. Each of these bending-modes causes reaction forces applied to the conduit mounts creating balance and accuracy problems analogous to the single curved flow conduit models previously described. A single straight tube design of this nature is disclosed in U.S. Pat. No. 4,823,614 to Dahlin, in which the flow tube cross-section is permanently deformed in several locations as shown in its FIGS. 2A–2D to enhance its bending in a "higher-mode" such as its FIG. 3B. The higher modes of vibration as shown in the Dahlin patent FIGS. 3A–3E all show the flow conduit bending away from a straight line at its ends which will cause reaction torques and forces at the mounts. These reactions are not counter-balanced and thus can create reaction forces as previously described. Dahlin states that this embodiment can be used in "average" sized pipes with average being defined as ½ to ¾ inch inside diameter. Although the reason for this size restriction is not explained, it is probably a consequence of imbalance from using a bending-mode of vibration with no counter-balance apparatus.

The unique advantages of the present invention accrue from the use of a single straight flow conduit in a radial-mode of vibration instead of a bending-mode as is currently used in the art. For clarity, the term "bending-mode" is defined as a vibration mode wherein the center-line or axis of the flow conduit translates and/or rotates away from its rest position in an oscillatory manner while the cross-sectional shape of the flow conduit remains essentially unchanged. By contrast, the term "radial-mode" is defined as a vibration mode wherein the center-line or axis of the flow conduit remains essentially unchanged while all or a part of the wall of the flow conduit translates and/or rotates away from its rest position in an oscillatory manner. Common examples of radial-modes of vibration are the natural vibration of a bell or wine glass. In these two examples the fundamental radial-mode of vibration causes the normally round cross-sectional shape of the free end of the bell or wine glass to deflect into an oscillating elliptical shape. Since the center-line or axis of this radial-mode stays essentially unchanged, the stem (in the wine glass example) can be held without feeling or interfering with the vibration, exemplifying the absence of reaction forces at the mount. Applying this idea to the flow conduit of a Coriolis mass flow rate meter, a single straight flow conduit is employed, fixedly attached at both ends, and vibrated in a radial-mode of vibration where the wall of the flow conduit translates and/or rotates away from its rest position in an oscillatory manner, and the center-line of the flow conduit remains essentially unchanged. The combination of fluid motion and radial-mode vibration causes a Coriolis force distribution along the moving wall of the flow conduit which alters the cross-sectional shape of the conduit as a function of mass flow rate. This altered shape or its effects, are then measured as an accurate indication of mass flow rate. Since this radial mode of vibration causes substantially no net reaction forces where the conduits are mounted, a balanced resonant system Coriolis mass flow rate meter is thereby created with no flow splitters, curved flow conduits, or counter-balance devices.

In addition, a unique non-intrusive method is employed to determine the pressure and the density of the fluid inside the flow conduit by simultaneously vibrating the flow conduit in two modes of vibration. The values of the frequencies of the two modes of vibration are functionally related to both the fluid density and the pressure difference between the inside and the outside of the flow conduit.

Due to the unique operation of the invention, and its ability to directly measure mass flow rate, fluid density, temperature and pressure, virtually any defined static or dynamic fluid parameter can be calculated such as fluid state, viscosity, quality, compressibility, energy flow rate, net flow rate, etc.

As an alternate to using a radial-mode of vibration involving the entire wall of the flow conduit as previously described, a portion of the flow conduit perimeter can be vibrated as necessary to generate Coriolis forces. This method is well suited for use in flow conduits of very large size and non-circular shapes where vibration of the entire conduit is not practical. This method is also well suited to flow conduits formed into bulk materials thus having several rigid sides incapable of entire-perimeter radial mode vibration, such as a flow conduit etched into silicon or quartz to form a micro flow meter.

The present invention solves the previously mentioned problems caused by flow splitters, curved flow conduits and imbalance and allows Coriolis mass flow meter technology to be used in areas such as sanitary applications, gas flow, air flow meters for weather stations, airplanes, low pressure air-duct systems, micro flow meters, liquid flow meters for residential, industrial, oceanographic and shipboard use, and many more.

A preferred embodiment of the present invention is a system for processing fluids comprising: (1) an apparatus for measuring an attribute of a fluid in a flow conduit comprising: (1a) an elongated body capable of being inserted into and surrounded by the fluid, (1b) means, disposed within the body, for vibrating a surface of the body in a radial mode of vibration, the vibrating surface developing Coriolis forces within the fluid, (1c) means, coupled to the surface, for measuring motion of the surface, the motion being a function of Coriolis forces developed in the fluid and (1d) means, coupled to the measuring means, for determining an attribute of the fluid as a function of the motion of the surface, (2) a conduit surrounding the apparatus, the fluid capable of being disposed between the apparatus and the conduit and the means for measuring coupled to the conduit and (3) means for vibrating the conduit to thereby allow the system to measure the attribute, the attribute being selected from the group consisting of: (3a) mass flow rate, (3b) pressure, (3c) density and (3d) viscosity of the fluid.

The foregoing has outlined rather broadly the features and technical advantages of the present invention in order that the detailed description of the invention that follows may be better understood. Additional features and advantages of the invention will be described hereinafter which form the subject of the claims of the invention. Those skilled in the art should appreciate that the conception and the specific embodiment disclosed may be readily utilized as a basis for modifying or designing other structures for carrying out the same purposes of the present invention. Those skilled in the art should also realize that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

Figure 1:
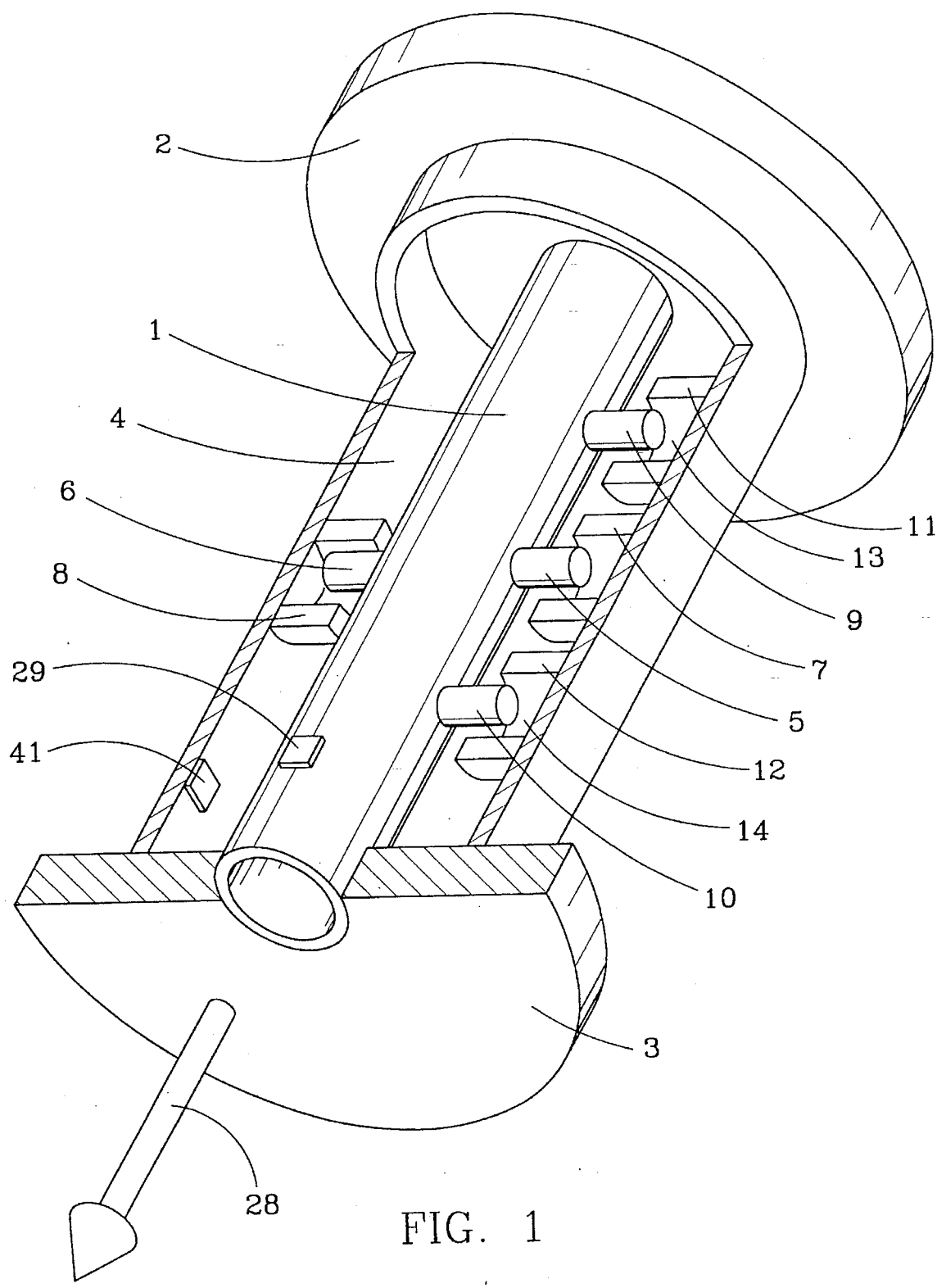
FIG. 1 is a perspective view of one possible preferred exemplary embodiment of the present invention with a portion of the outer case cut away for viewing the apparatus inside.

FIG. 1 shows a perspective view of one preferred exemplary embodiment of the present invention as disclosed in Ser. No. 07/651,301. This embodiment comprises a single straight flow conduit 1 preferably made of a strong flexible non-corrosive material such as titanium. Alternate materials with properties that enhance performance characteristics such as flexibility, corrosion resistance, fatigue strength, constant elastic modulus, low expansion rate, and others can also be used. These alternate materials include 300 series stainless steels, Inconel, Nispan-C and Monel by International Nickel Company, alloys of Hasteloy by the Cabot Corporation, aluminum, beryllium-copper, latex rubber, fiberglass, acrylic, quartz and others. In addition, the inner surface of conduit 1 can be subsequently lined or plated with a non-corrosive material such as nickel, gold, zirconium, fluoropolymers such as Teflon by Dupont, and others.

Flow conduit 1 is fixedly attached at its ends to manifolds 2 and 3, preferably by a welding or brazing process. It is anticipated that manifolds 2 and 3 can be designed in a variety of configurations such as standard pipe flanges, threaded pipe fittings, sanitary fittings, quick-connect fittings, extended tubes, hydrodynamically or aerodynamically shaped openings, and others. It is further anticipated that manifolds will normally be used for convenience of mounting the device or its parts, however manifolds are not necessary for the operation of the device. Accordingly, a portion of an existing pipeline could be instrumented and vibrated in a radial-mode vibration to create the requisite Coriolis forces without the aid of manifolds, however, since existing pipelines can have inappropriate geometric and material properties for this service, it is not the preferred method.

Mounted in association with flow conduit 1 is temperature sensor 29 which is preferably a platinum resistance thermal device (RTD), however many other types of temperature sensors could be used such as thermocouples, semiconductor sensors, optical and others. If a flow conduit material is used with an elastic modulus that changes as a function of temperature, the sensitivity of the device to mass flow rate can also change related to temperature. This effect can be negated by compensating the final flow rate output signal (19 of FIG. 16) functionally related to the temperature of flow conduit 1.

Concentrically arranged around flow conduit 1 is case 4, preferably made of a strong low-corrosion material such as 300 series stainless steel pipe. Some of the possible design considerations of case 4 are to protect conduit 1 and its components from ambient conditions, to contain process fluid in case of a leak, to minimize the effect of stresses on conduit 1 caused by mounting conditions, to contain a prescribed amount of pressure to extend the pressure range or alter the sensitivity of flow conduit 1 to mass flow rate, to convey purging gas to the components inside, to contain a vacuum around conduit 1, for mounting the motion drivers and sensors, and others. A wide variety of possible case materials and configurations are thus anticipated depending on desired performance characteristics. Some alternate materials for case 4 include alloy, or carbon steel, aluminum, brass, quartz, glass, plastic and others. Case 4 is fixedly attached at its ends to manifolds 2 and 3 preferably by a welding or brazing process thus forming a simple protective vessel surrounding the flow conduit. It is anticipated that a case will normally be used, however, it is not necessary for the operation of the device.

A temperature difference between conduit 1 and case 4 can cause a thermally induced expansion difference which can create axial stress in conduit 1. This axial stress can alter the sensitivity of conduit 1 to mass flow rate.

Figure 24:
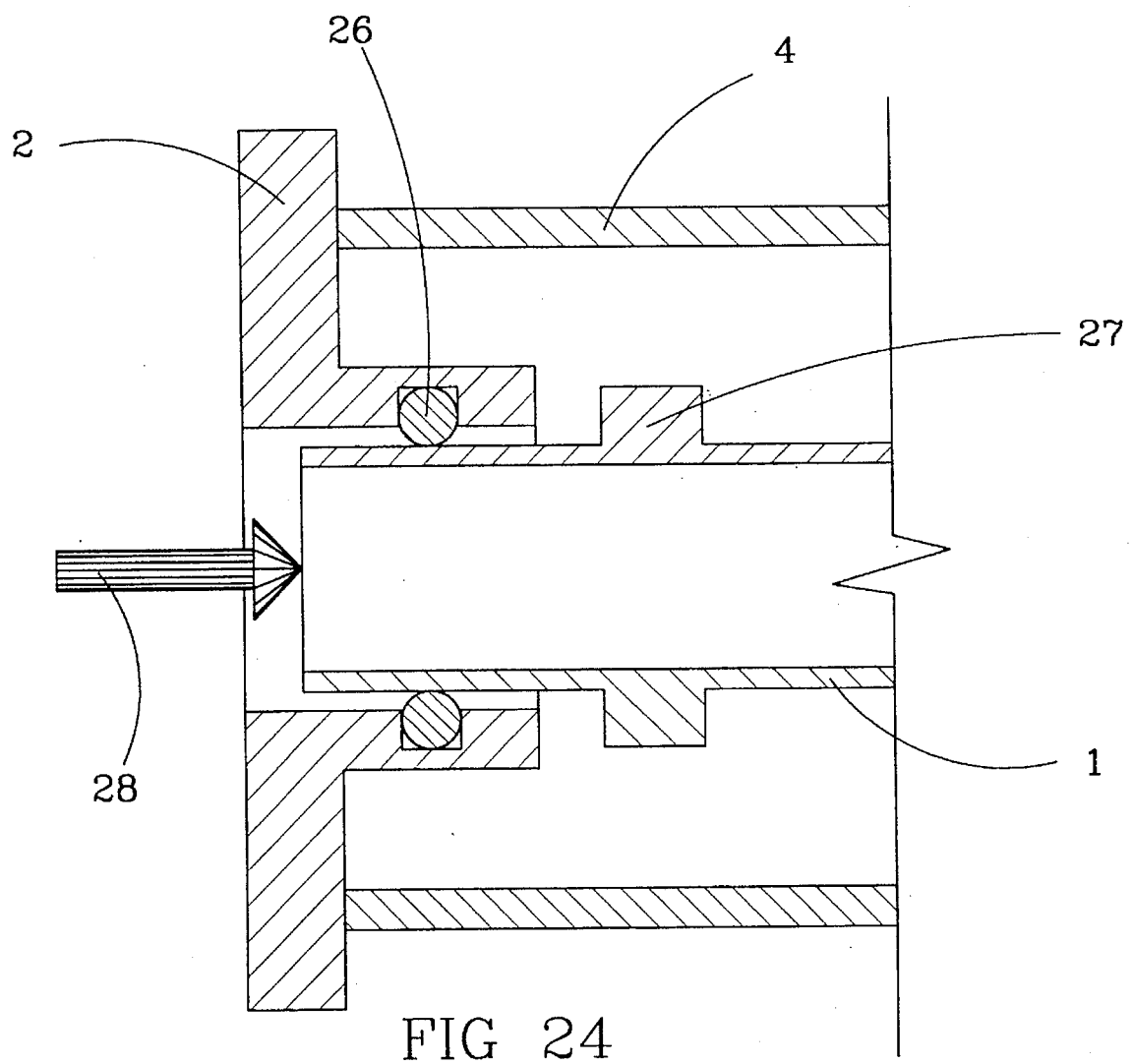
FIG. 24 is a cross-sectional view of an exemplary stress decoupling joint used to eliminate axial stress from the flow conduit.

This effect as well as mounting induced axial stress effects can be negated by mounting at least one end of conduit 1 to a slip-joint or flexible joint incapable of bearing axial stress such as shown in FIG. 24 where conduit 1 is slipped through an O-ring seal 26 in manifold 2 and therefore pipe-line stress is transmitted around conduit 1 through manifold 2 and case 4. In this arrangement, a stiffener 27 would preferably be used to isolate the radial vibration of conduit 1 along a selected portion of conduit 1 and away from the slip-joint area. Stiffener 27 could also be used for this vibration isolation purpose without being associated with a slip-joint or flexible joint, to effectively isolate the radial vibration along a selected portion of the flow conduit.

Figure 25:
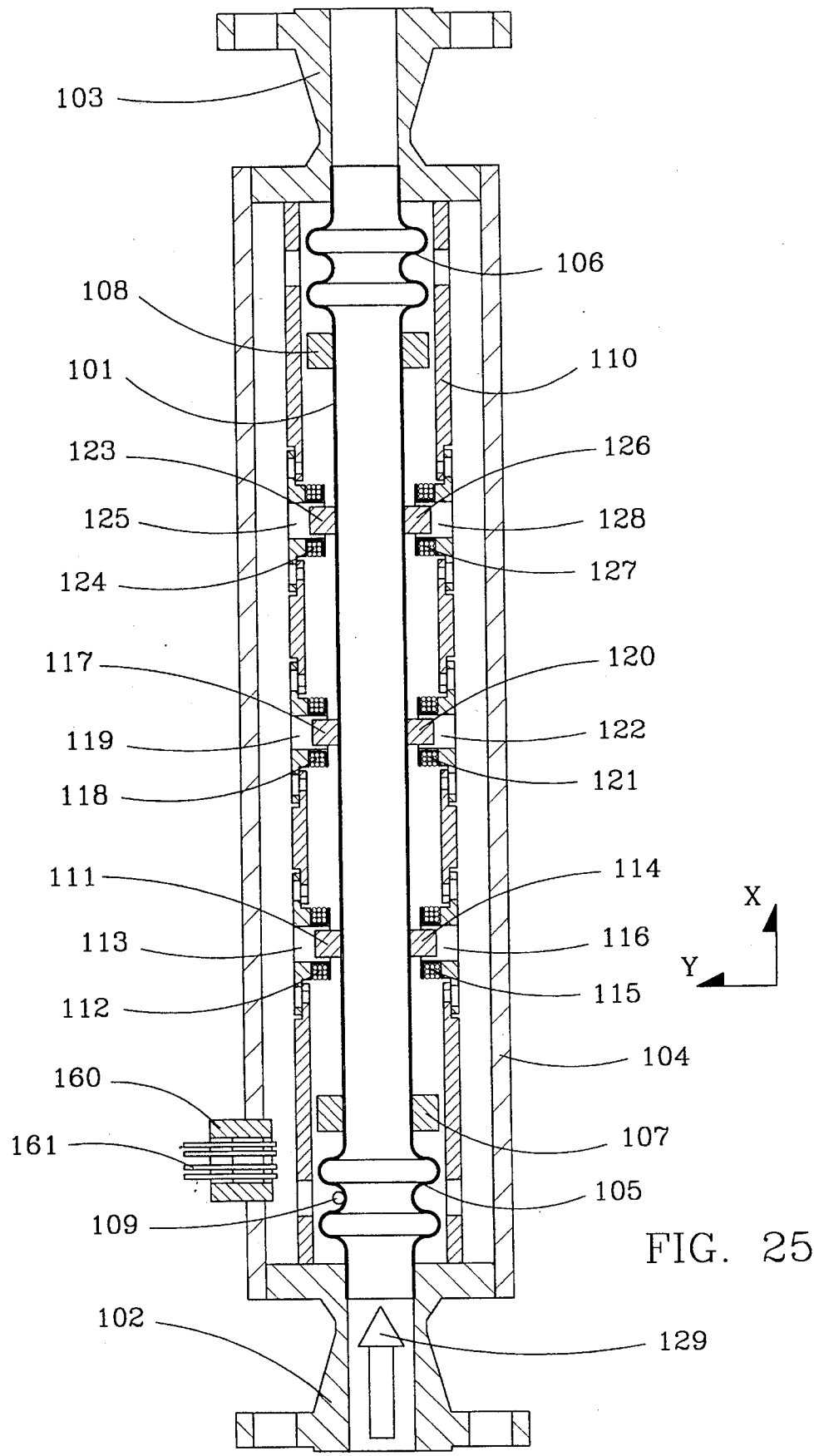
FIG. 25 is an alternate exemplary embodiment of the present invention employing a plurality of motion detectors, vibration isolation means, and axial stress reduction means.

FIG. 25 depicts an alternate embodiment of the present invention using flexible joints 105 and 106 to reduce axial stress effects, and stiffener rings 107 and 108 to isolate the desired radial vibration to a selected portion of flow conduit 101.

Figure 40:
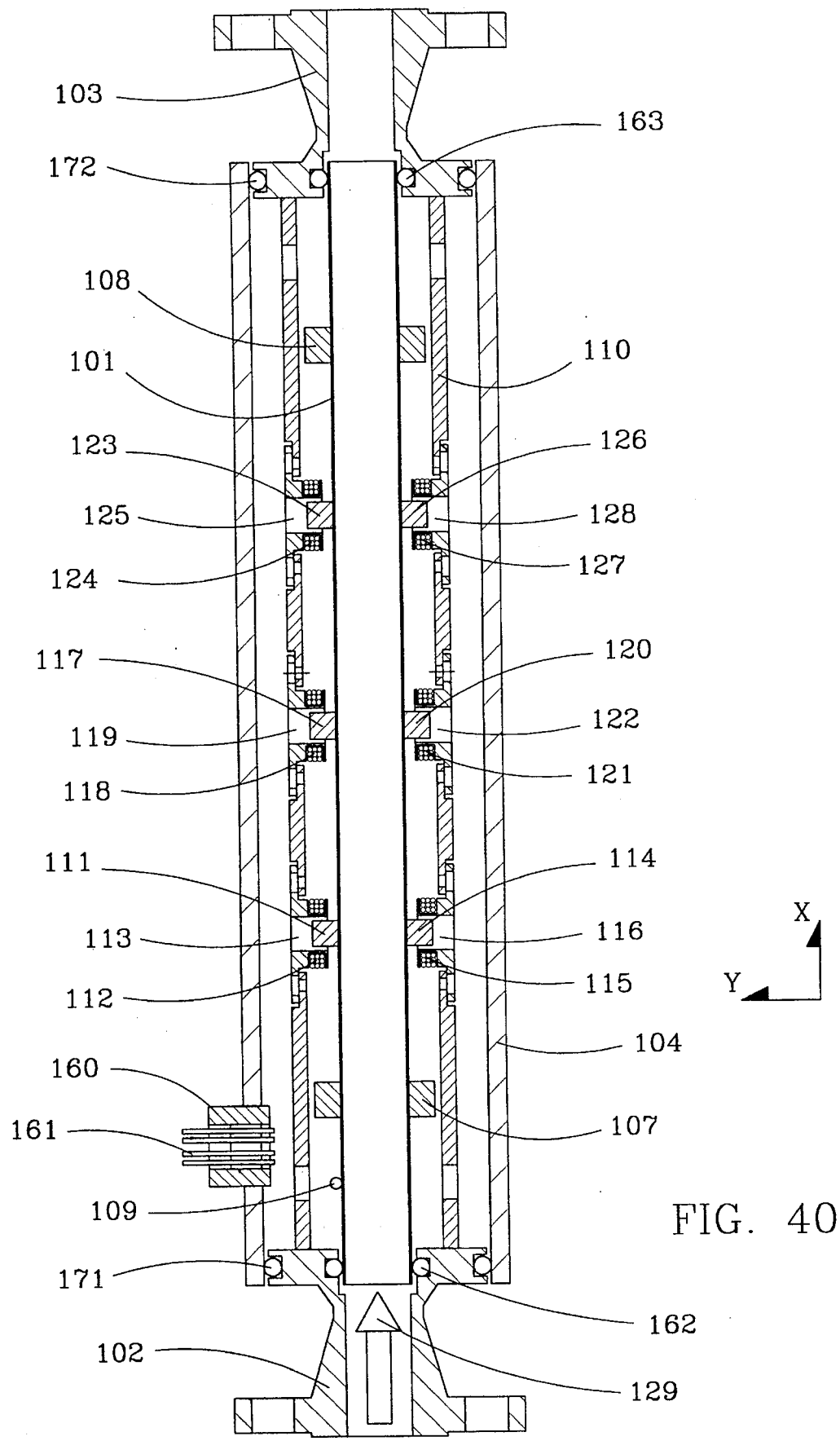
FIG. 40 is a representation of an alternate exemplary embodiment to that of FIG. 25 using a slip joint and seal arrangement instead of a flexible joint arrangement.

FIG. 40 depicts an alternate embodiment of the present invention using a slip joint arrangement where flow conduit 101 passes through seals 162 and 163 to eliminate axial stress effects.

This thermally induced axial stress effect can also be minimized by using a material for both case 4 and conduit 1 with a low coefficient of thermal expansion such as quartz or Invar 32-5 by Carpenter Technology Corporation. Since using low-expansion materials for both case 4 and conduit 1 is not always practical, the method employed in the preferred exemplary embodiment of FIG. 1 is to determine the temperature difference between case 4 and conduit 1, then compensate the final output signal 19 of FIG. 16, functionally related to this temperature difference. Accordingly, mounted in association with case 4 is temperature sensor 41 which is preferably a platinum resistance thermal device (RTD), however many other types of temperature sensors could be used. Temperature sensor 41 is used in conjunction with temperature sensor 29 to determine the temperature difference between case 4 and conduit 1.

A pressure difference between the inside and the outside of flow conduit 1 can cause stress which can alter the stiffness and thus the sensitivity of the flow conduit to mass flow rate. For low pressure applications this effect can usually be neglected. For higher pressure applications, the effect can be negated by applying a prescribed pressure to the area between case 4 and conduit 1 using a fluid such as argon,-nitrogen, air, helium, or the process fluid itself, to eliminate or maintain a prescribed amount of stress in conduit 1. In the preferred exemplary embodiment of FIG. 1 a unique method is employed to non-intrusively measure and compensate for this pressure effect using the vibration of flow conduit 1. One observable effect from increasing the pressure difference between the inside and the outside of flow conduit 1 is to increase the frequencies of most of its natural modes of vibration. The amount of frequency increase varies for each mode of vibration and, in general, becomes less for higher frequency modes.

Increasing fluid density adds mass to the vibrating structure which necessarily tends to decrease the natural frequencies of vibration. Since compressible fluids exhibit an increase in pressure accompanied by an increase in fluid density, the net result can be either an increase or a decrease in the frequencies.

The variation in frequency due to pressure and density changes, normally varies for different modes of vibration. Therefore, by finding the value of two prescribed modes of vibration, the density and the pressure difference can thus be determined. Accordingly, conduit 1 is forced to vibrate in two radial modes of vibration to both measure mass flow rate and to determine pressure difference and density as shall further be explained.

Figure 50:
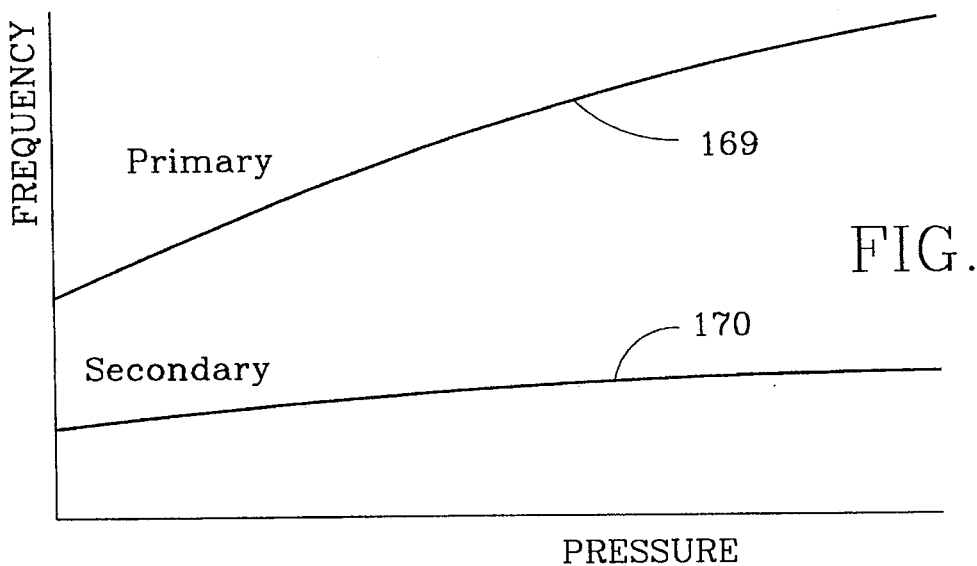
FIG. 50 is a graph of one possible functional relationship between flow conduit vibration frequency and process fluid pressure, for both the primary and secondary vibration modes, for the embodiment of FIG. 25.
Figure 51:
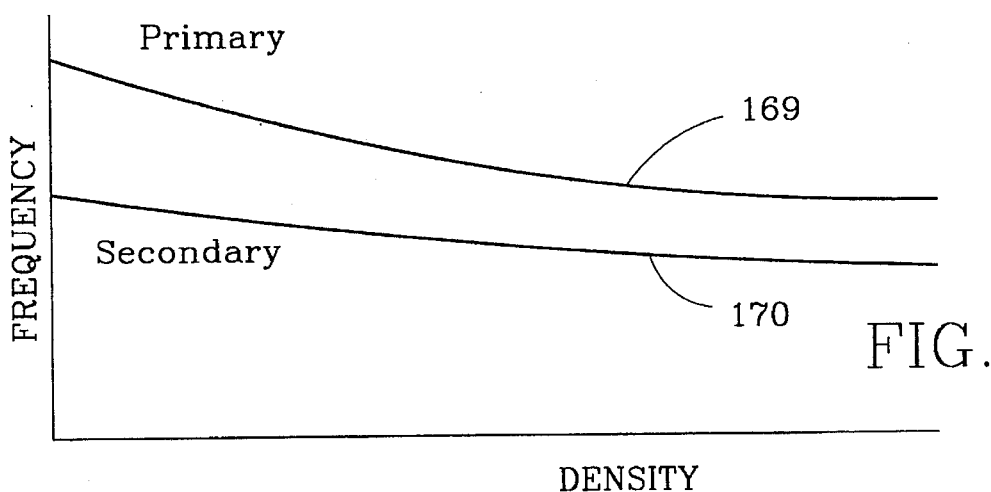
FIG. 51 is a graph of one possible functional relationship between flow conduit vibration frequency and process fluid density, for both the primary and secondary vibration modes, for the embodiment of FIG. 25.

Positioned approximately half way between manifolds 2 and 3 and fixedly attached to conduit 1, are driver magnets 5 and 6 which are arranged diametrically opposite to each other. Magnets 5 and are preferably made of alloys of samarium-cobalt or alnico and can be used with or without a keeper. Associated with magnets 5 and 6 are driver coils 7 and 8, respectively, which are fixedly attached to case 4 and are used in conjunction with magnets 5 and 6 to drive conduit 1 into two prescribed radial-modes of vibration, one radial mode for measuring mass flow rate, and a second reference mode for determination of density and pressure. The second reference mode need not be a radial mode, however, it should change frequency due to pressure or density variations at a different rate than the primary radial mode. Graphical representations of frequency verses pressure and density variations which meet this requirement are shown in FIGS. 50 and 51.

Only one magnet-coil driving source is necessary, however, using two magnet-coil pairs in this manner improves symmetry and balance. Other drive means could be employed to force the requisite radial-mode vibrations such as electroded surfaces on conduit 1 interacting with similar electrodes on the inner surface of case 4, or piezoelectric bender elements, mechanical actuators, and others. In addition, if a ferromagnetic material is used for conduit 1, electromagnetic drivers can be used to force the requisite vibration without the addition of any device fixed to the conduit.

Located part way between driver magnet 5 and manifolds 2 and 3 are pickoff magnets 9 and 10, respectively, which are preferably made of alloys of samarium-cobalt or alnico and are fixedly attached to conduit 1. Arranged in association with pickoff magnets 9 and 10 are pickoff coils 11 and 12, respectively, which are fixedly attached to case 4. Magnet 9 and coil 11 collectively form motion detector 13 which senses the motion of conduit 1 at its location. Magnet 10 and coil 12 collectively form motion detector 14 which senses the motion of conduit 1 at its location. The preferred exemplary embodiment employs magnets and coils as motion detectors however many other types of motion detectors have been successfully tested or anticipated such as strain gages, accelerometers, optical transducers, capacitive transducers, piezoelectric and inductive sensors, and others. Other locations for motion detectors can also be successfully utilized with the requirement that if two motion detectors are used, they are separated from each other by some distance along the length of conduit 1. Symmetrical pairs of pickoff magnets could alternately be used to improve symmetry and balance as was previously explained for drive magnets 5 and 6. Alternate embodiments using symmetrical pairs of pickoff magnets are shown in FIGS. 25 and 40.

Figure 2:
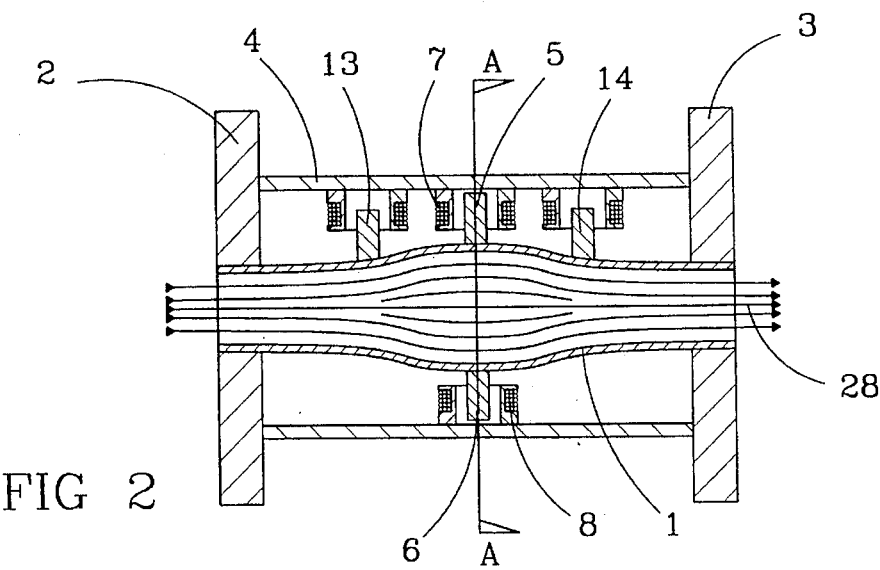
FIG. 2 is a cross-sectional view of the embodiment of FIG. 1 showing the radial-mode vibration shape of the flow conduit where it has reached its peak deflection in the vertical direction.
Figure 3:
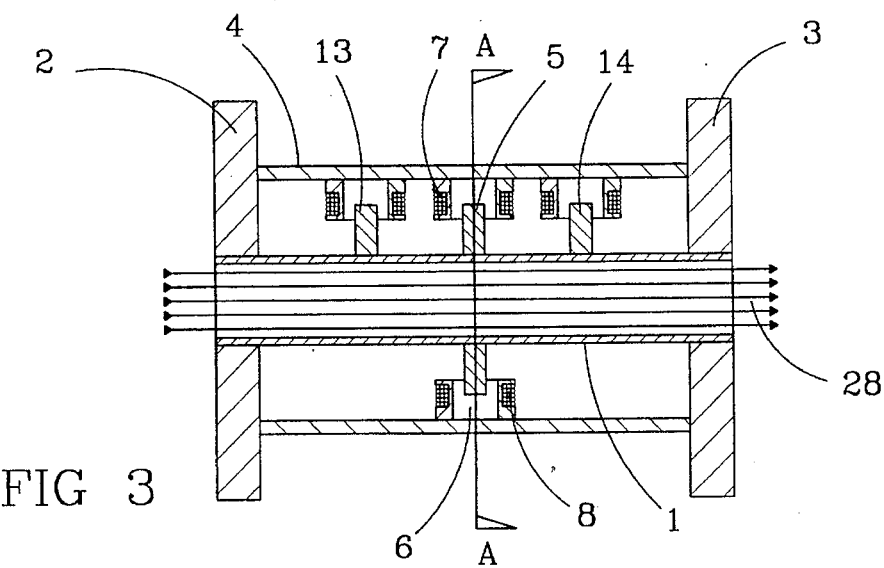
FIG. 3 is a cross-sectional view of the embodiment of FIG. 1 showing the radial-mode vibration shape of the flow conduit where it has reached its undeflected center position. This is also representative of the flow conduit's rest position.
Figure 4:
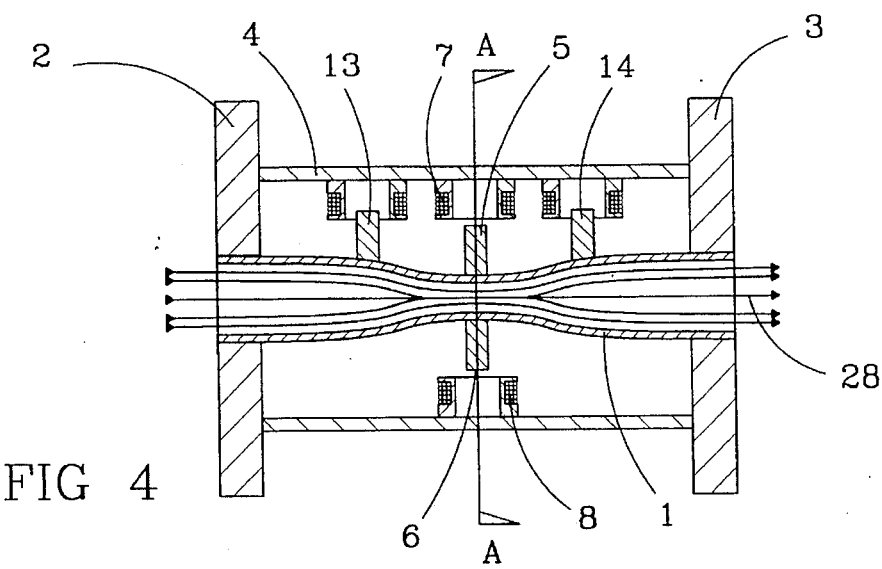
FIG. 4 is a cross-sectional view of the embodiment of FIG. 1 showing the radial-mode vibration shape of the flow conduit where it has reached its peak deflection in the horizontal direction.
Figure 5:
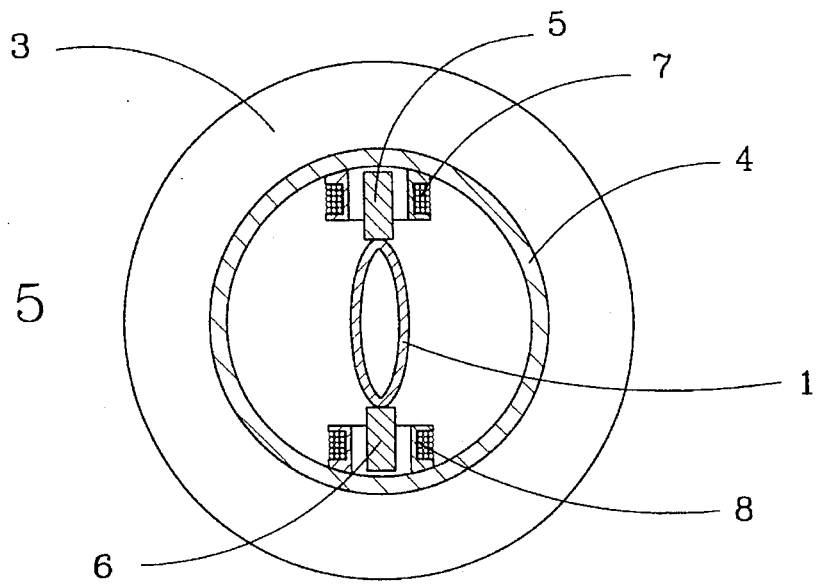
FIG. 5 is a cross-sectional view along section A—A in FIG. 2 showing the elliptical cross-sectional shape of the flow conduit at its peak deflection in the vertical direction.
Figure 6:
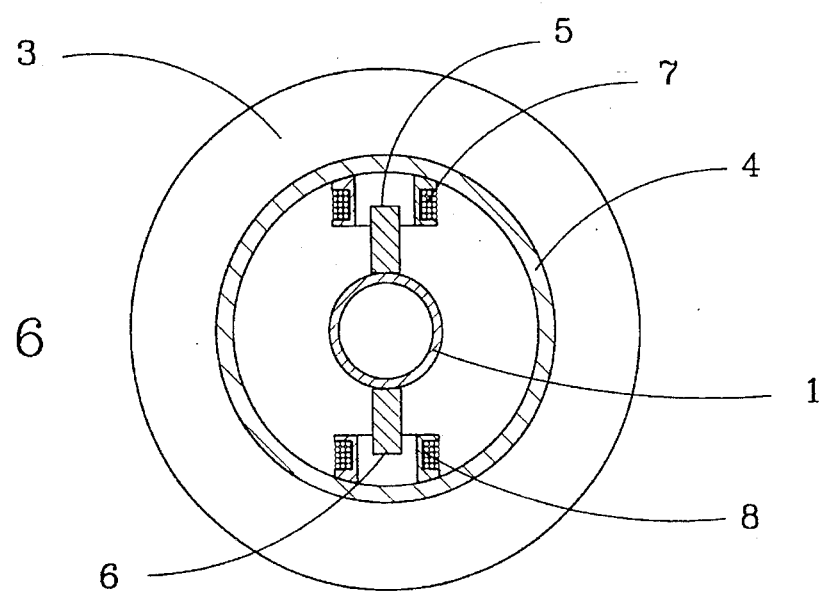
FIG. 6 is a cross-sectional view along section A—A of FIG. 3 showing the circular cross-sectional shape of the flow conduit as it passes through its undeflected center position.
Figure 7:
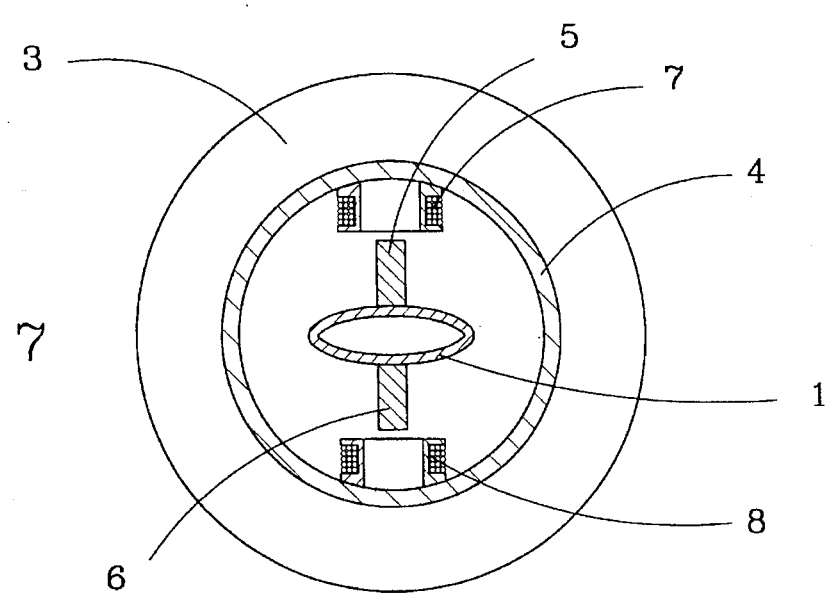
FIG. 7 is a cross-sectional view along section A—A in FIG. 4 showing the elliptical cross-sectional shape of the flow conduit at its peak deflection in the horizontal direction.
Figure 10:
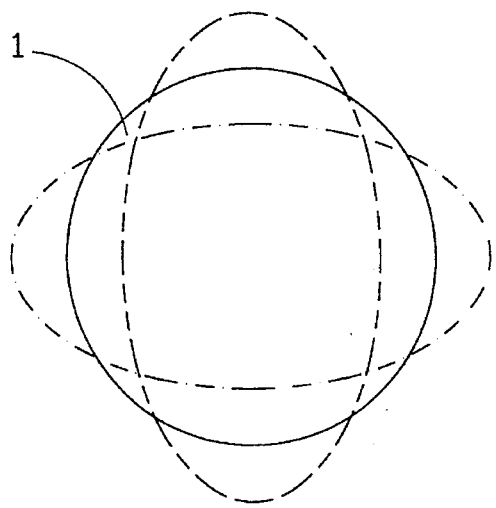
FIG. 10 is a cross-sectional representation of the two-lobe radial-mode vibration of the flow conduit in the preferred exemplary embodiment of FIG. 1 shown with three sequential deflected shapes (peak vertical, undeflected, peak horizontal) superimposed on each other.
Figure 13:
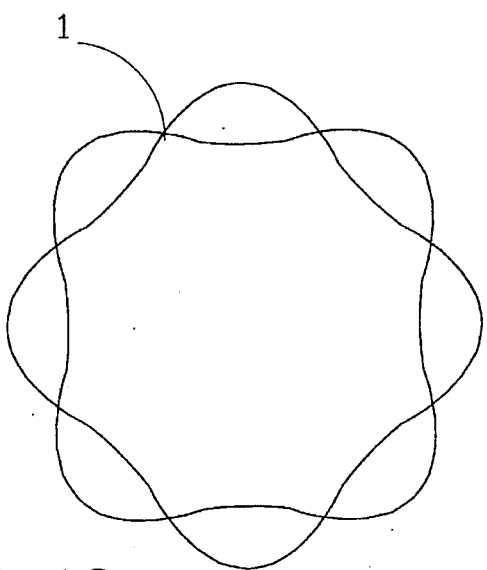
FIG. 13 is cross-sectional representation of an alternate radial-mode of vibration to that shown in FIG. 10 with two sequential deflected shapes superimposed on each other.
Figure 16:
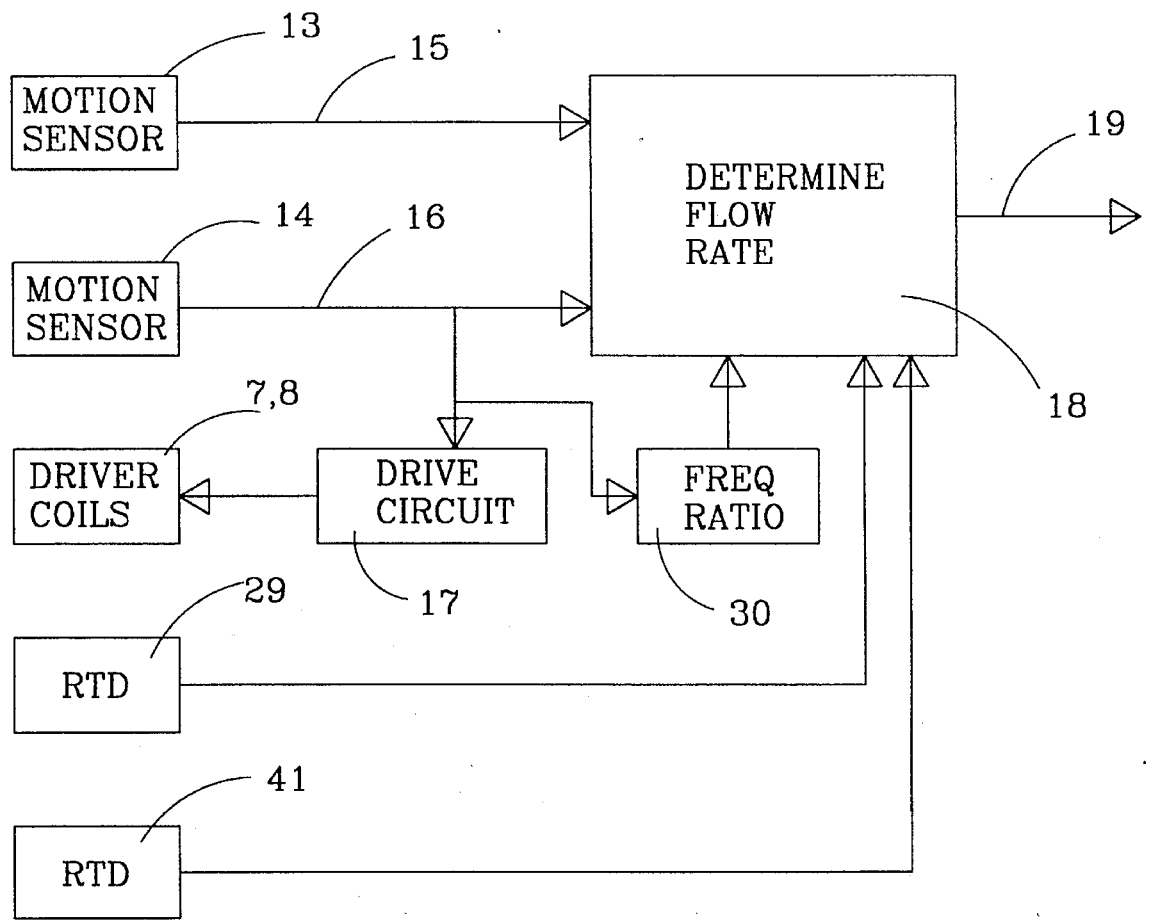
FIG. 16 is a block diagram of one possible configuration of circuit components used to measure mass flow rate according to the present invention.

The operation of the preferred exemplary embodiment shall now be described. Driver coils 7 and 8 are electrically excited to produce two simultaneous radial-mode vibrations. The primary mode is the two-lobe mode as shown in FIGS. 2 through 7 and in FIG. 10, which depict the sequence of conduit motion from elliptically elongated in the vertical direction (FIGS. 2 and 5) through a round undeflected shape (FIGS. 3 and 6) to being elliptically elongated in the horizontal direction (FIGS. 4 and 7). FIG. 10 shows the same sequence of three cross sectional shapes of conduit 1 superimposed on each other. The amplitude of elliptical deformation progresses from zero deformation at the fixed ends of conduit 1 to a maximum deformation near the center at drive magnets 5 and 6. This change in amplitude of the radial vibration along the length of flow conduit 1 is necessary to cause the requisite Coriolis forces for mass flow measurement. The secondary vibration mode is preferably the four-lobe mode as shown in FIG. 13, however other radial and bending modes have successfully been tested or anticipated. The primary mode is used to cause the requisite Coriolis forces and as such is maintained at a sufficiently high amplitude limited by material, fatigue and stress factors. The secondary mode is used as a reference frequency to determine the density and the pressure difference across the wall of flow conduit 1 and is therefore maintained at a minimum detectable level so as not to interfere with or significantly contribute to the motion detector signals 15 and 16. These vibrations are maintained by using signal 16 from motion detector 14 in a feed-back loop to circuit component 17 as shown in FIG. 16 which in turn applies a reinforcing signal to driver coils 7 and 8 with energy at the appropriate frequencies and phases to maintain the prescribed vibrations. As an alternate to maintaining the secondary vibration mode continuously for pressure difference determination, it can be turned on and off as necessary in a sampling technique.

Figure 14:
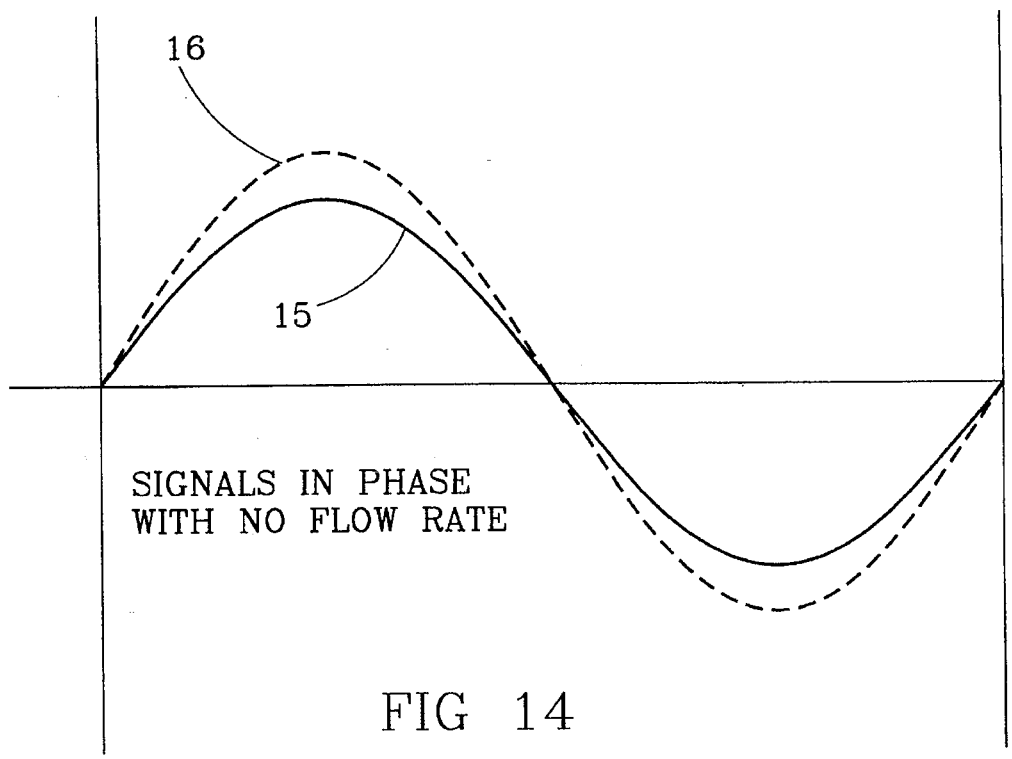
FIG. 14 is a representation of the time relationship of signals from the motion detectors of FIG. 1 with no fluid flowing through the flow conduit.

Once the desired motion is established, motion detectors 13 and 14 will produce essentially sinusoidal signals 15 and 16 at the frequency of the primary vibration, and substantially equal in phase when no fluid is flowing in conduit 1 as shown in FIG. 14. When process-fluid flows through conduit 1, the direction of the fluid velocity changes to track the shape of the conduit during its radial-mode vibration. Referring to FIG. 2, the direction of fluid 28 entering from the left side is essentially parallel with the axis of conduit 1 as it passes through manifold 2. Between manifold 2 and driver magnet 5, fluid 28 (along the upper and lower surfaces of flow conduit 1) diverges away from the conduit center-line to track the shape of conduit 1. As the fluid 28 passes under drive magnet 5 its direction is again parallel with the axis of conduit 1. Between drive magnet 5 and manifold 3, fluid 28 converges toward the conduit center-line. Upon reaching manifold 3 fluid 28 is again moving parallel with the axis of conduit 1. As the elliptical deformation of conduit 1 passes through its circular (undeflected) shape as in FIG. 3, all the fluid 28 is shown parallel to the center-line of conduit 1. FIG.

Figure 15:
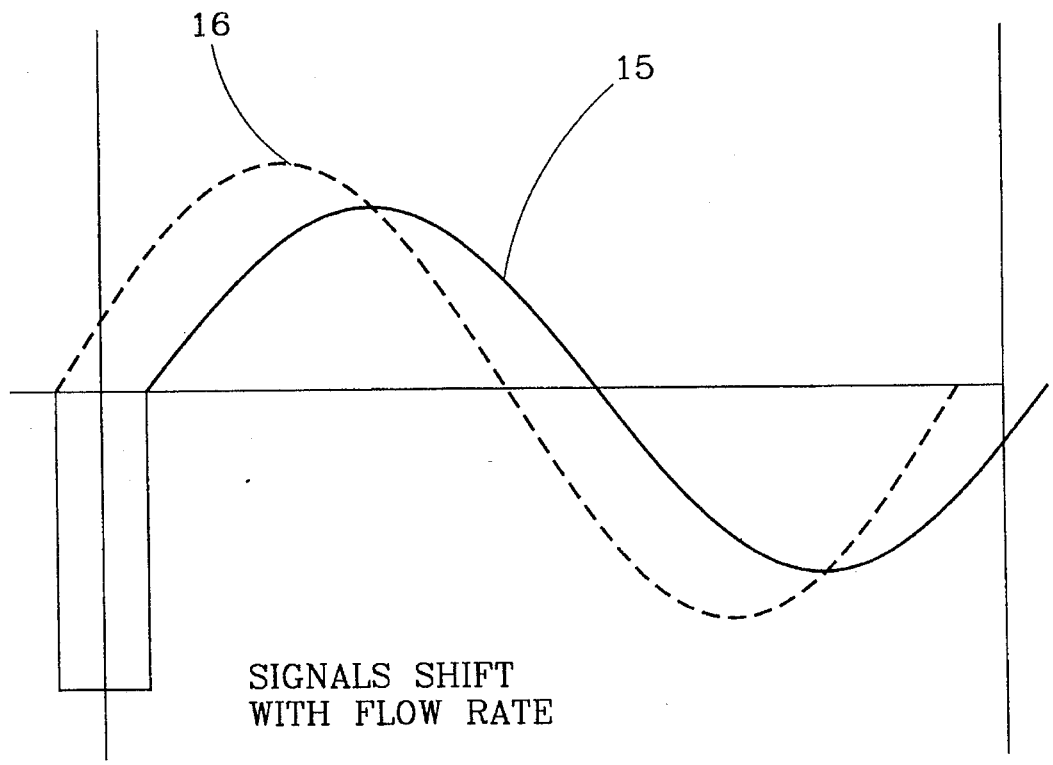
FIG. 15 is a representation of the time relationship of signals from the motion detectors of FIG. 1 with fluid flowing through the flow conduit.

4 shows conduit 1 at its peak deflection in the horizontal direction. In this FIGURE, fluid 28 along the top and bottom surfaces entering from the left, first converges toward the center-line of conduit 1, then becomes parallel to the axis of the conduit as it passes below drive magnet 5, then diverges away from center-line toward the right side of conduit 1, and finally exiting in a parallel direction. FIGS. 2 and 4 clearly show the change in direction of the fluid 28 along the top and bottom surfaces of flow conduit 1 however, since these FIGS show the conduits peak deflections, the conduit motion is essentially stopped at these positions thus causing no Coriolis forces. It is when conduit 1 passes through its center position of FIG. 3 that its shape is changing most rapidly and thus can cause the greatest Coriolis forces. Coriolis forces will thus be produced proportionally related to the mass of the moving fluid, its velocity, and the rate of change of its direction. Since the rate of change in the fluid direction along the top surface of conduit 1 is opposite to that along the bottom surface, a Coriolis force distribution along the upper and lower surfaces of conduit 1 is thereby created similar to that shown in FIG. 8. The fluid motions and Coriolis force distributions just described pertained to the upper and lower surfaces of conduit 1, however, during the forced radial-vibration the sides of conduit 1 move in the opposite sense to the upper and lower surfaces. Accordingly, another similar Coriolis force distribution will also be caused along the sides (90 from the top and bottom surfaces) of conduit 1 with the direction of forces reversed (not shown). All these Coriolis force distributions reach a maximum value and thus will most greatly alter the shape of conduit 1 as it passes through its normally circular position (FIG. 3). One measurable effect of these forces is to deform conduit 1 into a shape similar to that shown in FIGS. 9 through 9C where the amount of deformation shown is greatly exaggerated for clarity. This deformation thereby causes a difference between signals 15 and 16 which can then be measured in a variety of ways as an accurate indication of mass flow rate. One measurable effect of this deformation is to delay the phase or time relationship of the radial-mode vibration toward the fluid entry end of conduit 1, and advance the phase or time relationship of the radial-mode vibration toward the fluid exit end of conduit 1. In the preferred exemplary embodiment therefore, this phase or time relationship is used to measure mass flow. This effect will cause signal 16 to precede signal 15 in time by an amount that is a function of mass flow rate, as shown in FIG. 15. Signals 15 and 16 are then applied to circuit component 18 of FIG. 16 which compares the phase or time difference between signals 15 and 16, and according to a prescribed function, creates an output signal 19 proportionally related to mass flow rate.

Figure 23A:
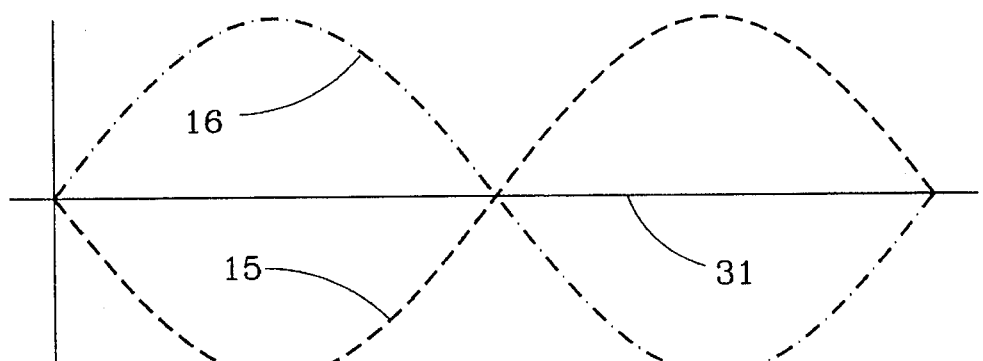
FIG. 23A is a representation of the signals from the motion detectors of FIG. 1, and their sum with one of the signals inverted and with no flow through the flow conduit.
Figure 23B:
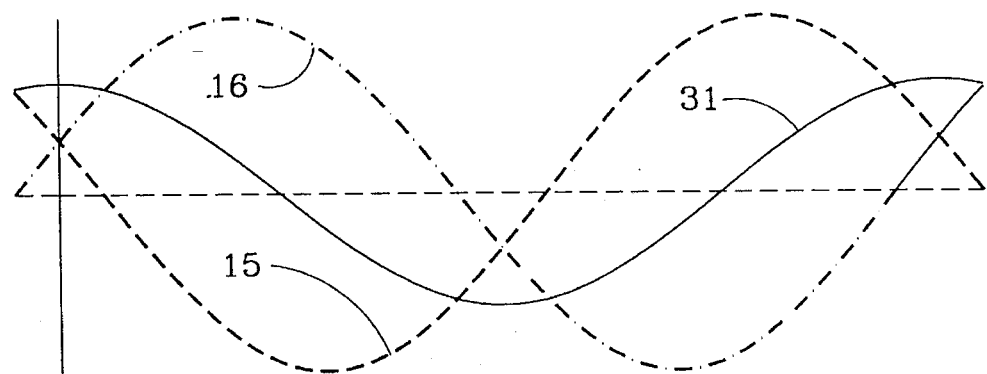
FIG. 23B is a representation of the signals from the motion detectors of FIG. 1, and their sum with one of the signals inverted and with flow through the flow conduit.

Another way to utilize motion detector signals 15 and 16 to measure mass flow rate is to invert one of the signals (180 phase shift) then add them both together, as shown in FIG. 23A. If there is no fluid flow through conduit 1 and the amplitudes of signals 15 and 16 are the same, the resulting sum 31 will be zero or a DC value. With fluid flow in conduit 1, the phase relationship between signals 15 and 16 will change as shown in FIG. 23B causing their sum 31 to be a resultant sine-wave whose amplitude is related to mass flow rate, and whose phase is related to fluid flow direction through conduit 1.

Another method to determine mass flow rate is to maintain the driven amplitude to be a constant value and measure the amplitude of either motion detector signal (15 or 16). The amplitude of the motion sensed at the fluid entry end of conduit 1 (signal 15) will be slightly reduced while the amplitude at the fluid exit end of conduit 1 (signal 16) will be slightly greater, as a function of mass flow rate. Using this method only a single motion detector is required for operation, however using both signals 15 and 16 doubles the available measurement and would thus be preferable. Many other methods that utilize a change in one or both of the motion detector signals to determine mass flow rate have been successfully tested or anticipated.

Circuit component 30 of FIG. 16 accepts input from motion detector signal 16 and determines the ratio of the primary frequency to the secondary frequency of conduit 1. This can be done using filter circuits to isolate the individual frequencies and then employing timing circuits to measure their periods, digital techniques involving Fast Fourier Transforms (FFT), specific arrangements of pickoffs which isolate the individual vibrations, and others. Component 30 then provides a signal proportional to this frequency ratio to circuit component 18. Component 18 also accepts input from temperature sensors 29 and 41 and compensates the final output signal 19 as necessary to correct for the effects of temperature, thermally induced axial stress, and pressure difference. The final output signal 19 can then be used as an accurate indication of mass flow rate by other equipment for purposes such as monitoring flow rate, controlling valves, proportional mixing, batching, and others.

The initial non-flow phase relationship (zero phase difference in this example) of signals 15 and 16 in FIG. 14 is a consequence of the angular position of motion detectors 13 and 14 around the circumference of conduit 1. For example, if motion detector 14 was rotated 90 around the circumference of conduit 1 (not shown), then the non-flow phase relationship between signals 15 and 16 would be 180 (inverse phase) from each other. This fact can used to set a desired initial phase relationship between signals 15 and 16.

In the preferred exemplary embodiment of FIG. 1 a "natural" radial-mode of vibration was chosen for both the primary and the secondary frequencies since the power necessary to maintain a natural mode of vibration is normally less than that required to maintain a forced vibration that is not a natural mode. It is however not necessary to use a natural mode of vibration and in some circumstances it may be advantageous to force a flow conduit into a desired radial vibration at a non-natural frequency. For example, if a conduit material such as reinforced rubber or neoprene was used, the high damping coefficient of such materials would make a natural mode of vibration difficult to maintain, therefore a flow conduit of this nature could be forced to radially vibrate at a selected frequency.

Figure 11:
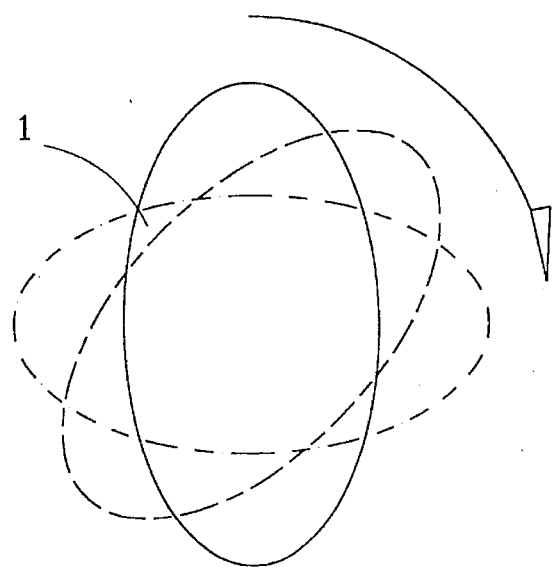
FIG. 11 is a cross-sectional representation of an alternate radial-mode of vibration to that shown in FIG. 10 with three sequential deflected shapes superimposed on each other.
Figure 12:
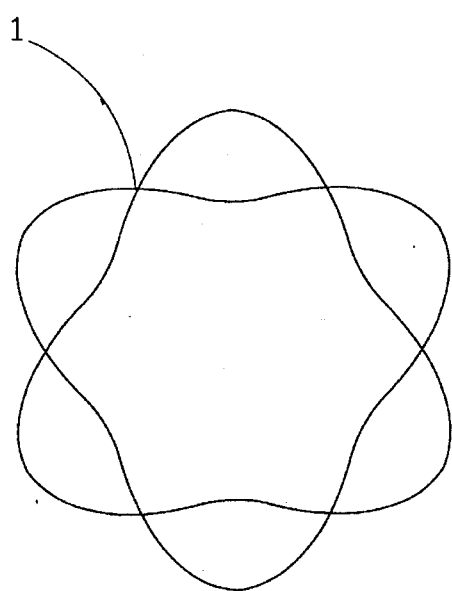
FIG. 12 is cross-sectional representation of an alternate radial-mode of vibration to that shown in FIG. 10 with two sequential deflected shapes superimposed on each other.

Alternate modes of vibration for either the primary or the secondary modes can be employed to enhance various performance characteristics. Alternate modes include the rotating elliptical mode of FIG. 11 where the elliptical-cross-sectional shape is forced to precess around the conduit center-line never returning to a circular shape. In addition, a three lobed radial-mode as shown in FIG. 12 or a four lobed mode as shown in FIG. 13 could also be used as well as precessing versions of the three and four lobed modes (not shown) and others.

Figure 9:
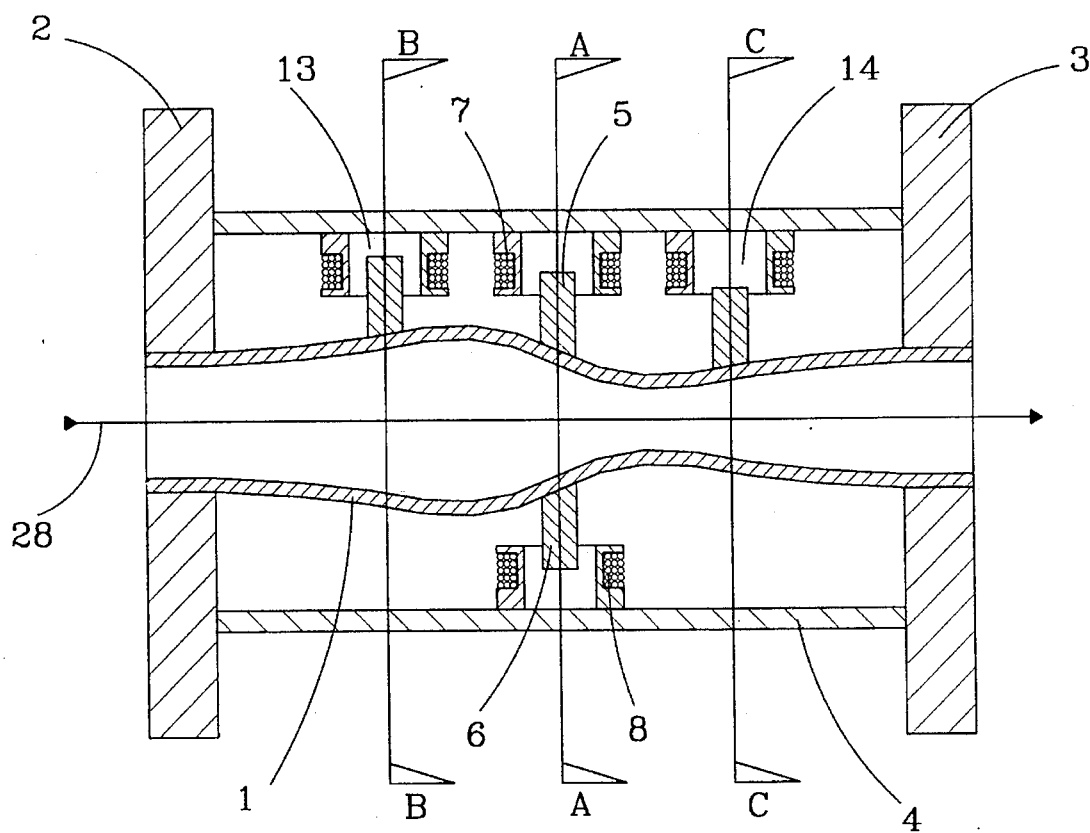
FIG. 9 is a cross-sectional view similar to that of FIG. 3 showing greatly exaggerated representative deflections of the flow conduit resulting from the Coriolis force distribution shown in FIG. 8.
Figure 9A:
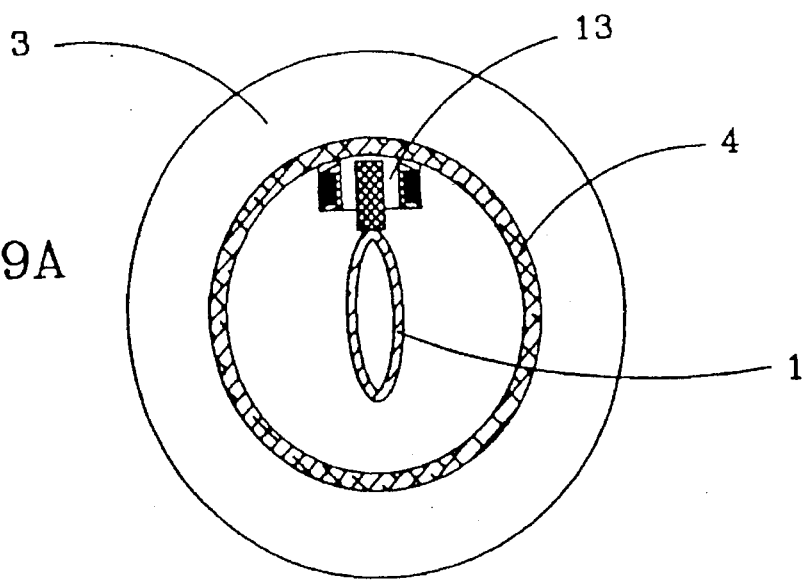
FIG. 9A is a cross-sectional view along section B—B of FIG. 9 showing the deformation of the cross-sectional shape of the flow conduit (greatly exaggerated) due to Coriolis forces, as the flow conduit passes through its center (normally undeformed) position.
Figure 9B:
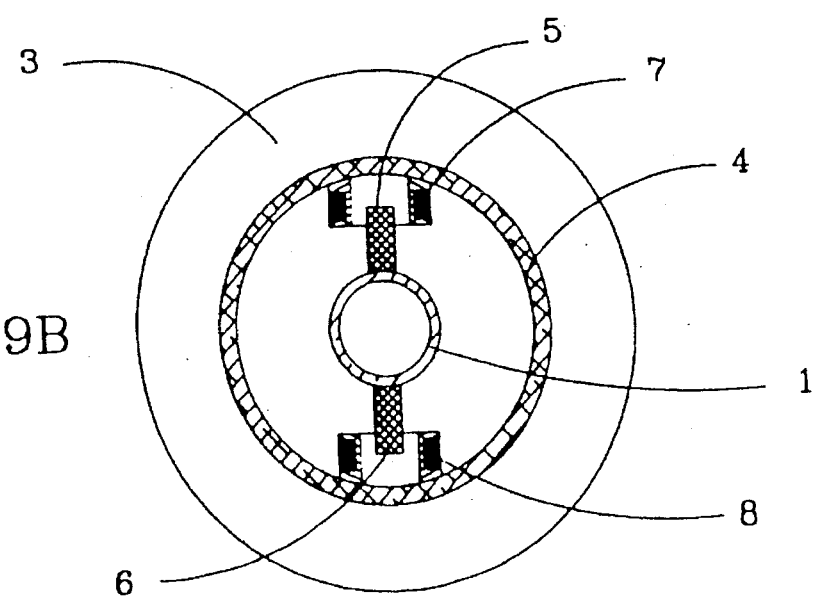
FIG. 9B is a cross-sectional view along section A—A of FIG. 9 showing essentially no deformation of the cross-sectional shape of the flow conduit due to Coriolis forces, as the flow conduit passes through its center position.
Figure 9C:
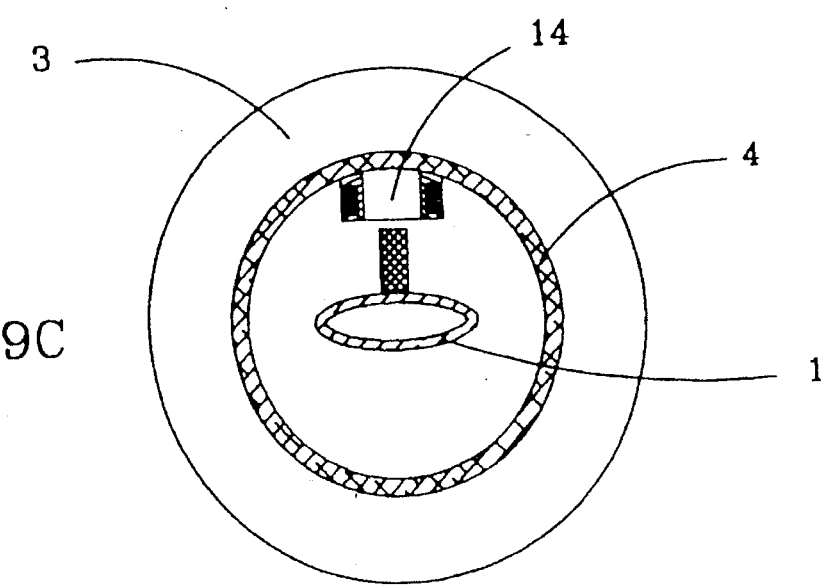
FIG. 9C is a cross-sectional view along section C—C of FIG. 9 showing the deformation of the cross-sectional shape of the flow conduit (greatly exaggerated) due to Coriolis forces, as the flow conduit passes through its center (normally undeformed) position.

In addition to radial-modes of vibration having increasing numbers of lobes around the perimeter of the flow conduit as just described, radial-modes which involve successive reversals of cross-sectional shape along the length of the flow conduit can also be used. FIGS. 9 through 9C show the deformed shape of flow conduit 1 due to mass flow rate, as previously explained. This deformed shape (response mode) is also representative of another natural mode of vibration of conduit 1 where the vertically elongated elliptical deformation at the fluid entry end (FIG. 9A) is reversed into the horizontally elongated deformation at the fluid exit end (FIG. 9C). Since this shape represents a natural mode of vibration, this fact can be used to enhance the frequency response of the structure and achieve greater sensitivity to mass flow rate. The amount of sensitivity gain that can be achieved in this way depends on the ratio of the driven frequency to that of the response mode frequency according to the following equation, the absolute value of which is plotted in FIG. 20.

$$\text{GAIN} = \frac{1}{1 - (D/R)^2} \quad (1)$$

Where:
D=Driven frequency
R=Response mode frequency

Figure 20:
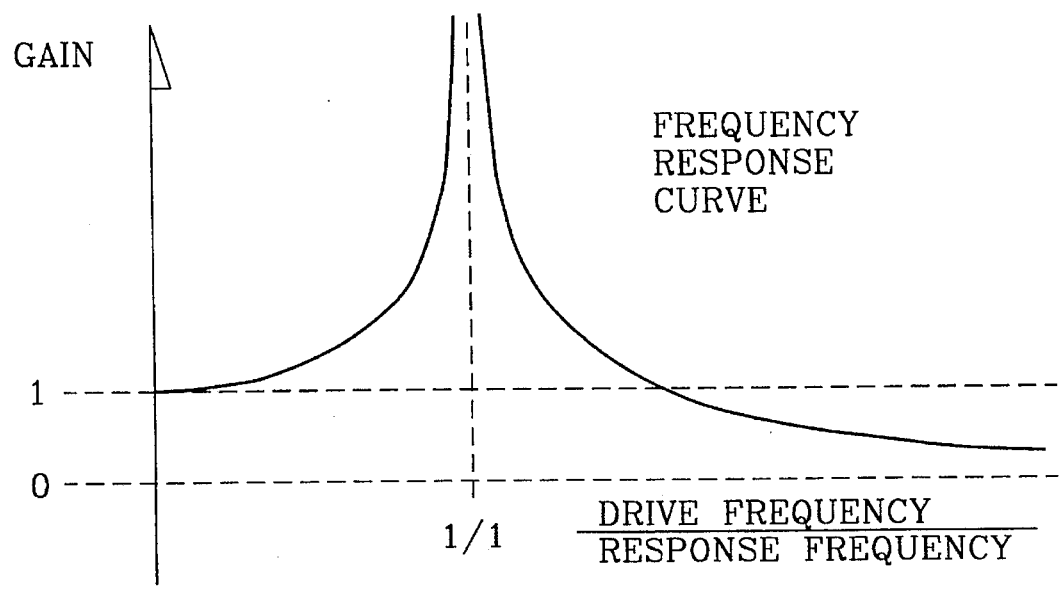
FIG. 20 is a graph of the frequency response curve and is representative of the absolute value of equation No. 1.
Figure 21:
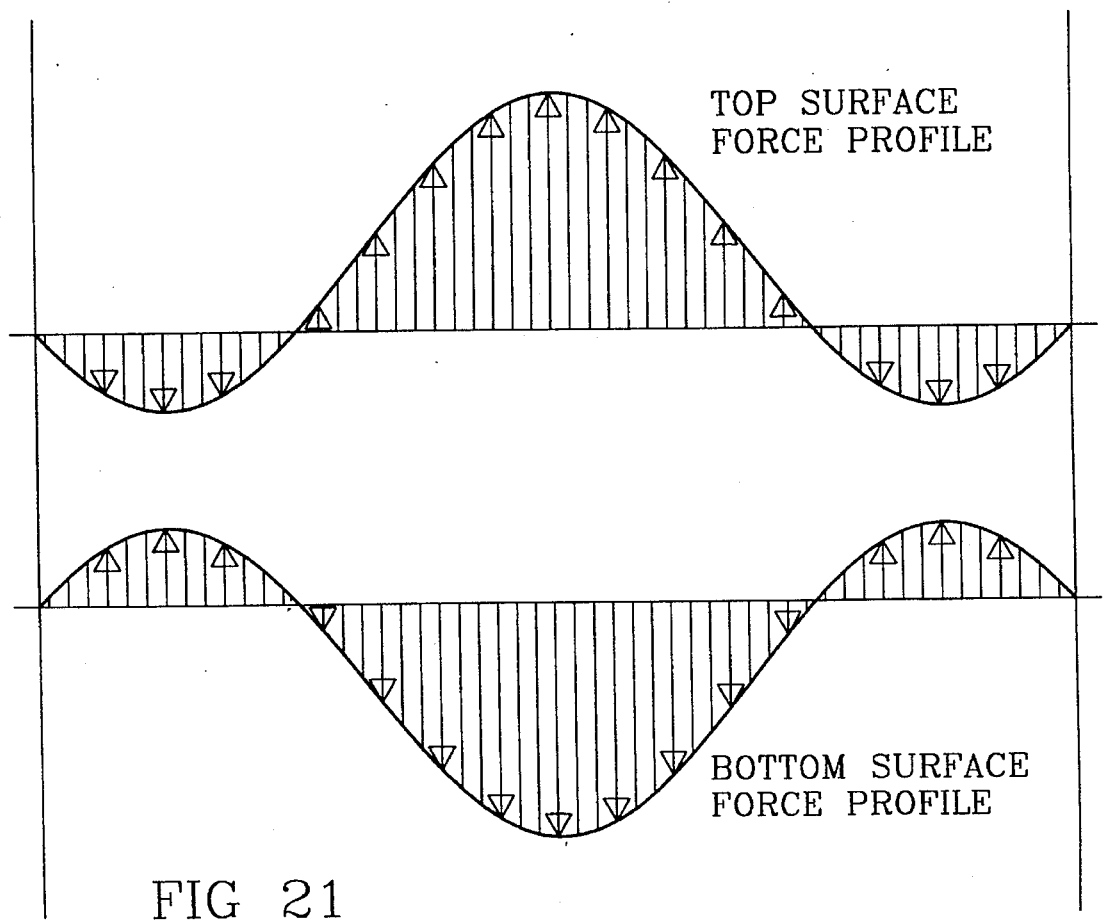
FIG. 21 is a representation of the Coriolis force distribution along the top and bottom surfaces of the flow conduit resulting from driving the flow conduit in a mode shape similar to that shown in FIG. 9.

According to equation 1, the gain will approach infinity as the driven frequency approaches the response mode frequency. Operating on either side of the peak of FIG. 20 is acceptable. Operating on the right side of this peak means that the driven frequency is greater than the response mode frequency which can occur in the following way. If flow conduit 1 of FIG. 1 is forced to vibrate in the shape depicted in FIG. 9 as the primary driven mode, the induced Coriolis force distribution along the top and bottom surfaces of the conduit will be as shown in FIG. 21. Although this force distribution reverses its direction several times along the length of the conduit, since the ends of the conduit are fixedly attached and so are relatively inflexible, the center portion of the Coriolis force distribution will be the dominant factor with the overall effect that conduit 1 will deform into a shape similar to the earlier described primary driven mode as shown in FIGS. 2 through 7, proportionally related to mass flow rate. Since, for the preferred exemplary embodiment, the frequency of the mode shown in FIG. 9 (with one reversal in deflection direction along its length) is higher than the mode shown in FIGS. 2 through 7 (with no reversal), the ratio of the driven frequency to the response frequency is greater than one and thus constitutes working on the right side of the peak of FIG. 20. Another consequence of operating on the right side of the peak in FIG. 20 is that the phase shift of signals 15 and 16 is reversed so that signal 15 would precede signal 16 as a function of mass flow rate (not shown).

It is therefore anticipated that any radial-mode of vibration, either natural or forced, can be used as the primary drive mode to create Coriolis forces which will deform the shape of flow conduit 1, proportionally related to mass flow rate. Similarly, any mode of vibration can be used as the secondary reference vibration to determine the density and pressure difference across the wall of the flow conduit, with the requirement that the secondary reference frequency must change as a function of fluid pressure and density by a different amount than the primary driven frequency.

A unique consequence of the overall shape and operation of the preferred exemplary embodiment of FIG. 1 is that manifolds 2 and 3 can be designed as aerodynamically or hydrodynamically shaped fittings, and the device can be mounted open ended in a moving fluid stream such as on the wing of an airplane or the hull of a ship. In this arrangement, fluid flow through the meter can be related to its velocity relative to the surrounding fluid thereby creating a velocity meter.

Figure 17:
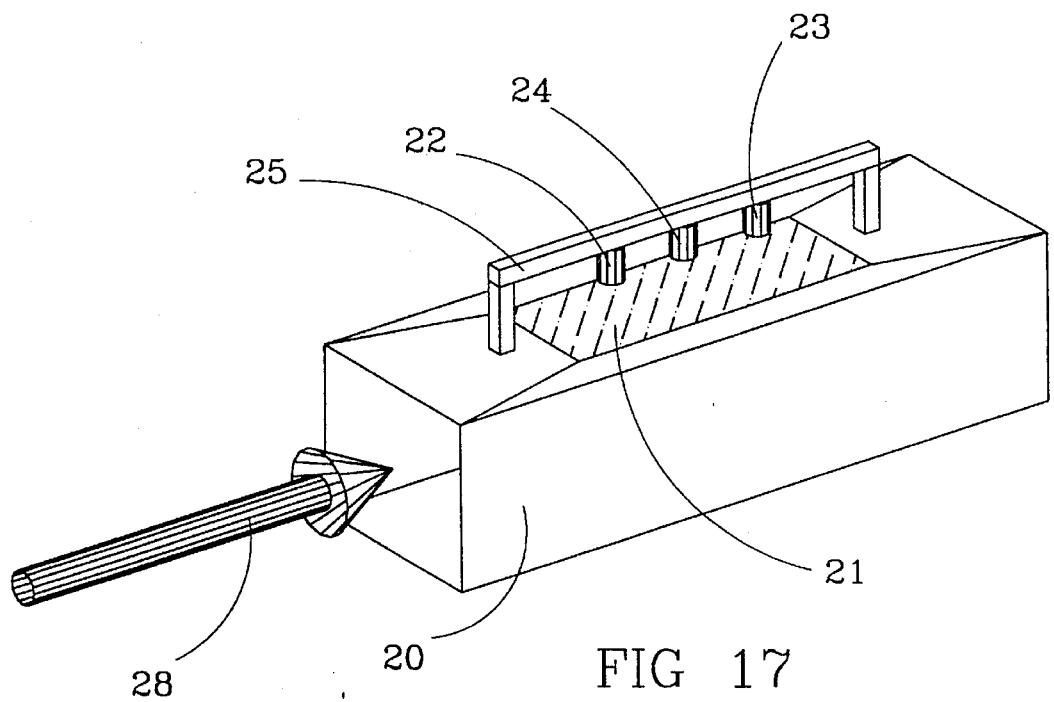
FIG. 17 is a perspective view of an alternate to the preferred exemplary embodiment of FIG. 1 using a vibrating flexible surface as part of a rectangular flow conduit perimeter to measure the mass flow rate in the conduit.
Figure 18:
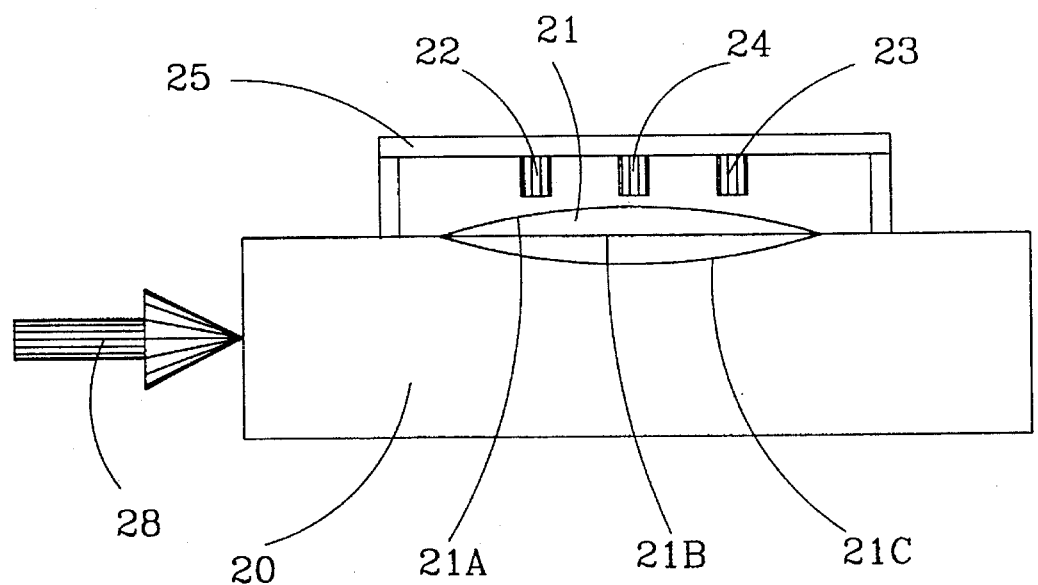
FIG. 18 is a cross-sectional view through the embodiment of FIG. 17 showing three sequential deflected shapes of the vibrating flexible surface with no fluid flow.

As an alternate to using a radial-mode of vibration involving the entire perimeter of the flow conduit, certain applications, especially low pressure, large thin-walled or non-circular flow conduits, or micro-flow meters etched or machined into bulk materials such as semiconductors or quartz, can be accommodated by vibrating only a portion of the flow conduit perimeter in a radial manner. The rectangular flow conduit of FIG. 17 is well suited for low pressure applications such as air flow in duct systems, however, flow conduits that are large in comparison with their wall thickness, and conduits with flat sides can be impractical to vibrate in radial-modes involving the entire perimeter. Similarly, flow conduits that are formed into bulk materials such as silicon or quartz, will have flow conduit sides which are essentially rigid therefore not able to be vibrated in a radial-mode of vibration involving the entire conduit perimeter. The design of a Coriolis mass flow rate meter according to the present invention for these applications can therefore be accommodated by radially vibrating only a portion of the flow conduit perimeter to create the requisite Coriolis force distribution necessary to measure flow rate. In the embodiment of FIG. 17, flow conduit 20 is an example of an ordinary sheet metal rectangular air duct into which is installed flexible surface 21 preferably made of a strong flexible material such as carbon steel sheet metal. Alternately, surface 21 could be a portion of flow conduit 20 which is vibrationally isolated by stiffeners (not shown) analogous in function to stiffener 27 of FIG. 24. Surface 21 is flexibly attached to conduit 20 at its fluid entry and exit ends, and essentially free along it's sides to accommodate radial vibration, except that the sides can be sealed from leakage with a flexible membrane (not shown). The sides of surface 21 could alternately be flexibly attached to conduit 20 however having the sides free enhances flexibility and thus sensitivity to mass flow rate. Surface 21 is forced to radially vibrate by electromagnetic motion driver 24 which is fixedly attached to mounting bar 25 as shown in FIG. 17. The radial vibration of surface 21 is shown in FIG. 18 at its upper 21A, middle 21B Land lower 21C positions of its vibration.

Figure 8:
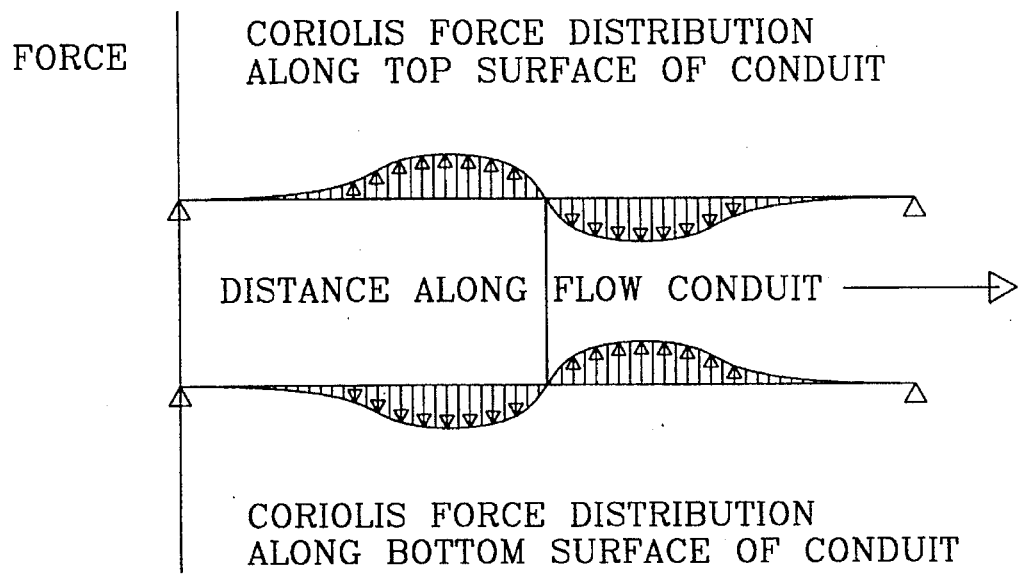
FIG. 8 is a graph of the Coriolis force distribution that would be created along the top and bottom surfaces of the flow conduit from mass flow rate, as the flow conduit passes through its undeflected center position as in FIG. 3.
Figure 19:
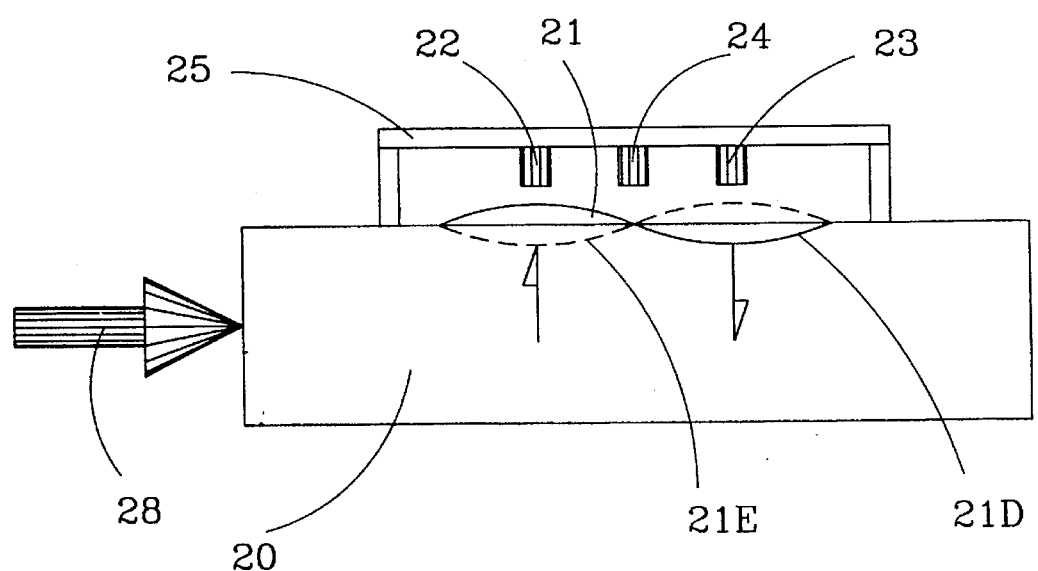
FIG. 19 is a cross-sectional view through the embodiment of FIG. 17 showing the deflected shape of the vibrating flexible surface due to Coriolis forces with fluid flowing through the flow conduit.

The combination of the radial vibration of surface 21 and fluid flow 28 will cause a Coriolis force distribution along the inner face of surface 21 similar to the top surface Coriolis force distribution shown in FIG. 8. This will cause surface 21 to deform slightly into a sine-wave like shape 21D as shown in FIG. 19, as it passes downward through it is normally flat center position, then deforming into an inverted sine-wave like shape 21E as shown in FIG. 19, as it passes upward through it is normally flat center position, thereby causing a difference in the signals produced by motion detectors 22 and 23. One measurable effect of this deformation is that the motion of surface 21 becomes delayed in time at the fluid entry end of conduit 20, and advanced in time at the fluid exit end of conduit 20 as a function of mass flow rate through conduit 20. Motion detectors 22 and 23 are fixedly attached to mounting bar 25 at positions separated from each other by some distance along the length of surface 21. Signals from motion detectors 22 and 23 (not shown) will therefore be shifted in time from each other by an amount related to the mass flow rate of process-fluid in conduit 20 analogous to signals 15 and 16 in FIG. 15. It is anticipated that the flexibility of surface 21 and thus the sensitivity of the device to mass flow rate, can be enhanced by proper configuration and material choice of flexible surface 21, or by mounting surface 21 on flexural supports such as diaphragms, bellows, hinges, fabric and the like. Some possible materials that can be used for surface 21 are sheet metal, fiberglass, plastic, rubber, latex, glass, and others.

As an alternate to using a single vibrating surface along the perimeter of flow conduit 20, multiple surfaces can be employed and vibrated in conjunction with each other to more fully involve the perimeter of the flow conduit.

One unique consequence of the current invention is that the device can be inserted within a larger duct or in a free stream, and used to sample the flow rate of any size fluid stream. This type of arrangement is characteristic of an insertion type flow meter and thus allows the superior performance afforded by the current invention to be used as an insertion device in any size conduit or in an open stream.

Using the current invention as an insertion device as just described, can eliminate the need for a flow conduit. Accordingly, the sides and bottom of flow conduit 20 of FIG. 17 could be eliminated and the remaining portion positioned inside a duct or in a free stream to measure fluid flow past flexible surface 21. When thus used inside a duct as an insertion type flow meter, the resulting output flow signal can be calibrated proportional to the total mass flow rate being conveyed by the duct. If thus used in an open stream without the confining cross sectional area of a duct or flow conduit, the resulting output flow signal could be calibrated proportional to the fluid velocity.

Figure 53:
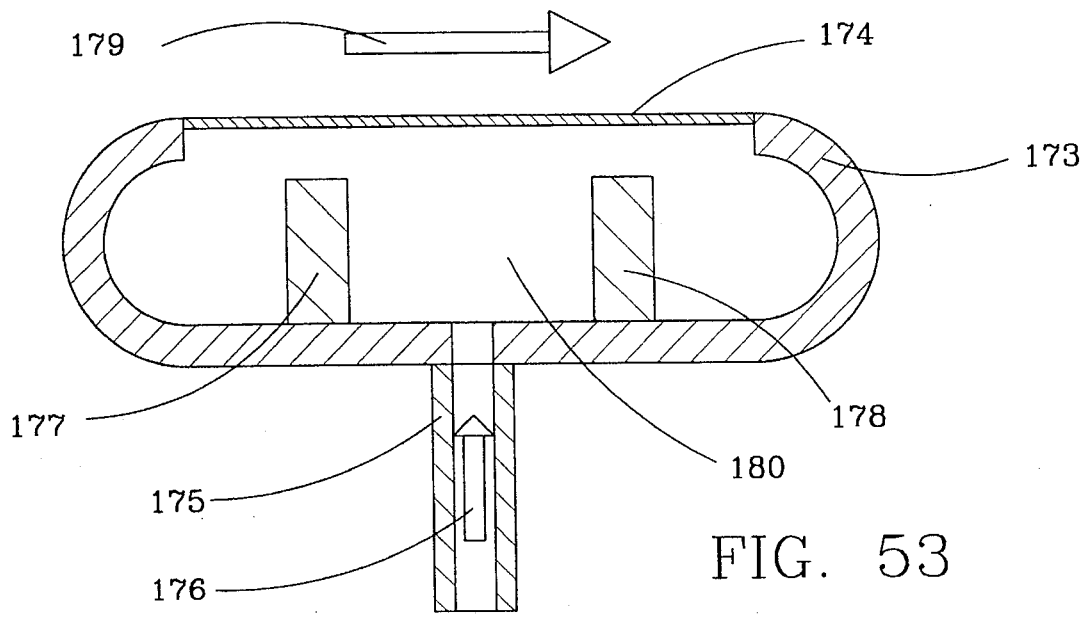
FIG. 53 is a cross sectional view of an exemplary embodiment of the present invention which can be employed as an insertion type flow meter for use in a duct or flow conduit, or in a free stream.

FIG. 53 shows an exemplary embodiment of the current invention which can be used as an insertion type flow meter inside a larger duct or flow conduit, or in a free stream. The operation of the embodiment of FIG. 53 is as follows.

Case 173 is a rigid housing which encloses motion detectors 177 and 178 within its internal cavity 180. Case 173 would preferably be made of strong, non-corrosive material such as stainless steel, and is aerodynamically or hydrodynamically designed so as not to create excessive drag forces or interfere with flowing fluid 179. Case 173 can be positioned at a specified location within a duct or in a free stream using bracket 175. Mounted in association with case 173 is flexible surface 174 which is preferable made of a flexible non-corrosive material such as stainless steel, titanium, quartz or the like.

Flexible surface 174 is caused to vibrate in an oscillatory manor by pulsating pressure 176, which is conveyed to cavity 180 via bracket 175. Flexible surface 174 can alternately be made to vibrate using electromagnetic drivers, electroded surfaces, actuators, and the like as was previously explained for other embodiments.

Figure 54:
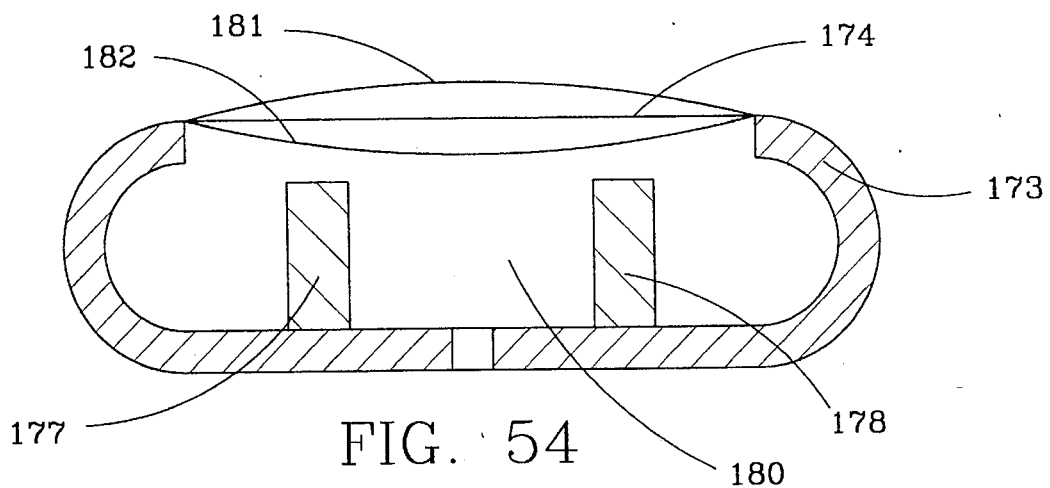
FIG. 54 is a view of the embodiment of FIG. 53 showing some exemplary vibratory shapes of its associated flexible surface.

Pulsating pressure 176 will thus cause flexible surface 174 to deflect similar to a diaphragm as shown in FIG. 54 where the cross sectional shape of the vibration of flexible surface 174 will oscillate from its maximum outward deflection 181 to its maximum inward deflection 182.

Figure 55:
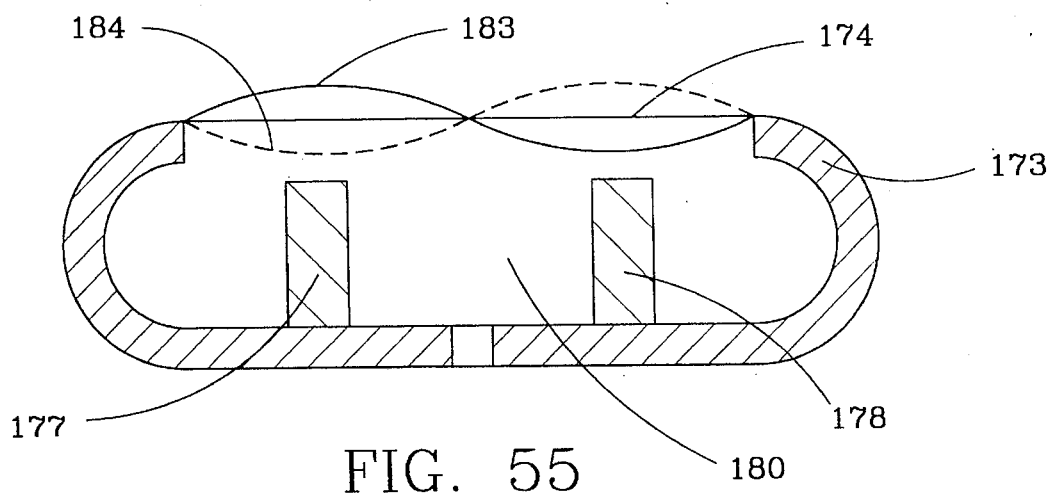
FIG. 55 is a view of the embodiment of FIG. 53 showing some exemplary deflected shapes of its associated flexible surface, due to Coriolis forces.

Fluid flow 179 interacting with flexible surface 174, will cause a Coriolis force distribution resulting in the deflection of flexible surface 174 into a shape 183 similar to that shown in FIG. 55, as it passes through its normally undeflected central position from its maximum outward deflection 181. As it again passes through its normally undeflected central position from its maximum inward deflection 182, flexible surface 174 will deflect into a shape 184 similar to that shown in FIG. 55.

These Coriolis induced deflections will then cause changes in the resulting signals from motion detectors 177 and 178 which are a function of the flow rate 179. These signal changes are analogous to those described for the embodiments of FIGS. 1 and 17, and can thus be processed in a similar manner.

As an alternate to the insertion type arrangement just described, it is anticipated that this embodiment can be incorporated into other entities, for example case 173 could alternately be the wing of an airplane, the body of a car, or the hull of a ship, with flexible surface 174 then being incorporated as a portion of the surface thereof, thus creating a meter which measures the velocity of the vehicle relative to its surrounding fluid.

Figure 22:
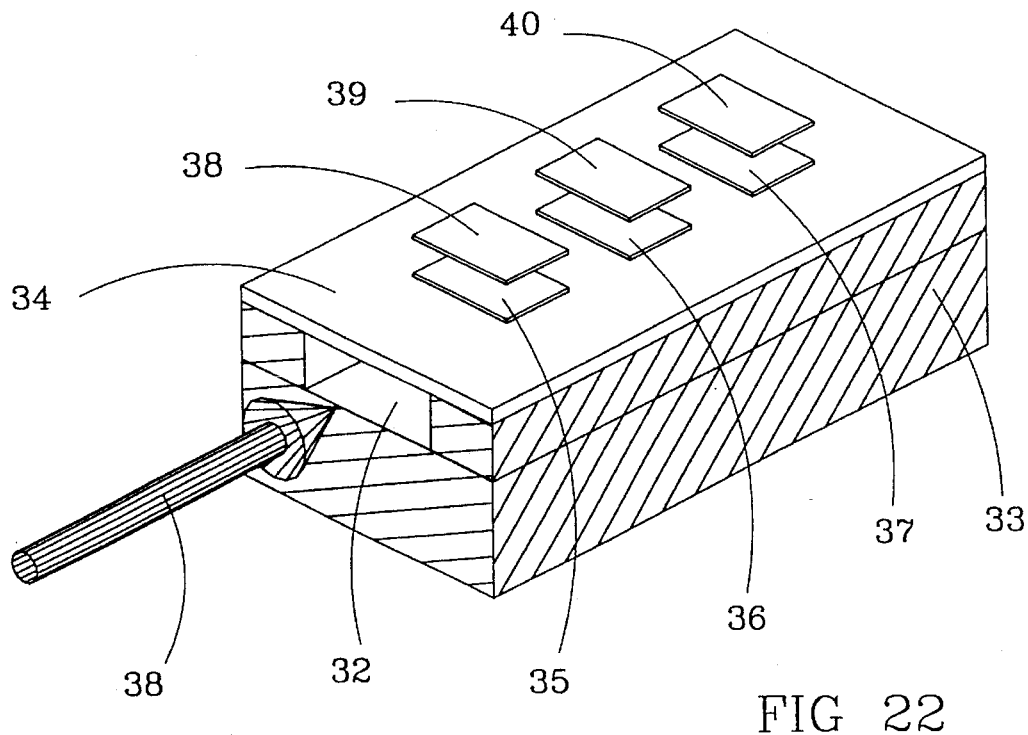
FIG. 22 is an alternate exemplary embodiment of the present invention employing a flow conduit that has several rigid sides and a flexible surface that is vibrated.

FIG. 22 depicts an alternate embodiment of the present invention described in Ser. No. 07/843,519 in which flow conduit 32 is etched or machined into semiconductor material 33, and covered with a flexible surface 34 on which is deposited electrodes 35, 36, and 37 positioned over flow conduit 32. Electrodes 38, 39, and 40 are positioned on a rigid surface (not shown) above and to interact with electrodes 35, 36, and 37, respectively. Electrode pair 36 and 39 are then electrically excited to force flexible surface 34 to vibrate similar to that shown in FIG. 18. Electrode pairs 35 and 38, and 37 and 40 are then used as capacitive motion detectors to sense the vibration of surface 34. In this configuration, the time relationship between the motion sensed at the fluid entry end of surface 34 will be delayed from the motion sensed at the fluid exit end of surface 34 by an amount that is functionally related to mass flow rate through the conduit. It is anticipated that the flexibility of surface 34 can be enhanced by etching or machining thinner or weak areas associated with it to facilitate flexing motion.

It is anticipated that the methods herein described for the present invention can be employed on flow conduits with many cross-sectional shapes including circular, oval, elliptical, convoluted, irregular, rectangular, polygonal, and others. In addition, the cross-sectional shape of a flow conduit can be permanently deformed along its length to enhance its flexing characteristics and thus its sensitivity to mass flow.

FIG. 25 depicts an alternate to the preferred exemplary embodiment using a unique arrangement of motion sensors and signal processing methods, the benefits and operation of which will now be described.

The embodiment of FIG. 25 consists of flow conduit 101 which is preferably made of a strong flexible non-corrosive material such as stainless steel, however other materials such as glass, titanium or others could also be used.

The ends of flow conduit 101 are formed into flexible joints 105 and 106 to reduce or eliminate axial stress affects. Flexible joints 105 and 106 could alternately be replaced by one or more individual joints such as commercially available bellows, multiple flared sections, a change in diameter, or slip joints similar to that shown in FIG. 24, or could simply be eliminated as shown in FIG. 40 since they are not required for the operation of the invention, but offer a degree of performance improvement.

Toward the ends of the straight center section of flow conduit 101 are stiffener rings 107 and 108 which are fixedly attached to flow conduit 101, preferably by brazing, to isolate the prescribed radial vibration to the area of flow conduit 101 between stiffener rings 107 and 108. Stiffener rings 107 and 108 are preferably made of a metallic material such as stainless or carbon steel.

In general, the purpose of stiffener rings 107 and 108 are to create a change in the stiffness of flow conduit 101 at specific locations along its length, and thereby isolate the primary radial vibration. Accordingly, stiffener rings 107 and 108 could be replaced by any means which causes a stiffness change in flow conduit 101 at specified locations, such as a change in the diameter or thickness of flow conduit 101, a change in the material of flow conduit 101, a formed upset, and others.

Accordingly, flexible joints 105 and 106 create a stiffness change at specified locations along the length of flow conduit 101, and thereby act as vibration isolation means without the need for stiffener rings 107 and 108. However, stiffener rings 107 and 108 offer a degree of performance increase and are therefore included in this embodiment.

Mounted in association with flow conduit 101 is temperature sensor 109 which is preferably a platinum resistance thermal device (RTD). Temperature sensor 109 is mounted so as to accurately measure the temperature of flow conduit 101 while not interfering with any prescribed mode of vibration. Accordingly, temperature sensor 109 is mounted on flow conduit 101 in the area of flexible joint 105 which is isolated from the radial vibration by stiffener ring 107. Circuit component 146 of FIG. 26 uses signals from temperature sensor 109 to produce signal 165 which represents the temperature of flow conduit 101, and is conveyed to circuit component 140 for further processing.

The ends of flow conduit 101 are fixedly attached to manifolds 102 and 103 by a welding or brazing process to form a gas tight rigid connection. As an alternate to the rigid connection shown in FIG. 25, FIG. 40 shows a method of terminating flow conduit 101 in a slip joint arrangement where a gas tight seal is maintained using seals 162 and 163. This arrangement eliminates axial stress effects from flow conduit 101 and thereby eliminates the need for flexible joints 105 and 106.

Figure 28:
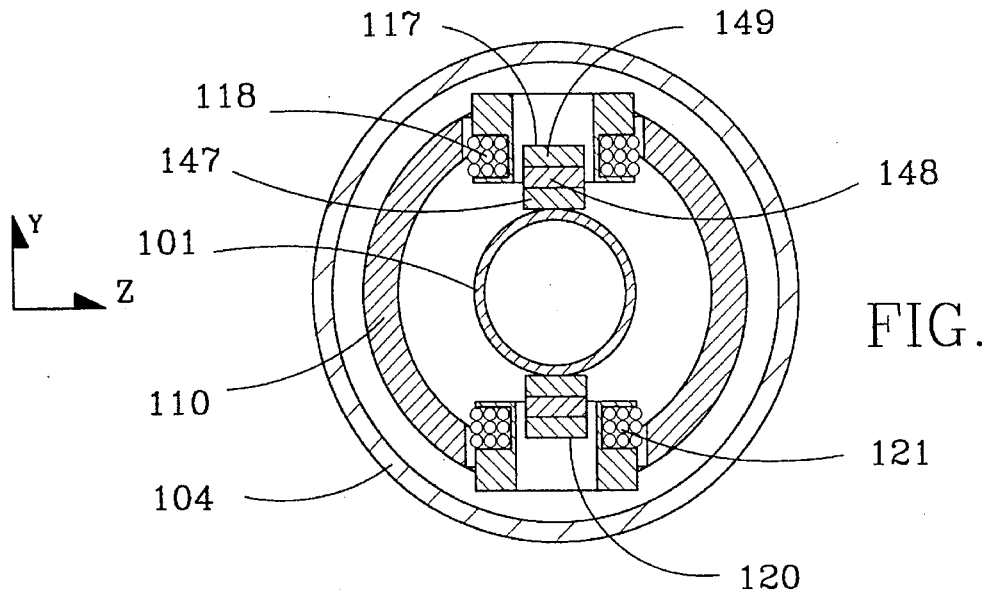
FIG. 28 is a cross sectional view through the motion drivers of the embodiment of FIG. 25.

Fixedly attached to flow conduit 101 and located approximately half way between stiffener rings 107 and 108 are drive magnets 117 and 120. FIG. 28 shows a cross sectional view through drive magnets 117 and 120 showing magnet 117 to be composed of a lower pole piece 147 fixedly attached to flow conduit 101 preferably by brazing, permanent magnet 148 fixedly attached to lower pole piece 147, and upper pole piece 149 fixedly attached to permanent magnet 148. Pole pieces 147 and 149 are preferably made of magnetically permeable material such as iron, High Permeability "49" or HyMu "80" by Carpenter Technology Corporation. Permanent magnet 148 is preferably made of samarium-cobalt or alnico magnetic alloys. Alternate materials for both permanent magnet 148 and for pole pieces 147 and 149 have been successfully tested or anticipated. Magnets 117 and 120 could alternately be single permanent magnets without pole pieces, electromagnets or the like. FIG. 28 also shows drive magnet 120 to be a combination of pole pieces and a permanent magnet similar to drive magnet 117. Therefore, any motion driving or sensing magnetic arrangement could be constructed from a combination of permanent magnet material and magnetically permeable material.

Drive magnets 117 and 120 are located diametrically opposite each other to facilitate driving two prescribed modes of vibration, of which, the primary mode is a two lobed elliptically radial vibration mode, with no reversals of the orientation of its cross sectional shape along the length of flow conduit 101. The secondary mode is a simple bending mode, as shall further be explained.

Figure 29:
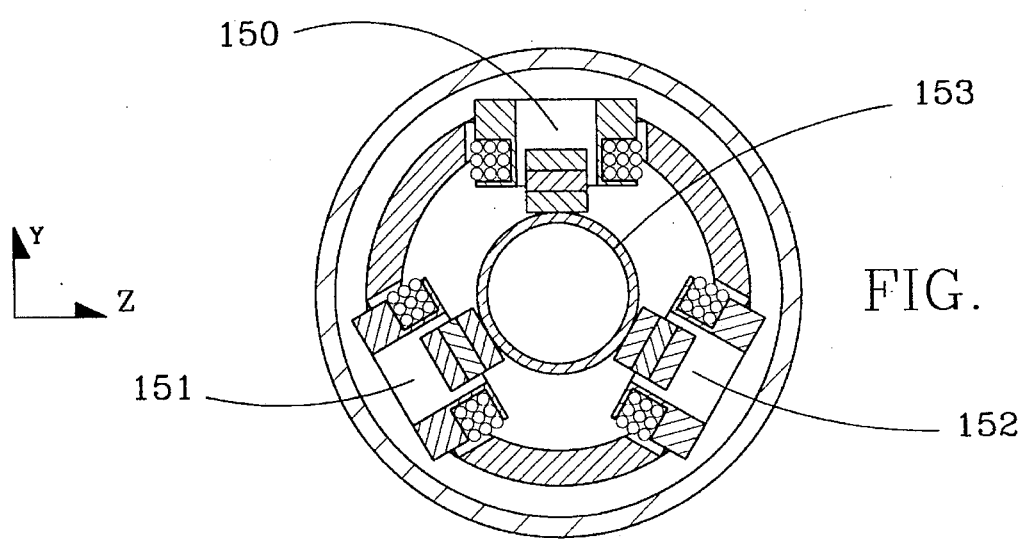
FIG. 29 is an alternate arrangement of motion drivers to that shown in FIG. 28, using three motion drivers instead of two.
Figure 30:
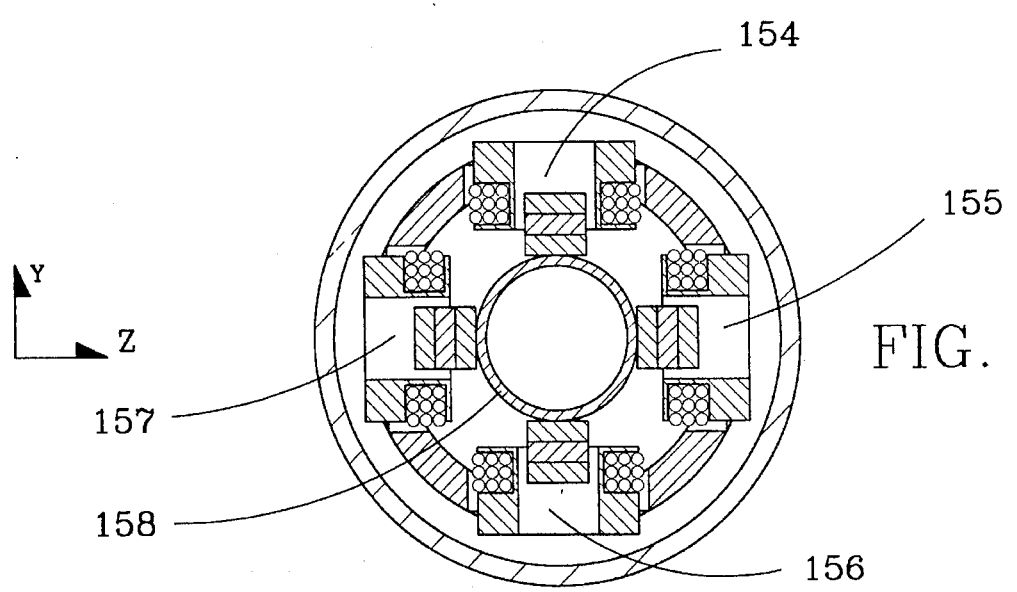
FIG. 30 is an alternate arrangement of motion drivers to that shown in FIG. 28, using four motion drivers instead of two.

For alternate prescribed modes of vibration, one or more drive magnets could be located at different locations along the length or around the circumference of flow conduit 101. For example, FIG. 29 shows an arrangement of three motion drivers 150, 151 and 152, mounted at intervals around the circumference of flow conduit 153. This arrangement would facilitate driving flow conduit 153 in a three lobed radial vibration such as depicted by FIG. 12, as well as a second radial or a bending mode of vibration as well. Alternately FIG. 30 shows four motion drivers 154, 155, 156 and 157 mounted at intervals around the circumference of flow conduit 158. This arrangement would facilitate driving flow conduit 158 in a two or four lobed radial vibration pattern such as depicted by FIGS. 10, 11 or 13 as well as a second radial or a bending mode of vibration as well.

Located part way between drive magnets 117 and 120, and stiffener ring 107, are pickoff magnets 111 and 114 which are fixedly attached to flow conduit 101, and are arranged in a diametrically opposite pattern similar to the drive magnet arrangement shown in FIG. 28.

Located part way between drive magnets 117 and 120, and stiffener ring 108, are pickoff magnets 123 and 126 which are fixedly attached to flow conduit 101, and are arranged in a diametrically opposite pattern similar to the drive magnet arrangement shown in FIG. 28.

As an alternate to the diametrically opposite arrangement of pickoff magnets as was just described, one or more pickoff magnets could be arranged at different intervals along the length and around the circumference of flow conduit 101 such as the patterns shown for drive magnets in FIGS. 29 and 30, and others.

Arranged in association with flow conduit 101 is support bracket 110 which is preferably made of non-magnetic material such as stainless steel. Support bracket 110 is not required for the operation of the invention however it facilitates design and manufacturing processes and is therefore included for practical reasons.

Fixedly attached to support bracket 110 are drive coils 118 and 121 which are arranged in association with drive magnets 117 and 120, respectively, to collectively form motion drivers 119 and 122, respectively.

Fixedly attached to support bracket 110 and arranged in association with pickoff magnets 111 and 114 are pickoff coils 112 and 115, respectively, which collectively form motion detectors 113 and 116, respectively.

Fixedly attached to support bracket 110 and arranged in association with pickoff magnets 123 and 126 are pickoff coils 124 and 127, respectively, which collectively form motion detectors 125 and 128, respectively.

Support bracket 110 can be designed to carry all or a part of any axial stress or force that may exist due to thermal expansion, pipeline or mechanical conditions. In addition, support bracket 110 can be used to facilitate wiring and interconnection of any electrical components, and to facilitate testing of the assembly prior to the addition of any case. Many different embodiments for support bracket 110 are therefore anticipated including metallic pipe, tubing, square tubing, molded plastic, welded brackets and others.

Enclosing the embodiment of FIG. 25 is case 104 which is fixedly attached to manifolds 102 and 103. Case 104 is not required for the operation of the invention however it can provide a number of useful features such as (1) protection of components from ambient conditions, (2) containment for fluid 129 in the event of a leak, (3) containment of a prescribed amount of pressure or vacuum, (4) conveyance of purge gas to and from specified components, (5) conveyance of any axial stress or forces that may exist due to thermal expansion, pipeline or mechanical conditions, and others. Case 104 is preferably made of a strong corrosion resistant material such as stainless steel pipe or sheet metal, and is fixedly attached to manifolds 102 and 103 by a welding or brazing process to form a pressure tight seal.

Case 104 could alternately be mounted using a slip joint arrangement such as O-ring seals 171 and 172, between case 104 and manifolds 102 and 103 as shown in FIG. 40. This alternate arrangement could be used to eliminate axial stress or forces from being transmitted through case 104, to allow for easy removal of case 104 for inspection, or other purposes.

Mounted in association with case 104 is feed-through 160 which allows for the conveyance of signals through the wall of case 104 via signal carriers 161. Feed-through 160 is preferably a hermetically sealed header however it could alternately be a ceramic, potted epoxy, or other type feed-through. A feed-through is not required for the operation of the device however its inclusion enhances certain design parameters and is therefore included for practical reasons.

The operation of the present invention according to the alternate exemplary embodiment of FIG. 25 shall now be described.

Figure 26:
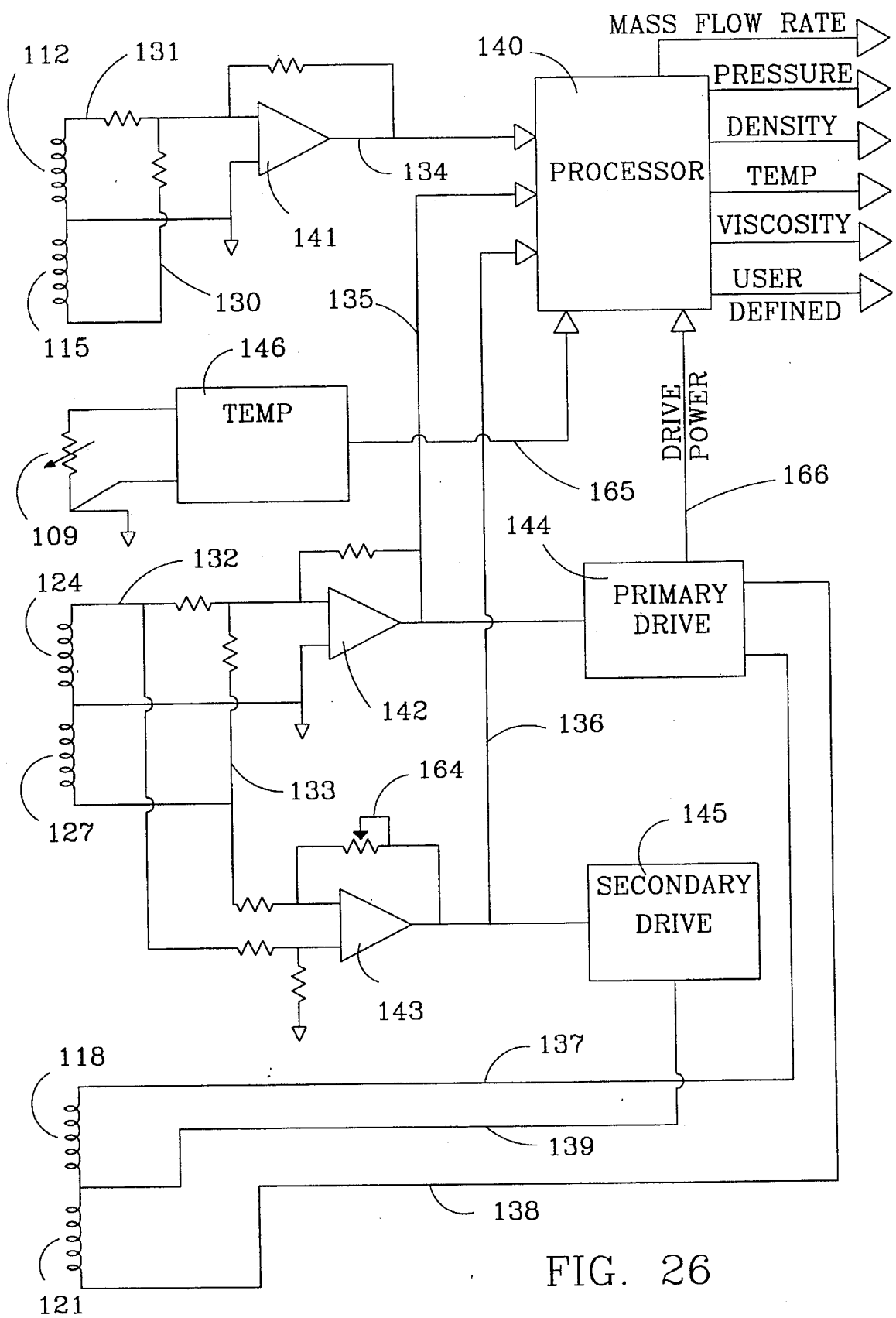
FIG. 26 is a block diagram of one possible configuration of circuit components used to measure the mass flow rate of fluid and other parameters according to the present invention.
Figure 27:
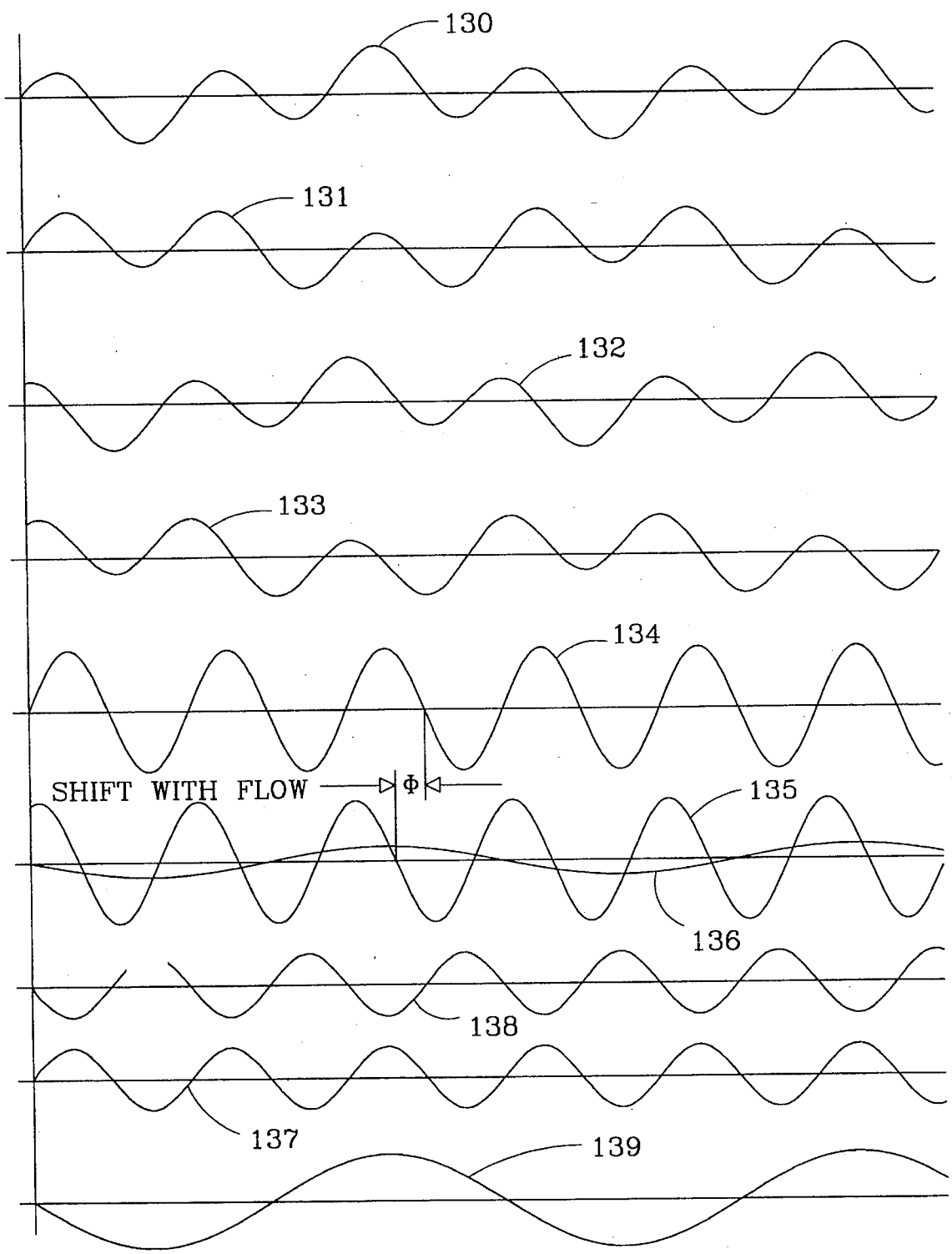
FIG. 27 is a representation of various wave forms that can be attained at various points in the circuit of FIG. 26.

Referring to FIGS. 25, 26 and 27, fluid 129 enters the device via manifold 102 as shown in FIG. 25. Next, fluid 129 enters flow conduit 101 and passes through flexible joint 105, through the center section of flow conduit 101, through flexible joint 106, and finally leaves the device via manifold 103. It is understood that the device operates equally well with flow in either direction, therefore fluid 129 could alternately flow in the opposite direction to that shown.

Figure 31:
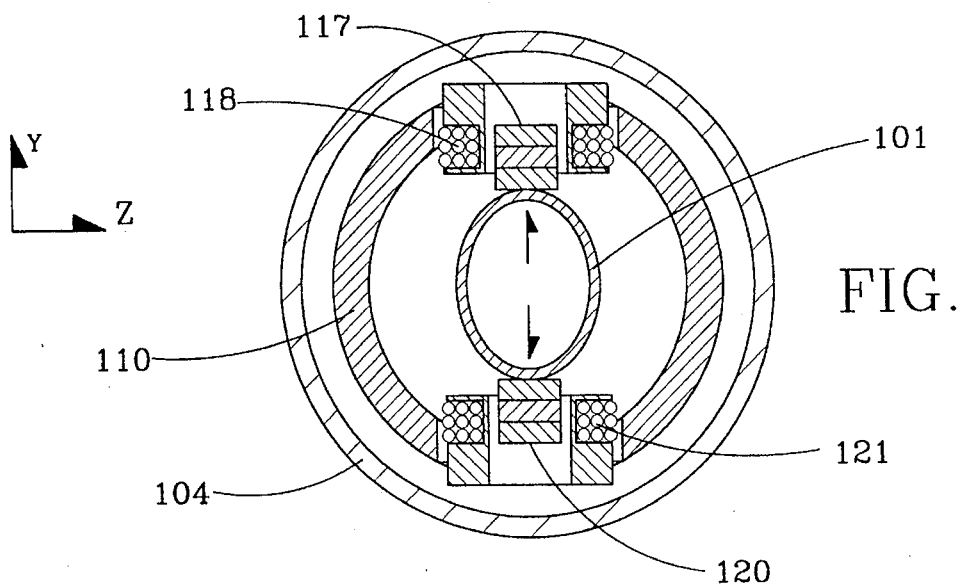
FIG. 31 is a representation of the primary radial vibration motion induced by the motion drivers on the embodiment of FIG. 25, at a point in time when the flow conduit is elliptically elongated in the vertical direction.
Figure 32:
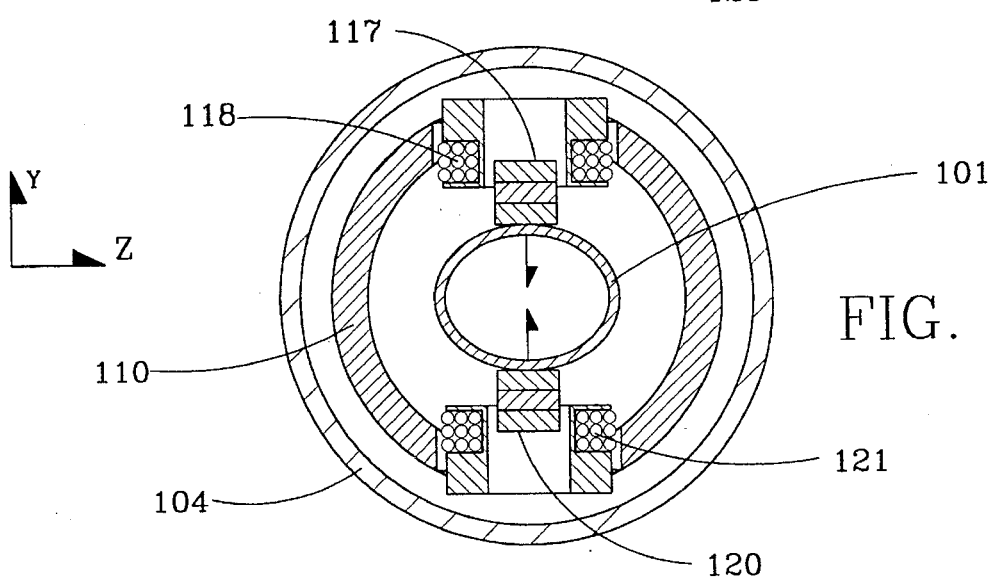
FIG. 32 is a representation of the primary radial vibration motion induced by the motion drivers on the embodiment of FIG. 25, at a point in time when the flow conduit is elliptically elongated in the horizontal direction.
Figure 33:
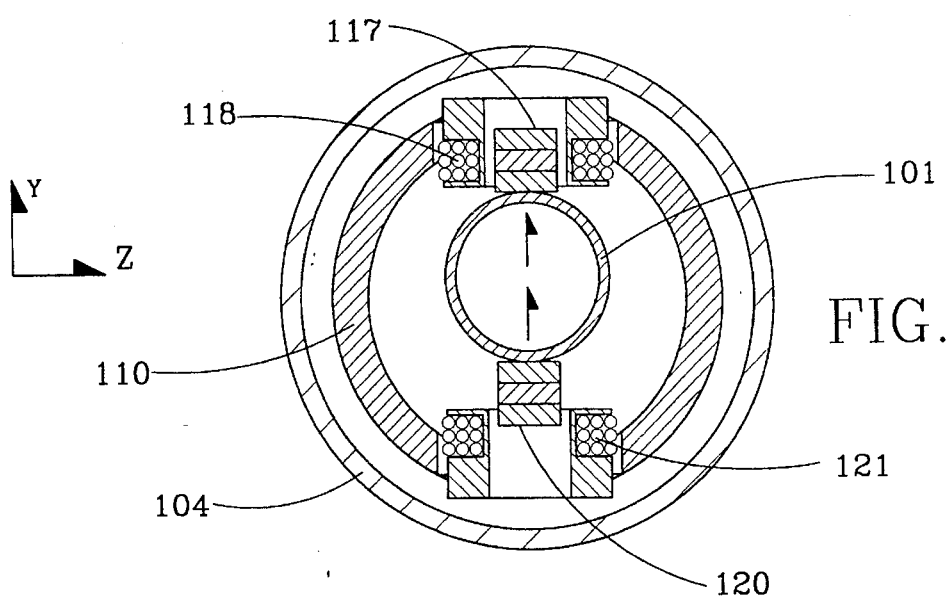
FIG. 33 is a representation of the secondary bending vibration motion induced by the motion drivers on the embodiment of FIG. 25, at a point in time when the flow conduit is vertically deflected above its center position.

Drive coils 118 and 121 are electrically excited in series fashion, as shown in FIG. 26, by signals 137 and 138, at a prescribed frequency and phase, from circuit component 144, to produce oppositely directed forces on drive magnets 117 and 120, respectively, thus causing the primary two lobe elliptical mode of vibration similar to that shown in FIGS. 31 and 32. Concurrently, drive coils 118 and 121 are electrically excited in parallel fashion from their center connection, at a prescribed frequency and phase, by signal 139 from circuit component 145, to produce similarly directed forces on drive magnets 117 and 120, respectively, as shown in FIG. 33, thus causing a bending mode of vibration similar to that shown in FIG. 41.

Figure 34:
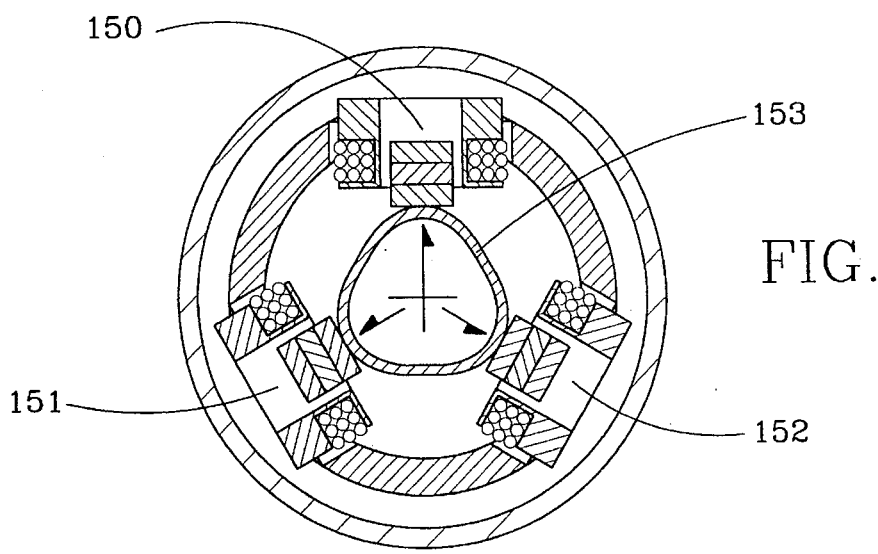
FIG. 34 is a representation of the primary radial vibration motion that could be induced by the three motion driver arrangement of FIG. 29, at a point in time when the motion drivers have reached their maximum radial excursion.
Figure 35:
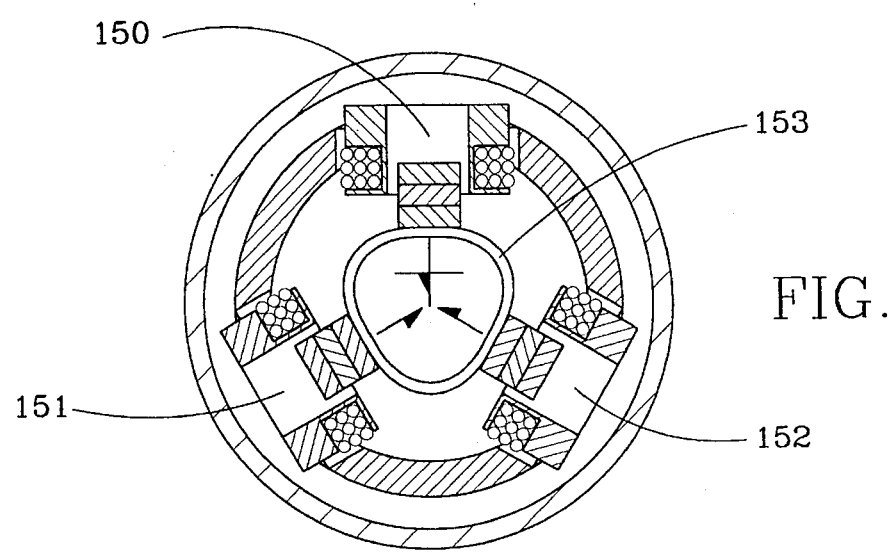
FIG. 35 is a representation of the primary radial vibration motion that could be induced by the three motion driver arrangement of FIG. 29, at a point in time when the motion drivers have reached their minimum radial excursion.
Figure 36:
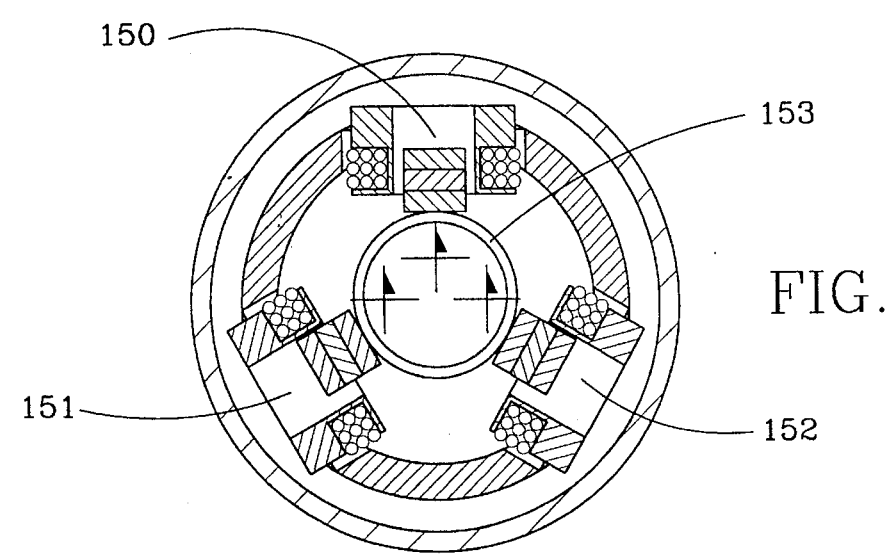
FIG. 36 is a representation of the secondary bending vibration motion that could be induced by the three motion driver arrangement of FIG. 29 at a point in time when the flow conduit is vertically deflected above its center position.

As an alternate to using a two lobed elliptical radial mode of vibration as just described, a three lobed radial mode could be used for either the primary or the secondary drive mode by using a similar technique of connecting and exciting motion drivers 150, 151 and 152 of FIG. 29, at the appropriate frequencies and phases to produce the three lobed radial mode as shown in FIGS. 34 and 35, and/or the bending mode shown in FIG. 36.

Figure 37:
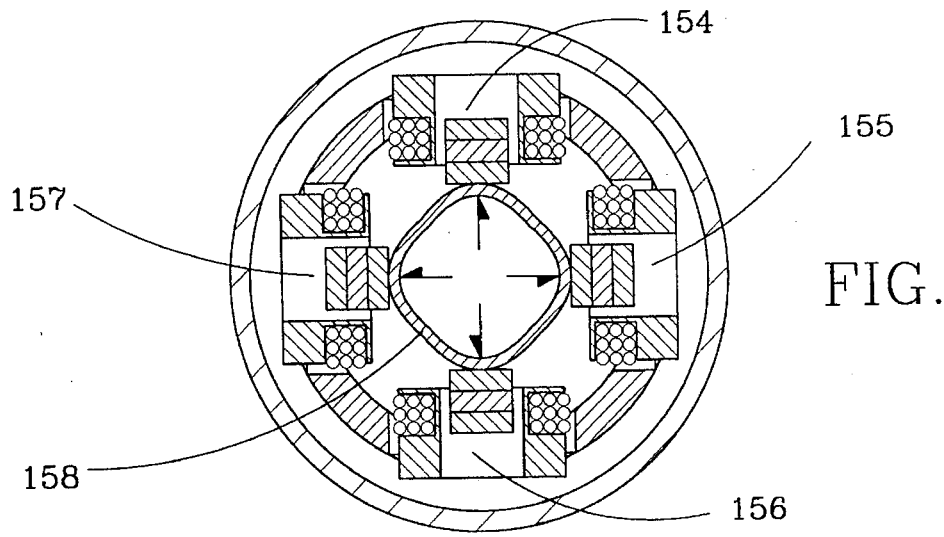
FIG. 37 is a representation of the primary radial vibration motion that could be induced by the four motion driver arrangement of FIG. 30, at a point in time when the motion drivers have reached their maximum radial excursion.
Figure 38:
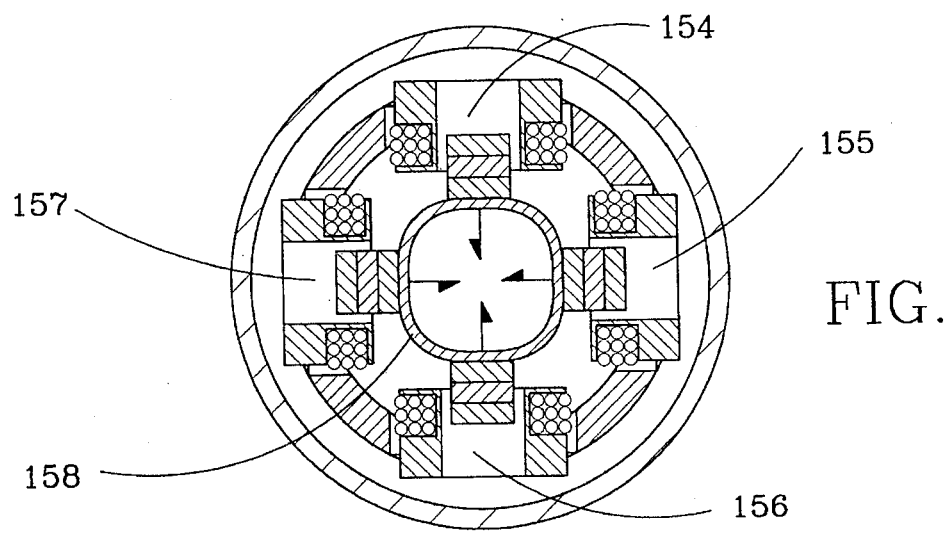
FIG. 38 is a representation of the primary radial vibration motion that could be induced by the four motion driver arrangement of FIG. 30, at a point in time when the motion drivers have reached their minimum radial excursion.
Figure 39:
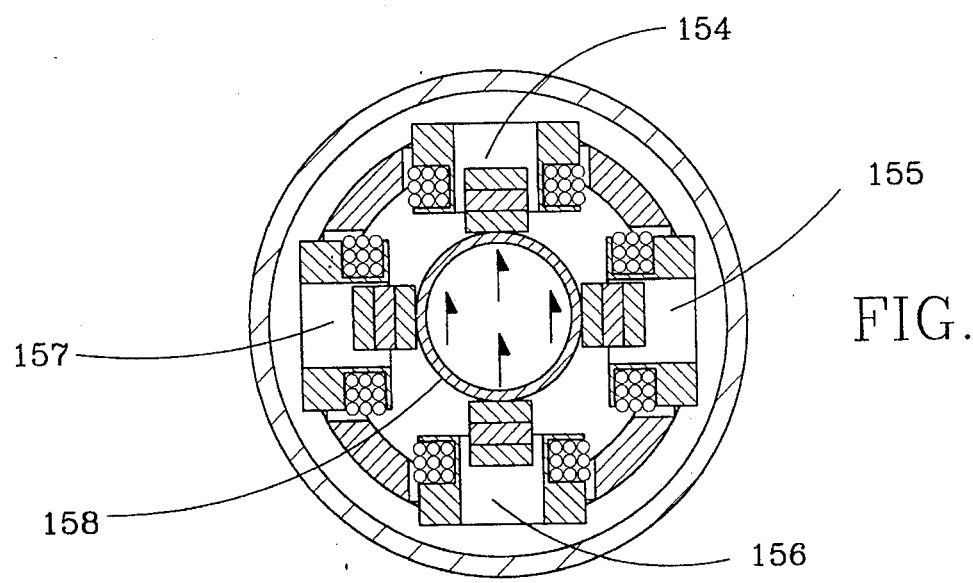
FIG. 39 is a representation of the secondary bending vibration motion that could be induced by the four motion driver arrangement of FIG. 30, at a point in time when the flow conduit is vertically deflected above its center position.

As another alternate to using a two lobed elliptical radial mode of vibration as previously described, a four lobed radial mode could be used for either the primary or the secondary drive mode by using a similar technique of connecting and exciting motion drivers 154, 155, 156 and 157 of FIG. 30, at the appropriate frequencies and phases to produce the four lobed radial mode as shown in FIGS. 37 and 38, and/or the bending mode shown in FIG. 39. It is therefore understood that many possible combinations of radial and/or bending modes of vibration can be utilized by appropriate instrumentation and excitation of the flow conduit.

In addition to using radial modes of vibration with no reversal in the orientation of their cross sectional shape along the length of flow conduit 101 as just described, either the primary or the secondary mode of vibration could utilize a radial mode of vibration whereby the orientation of the cross sectional shape changes along the length of flow conduit 101, one or more times, as was previously described for the embodiment of FIG. 1.

Once the requisite modes of vibration are established on flow conduit 101, pickoff coils 112, 115, 124 and 127 will produce signals 131, 130, 132 and 133, respectively, each of which represents the vibratory motion of flow conduit 101 at their coil's particular location, and will thus be a combination of both the primary and secondary frequencies as shown in FIG. 27.

Circuit component 141 combines signals 130 and 131 to produce signal 134 which represents the sum of signals 130 and 131. By arranging coils 112 and 115 so that the oppositely directed motion of FIGS. 31 and 32 will produce in-phase signals on coils 112 and 115, and the similarly directed motion of FIGS. 33 and 41, will produce out-of-phase signals on coils 112 and 115, the sum signal 134 will essentially represent only the primary radial mode component of the motion at the location of coils 112 and 115.

Since pickoff coils 112 and 115 will, as a practical matter, usually not produce signals 131 and +130 of identical amplitude, this unique method reduces the amount of secondary frequency component on signal 134 by a large amount as can be seen by the following example.

If the primary motion produces a signal 131 of 1 volt amplitude from coil 112, and as previously explained, the secondary amplitude is held to a minimum value only as necessary to determine pressure and density, for instance 10% of the primary signal, then signal 131 could be mathematically expressed as follows;

$$\text{Signal } 131 = 1 * \sin(L_1 * t + D_1) + 0.1 * \sin(L_2 * t + D_2) \qquad (2)$$

Where ($L_1$) and ($L_2$) represent the primary and secondary frequencies, respectively, in radians/sec, (t) represents time, and ($D_1$) and ($D_2$) represent the phase or time shift of the primary and secondary signals due to mass flow rate.

If coil 115 produces a signal 130 which is for example 10% larger amplitude for a given motion than corresponding signal 131, then signal 130 can be mathematically expressed as follows:

$$\text{Signal } 130 = 1.1 * \sin(L_1 * t + D_1) - 0.11 * \sin(L_2 * t + D_2) \qquad (3)$$

This 10% error could be caused by a mismatch in the magnetic field strengths produced by magnets 111 and 114, by a mismatch in the number of turns of wire on coils 112 and 115, a mismatch in components preceding circuit component 141, or other reasons.

The sum signal 134 would then be mathematically expressed as follows:

$$\text{Signal } 134 = 2.1 * \sin(L_1 * t + D_1) - 0.01 * \sin(L_2 * t + D_2) \qquad (4)$$

Thus yielding a primary to secondary amplitude ratio in sum signal 134 of 210/1, a reduction of 21 times the original 10% error.

Signal 134 is then conveyed to circuit component 140 for further processing.

The second term of equation (4) contains a phase shifted term ($D_2$) proportional to mass flow rate and could therefore be used to measure mass flow rate. However, doing so would constitute operating a single tube in a bending mode without counter balance means and would therefore not exhibit the tremendous performance enhancement afforded by the present invention.

A similar method is employed to combine signals 132 and 133, from pickoff coils 124 and 127, respectively, using circuit component 142, to make signal 135 which represents the sum of signals 132 and 133. Similar to signal 134, signal 135 represent the oppositely directed motion and thus the primary radial motion of flow conduit 101 at the location of pickoff coils 124 and 127.

Signal 135 is then conveyed to circuit component 140 for further processing, and additionally is conveyed to circuit component 144 to complete the drive servo loop for the primary radial mode vibration.

Circuit component 144 uses amplitude and phase information from signal 135 and produces signals 137 and 138 at appropriate amplitudes and phases to maintain the primary radial mode vibration at a prescribed level.

Additionally, signals 132 and 133 are combined by circuit component 143 to produce signal 136 which represents the difference between signals 132 and 133.

Figure 41:
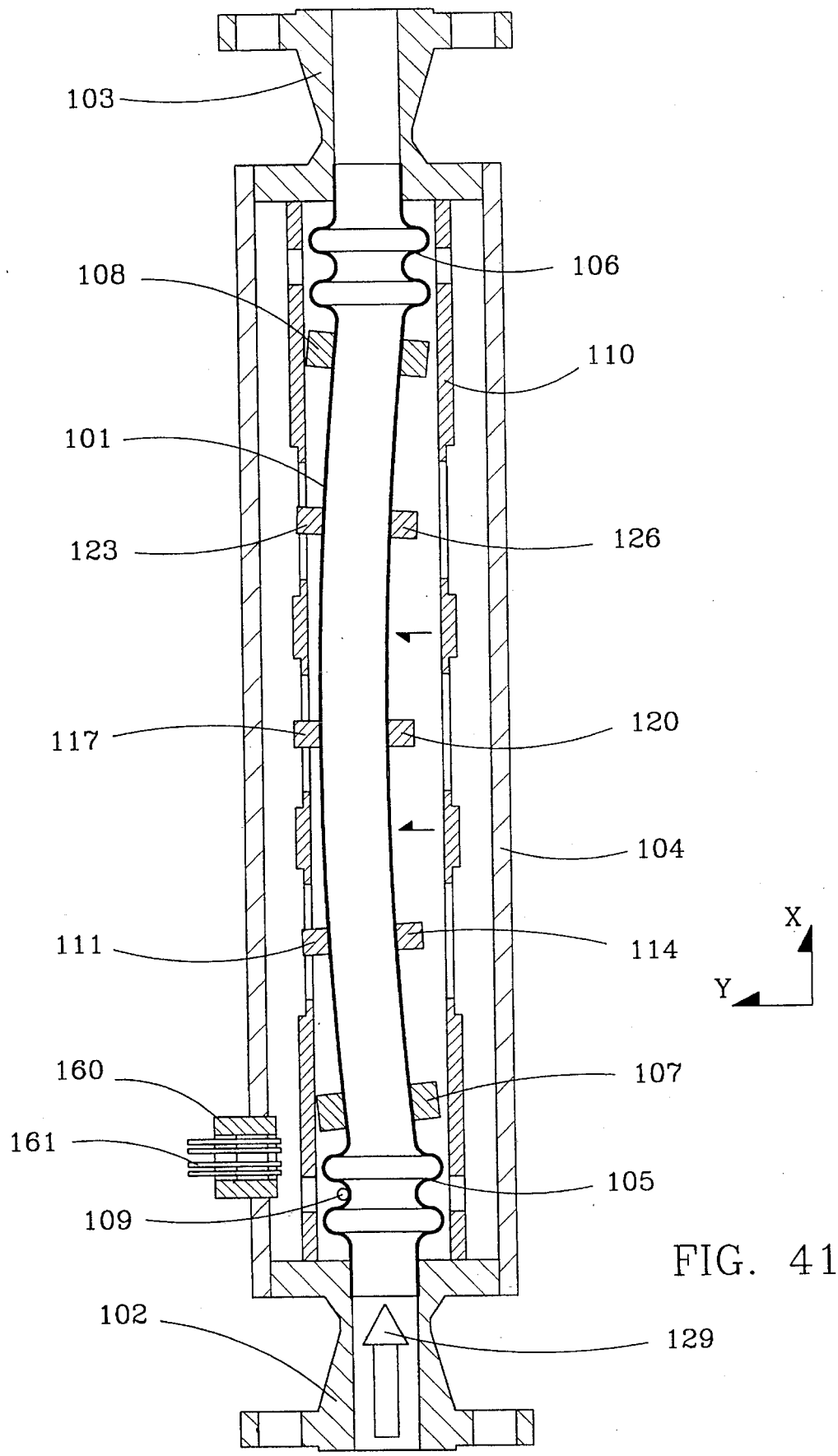
FIG. 41 is a exemplary representation of the embodiment of FIG. 25 showing the flow conduit deflected in its secondary bending mode of vibration. The coils have been removed and the magnitude of the deflection greatly exaggerated for clarity.

Since, as previously explained, the sum signal 135 of the pickoff signals 132 and 133 represents the oppositely directed motion and thus the primary radial mode of vibration, the difference signal 136 represents the similarly directed motion and thus the secondary bending mode of vibration as shown in FIGS. 33 and 41.

Using the previous example's value of a 10% difference between pickoff signal amplitudes, signals 132, 133, 135 and 136 can be mathematically described as follows:

$$\text{Signal } 132 = 1 * \sin(L_1 * t - D_1) + 0.1 * \sin(L_2 * t - D_2) \qquad (5)$$

$$\text{Signal } 133 = 1.1 * \sin(L_1 * t - D_1) - 0.11 * \sin(L_2 * t - D_2) \qquad (6)$$

$$\text{Signal } 135 = 2.1 * \sin(L_1 * t - D_1) - 0.01 * \sin(L_2 * t - D_2) \qquad (7)$$

$$\text{Signal } 136 = -0.1 * \sin(L_1 * t - D_1) + 0.21 * \sin(L_2 * t - D_2) \qquad (8)$$

Equation (7) shows the identical result for amplitude to that obtained in the earlier example of equation (4) since the same exemplary error value of 10% was used for both cases, thus a nearly pure sinusoidal signal 135 is obtained by summing signals 132 and 133.

However, differential signal 136 represented by equation (8) shows a primary frequency component of 0.1 volts, in addition to the desired secondary vibration mode signal of 0.21 volts.

To facilitate further processing using differential signal 136, its primary frequency component can be reduced or eliminated by a number of methods.

For this embodiment, the method employed to reduce the primary frequency component on differential signal 136 is to arrange circuit component 143 as a differential operational amplifier including variable resistor 164 in its feedback loop. By adjusting variable resistor 164 to the appropriate value, differential signal 136 can be produced containing virtually no primary frequency component.

Other methods of reducing or eliminating the primary frequency component on differential signal 136 include matching of pickoff components to produce closely matched signal amplitudes, using a variable gain amplifier on one of signals 132 or 133 to match its corresponding signal, using filtering techniques, using a Fast Fourier Transform (FFT) and others.

Differential signal 136 is then conveyed to circuit component 140 for further processing and additionally to circuit component 145 to complete the secondary drive servo loop.

Circuit component 145 uses amplitude and phase information from signal 136 and produces signal 139 at the appropriate amplitude and phase to maintain the secondary vibration mode at a prescribed level.

Circuit component 140, uses signals 134, 135, 136, 165 and 166, and determines the mass flow rate, pressure, density, temperature, viscosity, and other user defined parameters of fluid 129, as shall now be explained.

Figure 46:
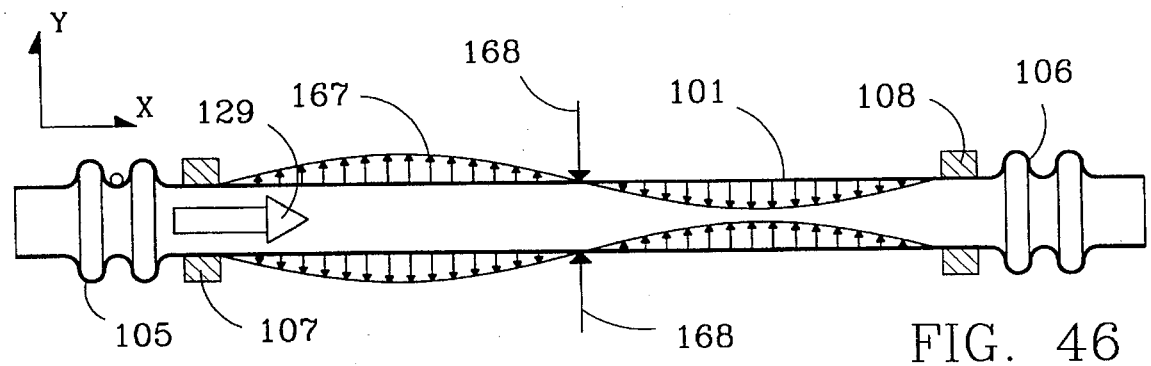
FIG. 46 is an exemplary representation of one possible Coriolis force distribution that could be developed in the X–Y plane on the embodiment of FIG. 25, taken at a point in time when the radial motion of the flow conduit is passing through its normally circular central position after having been elliptically elongated in the Y-direction.
Figure 47:
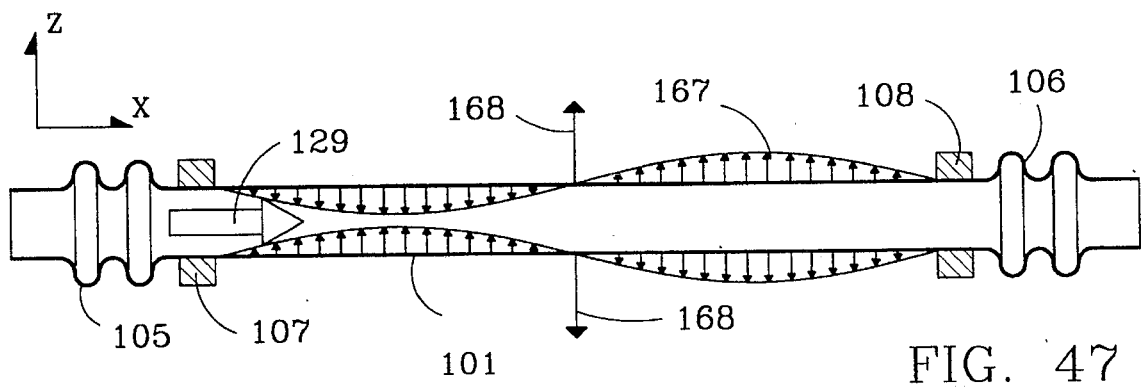
FIG. 47 is an exemplary representation of one possible Coriolis force distribution that could be developed in the X–Z plane on the embodiment of FIG. 25, taken at a point in time when the radial motion of the flow conduit is passing through its normally circular central position after having been elliptically elongated in the Y-direction.

Flowing fluid 129 interacting with the primary radial vibration of flow conduit 101, causes a Coriolis force distribution 167 along the wall of flow conduit 101 similar to that shown in FIGS. 46 and 47.

FIG. 46 shows a representative Coriolis force distribution 167 that could be developed in the X–Y plane of flow conduit 101 due to the combination of moving fluid 129 and radial motion 168, at the time when flow conduit 101 is passing through its normally circular central position. FIG. 47 shows a representative Coriolis force distribution 167 that could be developed concurrently with that shown in FIG. 46, but in the X–Z plane of flow conduit 101 due to combination of moving fluid 129 and radial motion 168, at the time when flow conduit 101 is passing through its normally circular central position.

Figure 48:
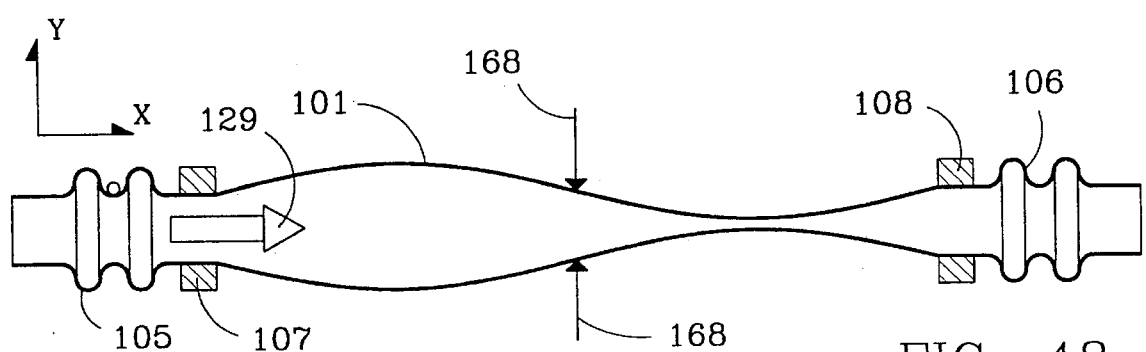
FIG. 48 is an exemplary representation of the general shape of flow conduit deflection in the X–Y plane due to the Coriolis force distribution shown in FIG. 46, where the magnitude of the deflection is greatly exaggerated for clarity.
Figure 49:
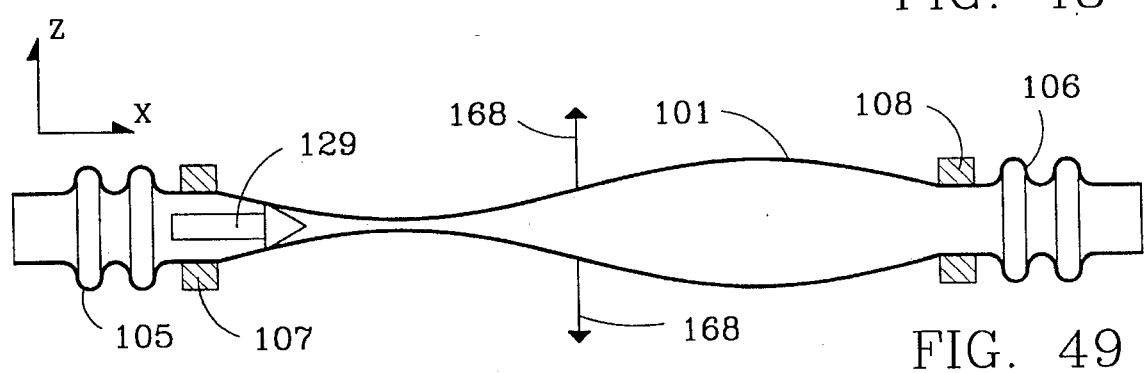
FIG. 49 is an exemplary representation of the general shape of flow conduit deflection in the X–Z plane due to the Coriolis force distribution shown in FIG. 47, where the magnitude of the deflection is greatly exaggerated for clarity.

Flow conduit 101 will then deflect into the general shape of Coriolis force distribution 167 as shown in FIGS. 48 and 49, where FIG. 48 is representative of the general shape of the deflection in the X–Y plane, and FIG. 49 is representative of the general shape of the deflection in the X–Z plane, both greatly exaggerated for clarity.

One measurable effect of the Coriolis force induced deflection of flow conduit 101 is a shift D in the time or phase relationship of both signals 134 and 135, functionally related to mass flow rate, as shown in FIG. 27. Signal 135 is seen to advanced in time while signal 134 is delayed in time due to mass flow rate. However, it is understood that alternate designs can reverse these phase relationships from those just described.

Each of signals 134 and 135 shift their time relationship with respect to a non-shifting reference such as drive signal 137 or 138, as a function of mass flow rate. Accordingly, each could individually be used to measure mass flow rate by comparing either signals 134 or 135 to a non-shifting reference. However, using the difference D between signals 134 and 135 doubles the available measurement and is thus preferable.

The amount of deflection of flow conduit 101 from a given Coriolis force distribution is related to the stiffness of flow conduit 101 and thus controls the sensitivity of the device to mass flow rate.

The stiffness and therefore the sensitivity of the device can change due to variations in the temperature, the pressure, and for certain designs the density of the process fluid. These parameters alter sensitivity by affecting, among other things, the elastic modulus, the stress, and the dynamic response of flow conduit 101, respectively. These and other process fluid parameters are therefore measured both to compensate the mass flow rate signal for sensitivity changes, and to supply the user with valuable additional information about the process fluid, as shall now be explained.

Figure 52:
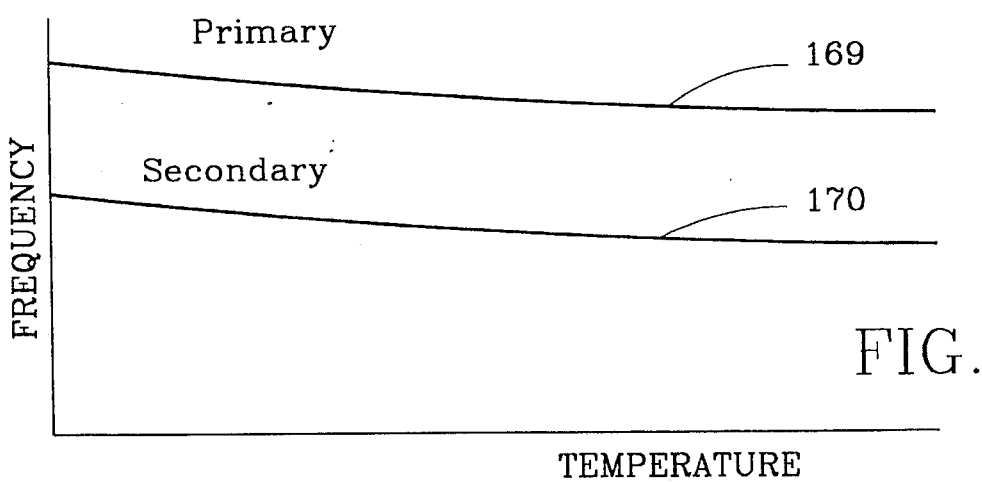
FIG. 52 is a graph of one possible functional relationship between flow conduit vibration frequency and process fluid temperature, for both the primary and secondary vibration modes, for the embodiment of FIG. 25.

FIGS. 50, 51 and 52 show graphs of possible representative variations of the primary frequency 169, and the secondary frequency 170, of flow conduit 101, as functions of pressure, density and temperature, respectively.

FIG. 50 shows that an increase in pressure can possibly cause an increase in the frequency of both the primary and secondary modes of vibration, by different amounts.

FIG. 51 shows that an increase in density can possibly cause a decrease in the frequency of both the primary and secondary modes of vibration, again by different amounts.

FIG. 52 shows that an increase in temperature can possibly cause a decrease in the frequency of both the primary and secondary modes of vibration, typically by similar amounts. This is typical for materials that exhibit a decrease in elastic modulus with an increase in temperature such as stainless steel or titanium.

As previously described, the mass flow rate passing through flow conduit 101 will be functionally related to (a) the time relationship between signals 134 and 135, (b) the stress in flow conduit 101 which will be functionally related to the pressure difference between the inside and the outside of flow conduit 101, (c) the elastic modulus of flow conduit 101, which will be functionally related to its temperature, and (d) the density of the process fluid. This functional relationship can therefore be defined as follows;

$$M'=f(D)*f(P)*f(D)*f(T)*f(L) \qquad (9)$$

Where M' represents mass flow rate, f(D) is the functional relation between mass flow rate and the time difference between signals 134 and 135, f(P) is a factor representing any change in the sensitivity of the device due to pressure, f(D) is a factor representing any change in the sensitivity of the device due to density, f(T) is a factor representing any change in the sensitivity of the device due to temperature, and f(L) is a factor representing a linearity correction.

Circuit component 140 of FIG. 26 uses signals 134, 135, 136 and 165 to determine the value of the factors in equation (9) and solve it for mass flow rate and other parameters as follows.

Circuit component 140 of FIG. 26 determines the time difference (D) between signals 134 and 135 by measuring the interval between each signals passing of a reference voltage, such as zero crossing, using a known reference such as a voltage ramp from an integrator circuit, counting the number of pulses from a clock source, or other methods such as Fast Fourier Transforms and the like. The value of the time difference (D) then represents the uncompensated mass flow rate signal.

Circuit component 140 then determines the pressure, density and temperature of the process fluid to both compensate the mass flow rate signal and to supply the user with this valuable additional information, as follows.

As shown on FIGS. 50, 51 and 52, the frequency for both the primary and the secondary vibrations typically vary as functions of pressure, density and temperature. One exception to this is when a material is used for flow conduit 101 which has a zero temperature coefficient of elastic modulus, such as Low Expansion 43-PH by Carpenter Technology Corporation, thus causing the frequencies to be independent of temperature. These graphs can be calculated or determined by calibration for a particular design.

A functional relation can therefore be developed mathematically defining each of the graphs in FIGS. 50, 51 and 52. These functional relations, along with primary frequency information from either of signals 134 or 135, secondary frequency information from signal 136, and temperature information from signal 165, are then used by circuit component 140 to determine the pressure and density of the process fluid. The frequencies of signals 134 or 135 and signal 136 are determined by measuring the cycle period using similar techniques to those previously described for measuring the time difference (D) between signals 134 and 135.

As a simplified example, the primary and secondary frequencies could have the following linear relationships, understanding however, that these relationships will normally not be simple linear relationships.

$$F_1=2000+2(P)-100(D)-0.2(T) \qquad (10)$$

$$F_2=800+1(P)-70(D)-0.1(T) \qquad (11)$$

Where:
$F_1$=Primary frequency in Hertz
$F_2$=Secondary frequency in Hertz
P=Pressure in pounds per square inch
D=Density in grams per cubic centimeter
T=Temperature in degrees Centigrade Since temperature (T) is determined independently by temperature sensor 109 and circuit component 146, and frequencies $F_1$ and $F_2$ are determined by circuit component 140, equations (10) and (11) therefore represent a system of two equations with two unknowns which is then solved by circuit component 140 thus determining both density and pressure. For the above example, if the temperature is for example 100° C., and the primary frequency is 2050 Hertz and the secondary frequency is 820 Hertz, then solving equations (10) and (11) yields a pressure of 47.5 pounds per square inch and a density of 0.25 grams per cubic centimeter.

Once pressure, temperature and density are thus determined, the uncompensated mass flow rate signal, as previously determined from time delay (D), can then be compensated by appropriate pressure, temperature and density factors as shown in equation (9).

In addition, equation (9) includes a linearity factor f(L) which can be used to correct non-linearities. For example, the relationship between time delay (D) and mass flow rate can be a function of the tangent of the phase angle shift of signals 134 and 135. This slight non-linearity can thus be corrected by circuit component 140 by making the factor f(L) in equation (9) a tangent function.

Circuit component 140 then supplies signals representing mass flow rate, pressure, density and temperature as outputs for the user, as shown in FIG. 26.

In addition, circuit component 140 can calculate process fluid viscosity as shall now be explained.

Circuit component 144 produces signals 137 and 138 which have the appropriate amplitudes and phases as necessary to maintain the primary vibration at a prescribed level as previously explained. Therefore by including appropriate circuitry within component 144, drive power signal 166 is produced which represents the power necessary to maintain the primary vibration level, and thus represents energy losses in the vibrating system.

One method of determining this power using component 144, is to measure the primary drive current supplied to coils 118 and 121. This current interacting with the magnetic fields of drive magnets 117 and 120 is therefore proportional to the primary drive force on flow conduit 101. Frequency and amplitude information from signal 135 can then be combined with this drive force information to produce drive power signal 166.

Since signal 166 represents the power necessary to maintain vibration level, it is functionally related to vibrational damping sources associated with the vibrating system. These sources include (a) viscous damping, functionally related to the viscosity of the fluid, (b) mechanical coupling causing vibrational energy loss to the surroundings due to vibrational imbalance, (c) acoustic coupling causing acoustic energy loss to the surroundings, (d) material damping losses from the material in flow conduit 101, and others.

Since acoustic and mechanical coupling, and material damping can be held to be negligible or constant, or can be measured, signal 166 will primarily be a function of viscous damping and thus the viscosity of the process fluid. Signal 166 can thus be used in conjunction with signals 135 and 165, by circuit component 140, to determine fluid viscosity which can then be supplied as an output to the user as shown in FIG. 26.

Circuit component 140 can also determine user defined output signals as necessary for the user such as volumetric flow rate, scaled conversions, net flow, percentage flow, and others such as steam quality and energy flow rate.

The previously described advantages of using two vibration modes to measure both pressure and density in addition to mass flow rate, can also be implemented on currently available bending mode type Coriolis mass flow meters as shall now be explained.

Figure 42:
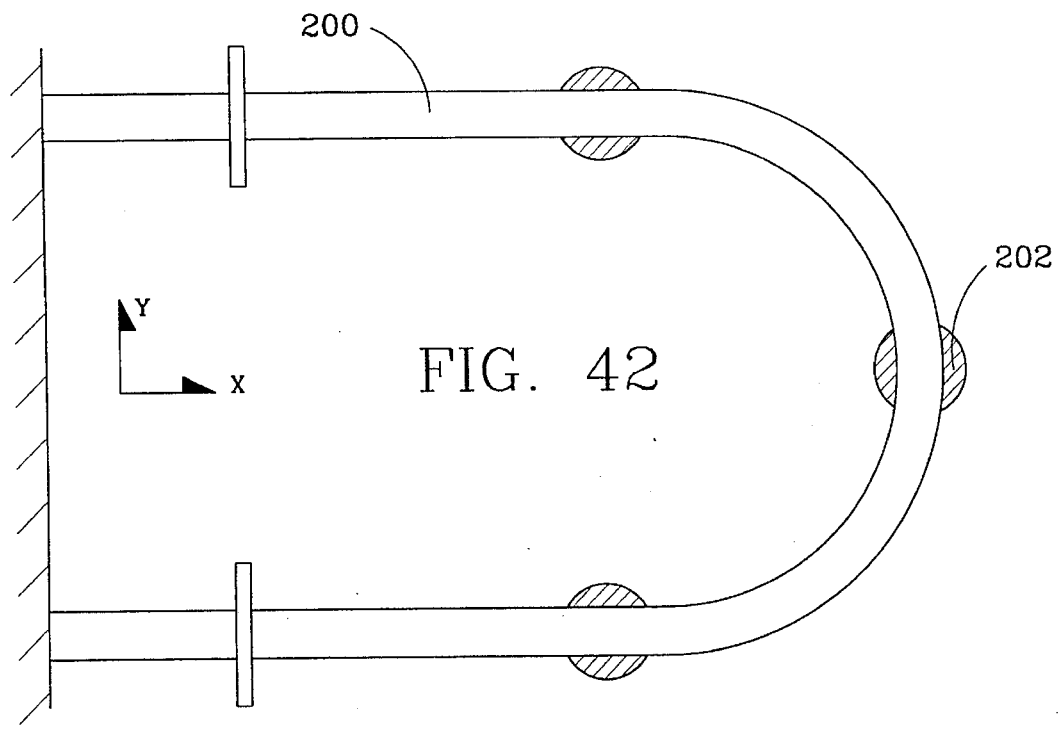
FIG. 42 is a representation of a parallel path Coriolis mass flow meter tube arrangement, viewed in the X–Y plane.
Figure 43:
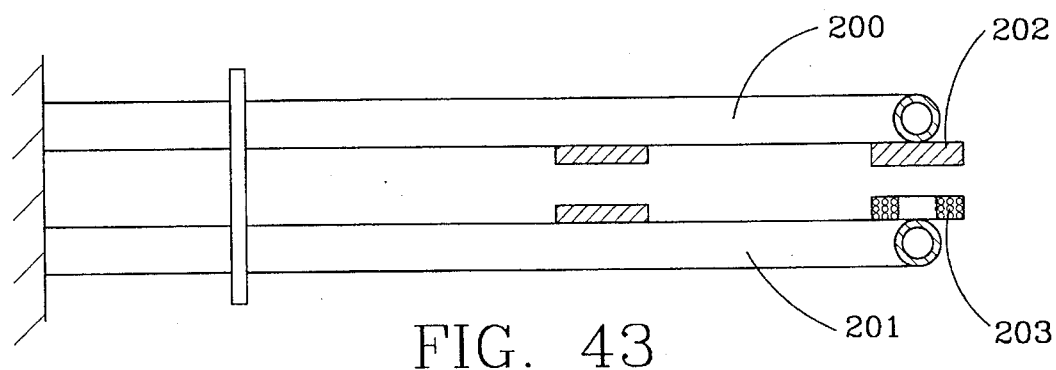
FIG. 43 is a cross sectional representation of the parallel path Coriolis mass flow meter tube arrangement shown in FIG. 42, viewed in the X–Z plane.

FIGS. 42 and 43 show two views of a traditional U-shaped parallel path Coriolis mass flow rate meter. Under normal operation, flow conduits 200 and 201 are vibrated in opposition to each other in a bending mode of vibration similar to the tines of a tuning fork. This can be accomplished by electrically exciting drive coil 203 in association with drive magnet 202, as necessary to produce the primary bending mode vibration.

By exciting drive coil 203 at a second frequency, flow conduits 200 and 201 can be made to simultaneously vibrate in a second mode of vibration, either bending or radial.

Figure 44:
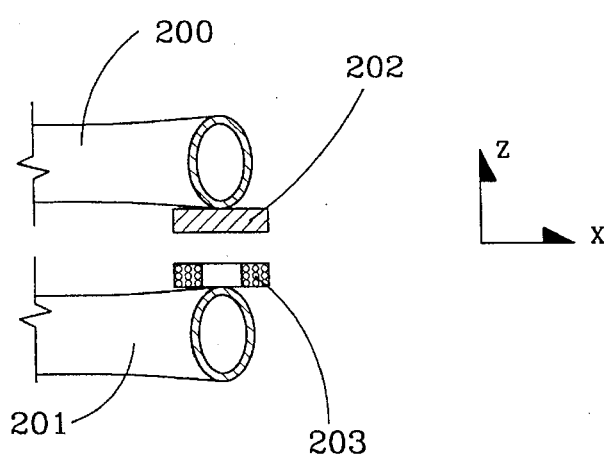
FIG. 44 is a close up view of the motion driver arrangement shown in FIG. 43 showing radial vibratory motion being imparted to both tubes, taken at a point in time when the tubes are elliptically elongated in the vertical direction.
Figure 45:
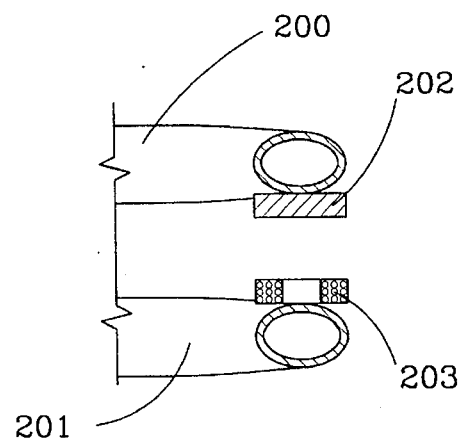
FIG. 45 is a close up view of the motion driver arrangement shown in FIG. 43 showing radial vibratory motion being imparted to both tubes, taken at a point in time when the tubes are elliptically elongated in the horizontal direction.

FIGS. 44 and 45 show two views of the cross section of flow conduits 200 and 201 being vibrated in an elliptically shaped radial vibration as a secondary vibration. Since a Coriolis flow meter of the embodiment of FIG. 42 would measure mass flow rate using traditional bending mode vibration techniques, it would not be necessary to use a radial mode of vibration for the secondary mode, thus any combination of bending or radial modes of vibration could be used for both the primary and the secondary modes with the restriction that the two modes must change frequency at different rates with pressure or density changes as previously explained.

For the embodiment of FIG. 43, drive coil 203 was used both for exciting the traditional primary bending mode vibration as well as a secondary vibration. It is understood however, that a second motion driver could be installed and used on any portion of either of tubes 200 or 201 as necessary to excite a second mode of vibration for pressure and density measurement.

FIGS. 44 and 45 show both flow conduits 200 and 201 being vibrated simultaneously in radial modes of vibration, however, it is understood that any portion of either flow conduit could be vibrated as necessary to create the requisite reference frequency to measure pressure and density.

The embodiments of FIG. 1, 25 and 40 include components such as platinum RTD's, permanent magnets, coils, metal pipes and parts, all of which can be made to withstand temperatures in excess of 1000° F. The current invention is therefore uniquely suited for high temperature applications.

One important high temperature application in which the benefits of the current invention could be used to great advantage is measuring steam. This has traditionally been difficult to measure due to its high temperature and due to the fact that in the saturated condition, three independent properties are required to uniquely specify the state of the gas. Since the current invention measures pressure, temperature and density, the quality of the steam and thus its state can be determined. In addition, since the mass flow rate is also known, the energy flow rate can be directly calculated from steam tables, thus creating an extremely valuable instrument for power plants and other industrial steam users.

The embodiments previously described involve the use of some type of flow conduit where either all or a portion of the conduit vibrates as necessary to create the requisite Coriolis forces. However, it is not necessary to envelope the fluid stream within a conduit to use the benefits of the current invention. Accordingly, the embodiment of FIG. 17 could be positioned within a larger duct or held in a free stream of moving gas or liquid.

Figure 56:
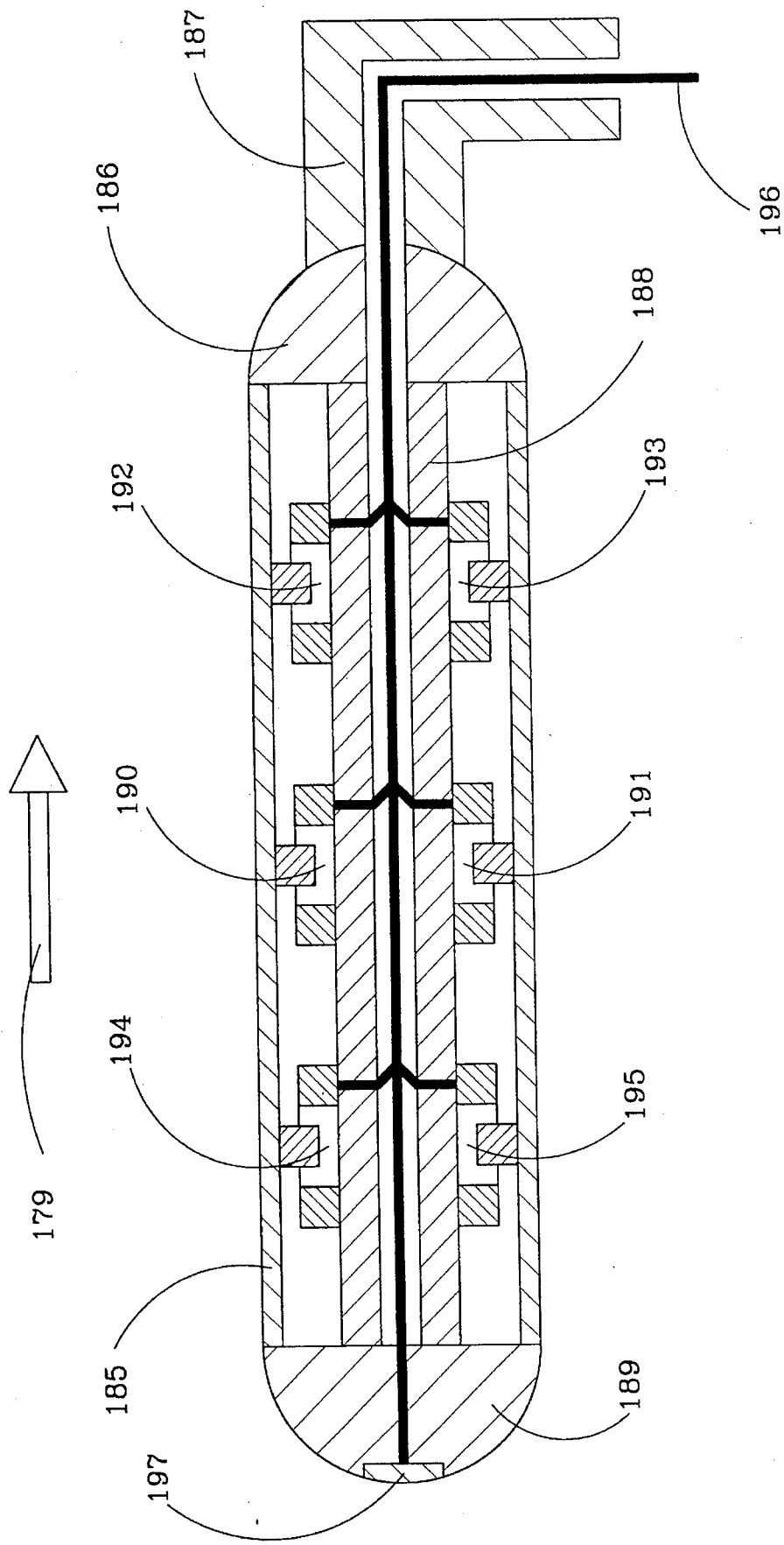
FIG. 56 is an alternate to the preferred embodiment which can be used as an insertion type device.

FIG. 56 is an embodiment of a Coriolis mass flow meter using many of the principles hereinbefore described, however the arrangement of elements in this embodiment cause several unique and advantageous characteristics which are not available from any currently available device. The principle advantage of the embodiment of FIG. 56 derives from the arrangement of a radially vibrating, axially symmetric closed surface 185 which is disposed in flowing fluid 179 such that the flow is parallel with the axis of surface 185, and flows over the outside of said surface. In this arrangement increasing fluid pressure surrounding the outside of surface 185 puts compressive stresses onto surface 185 which in turn increases the devices sensitivity to flow rate as pressure increases. This phenomenon is reversed from that of other embodiments with fluid flowing inside of a flow conduit. In addition, the change in the natural frequency as a function of pressure is also reversed in this arrangement since increasing exterior pressure around surface 185 will in turn cause a decrease in the natural frequency of the driven radial vibration. This effect can be advantageously applied for determination of pressure and density. Embodiments previously described with fluid flowing inside of a flow conduit such as in FIG. 1, present the designer with a tradeoff between sensitivity and pressure rating since higher internal pressures will require thicker tube walls and will induce higher tensile stresses both of which reduce the sensitivity of the device to measuring flow rate. Using the embodiment of FIG. 56, this phenomenon is reversed allowing the designer to advantageously design a device which actually improves its sensitivity to flow rate and pressure measurement as fluid pressure increases.

Surface 185 is preferably a cylindrical surface such as a tube or pipe made of a strong flexible material such as stainless steel, titanium, quartz, etc., although non-circular cross sectional shapes are also anticipated. The inside of surface 185 is instrumented with magnets while mounting bracket 188 is instrumented with coils forming magnet/coil pairs 190 through 195 which can excite or sense vibrations in surface 185 as previously described for other embodiments. Mounting bracket 188 can be attached at one or both of its ends to end caps 189 and/or 186, where attachment at only one end, or attachment through a flexible or slip type joint (bellows) eliminates any stresses along surface 185 due to any temperature difference between surface 185 and bracket 188. Surface 185 is rigidly mounted at its ends to end caps 189 and 186 which can be aerodynamically or hydrodynamically designed to enhance flow characteristics. Temperature sensor 197 is mounted in association with end cap 189 to monitor the temperature of flowing fluid 179, or can be mounted directly on surface 185 to monitor its temperature for compensation of elastic modulus changes. Signal carrier 196 conveys electrical signals between temperature sensor 197, magnet/coil pairs 190 through 195, and the signal processing electronics (not shown). Bracket 187 is used to mount the device and to protect signal carrier 196.

The annular space between mounting bracket 188 and surface 185 is preferably evacuated to a vacuum, or filled with a known amount of gas such as argon or nitrogen. There are two main methods of operation of the embodiment of FIG. 56 which differ from each other depending on the chosen type of signal processing. Each signal processing technique has its own advantages thereby allowing the designer to choose the appropriate one based on specific design requirements.

The first method described employees a phase or time measurement technique for signal processing. In this method, magnet/coil pairs 190 and 191 would be electrically excited to produce at least one and preferably two radial modes of vibration on surface 185 similar to that of tube 1 shown in FIGS. 2 through 4. With flowing fluid 179 going over the outside of surface 185, a Coriolis force distribution similar to that shown in FIG. 8 would result as surface 185 passes through its normally circular cross sectional shape. The resulting deflection of surface 185 from this Coriolis force distribution would then look similar in shape to tube 1 of FIG. 9. Magnet/coil pairs 194 and 195 would then sense a change in the vibratory motion of surface 185 said change being a shift in its time or phase relationship to the motion sensed by Magnet/coil pairs 192 and 193. Means for measuring the time or phase relationship change (not shown) between these two motions would then be employed to create a signal proportional to the rate of flowing fluid 179, functionally related to this time or phase relationship. As previously described for other embodiments, surface 185 can be excited in multiple modes of vibration and the changes in frequencies evaluated to thereby determine the density and the pressure of flowing fluid 179. In addition, as previously described for other embodiments, the power required to maintain the vibration of surface 185 is a function of the viscosity of flowing fluid 179. Therefore by measuring this power, a signal can be created proportional to fluid viscosity which can be used by the customer.

The second method of operation of the embodiment of FIG. 56 involves the use of an amplitude measurement technique for signal processing. In this method, magnet/coil pairs 190 and 191 would be electrically excited as previously described to produce at least one and preferably two radial modes of vibration on surface 185 similar to that of tube 1 shown in FIGS. 2 through 4. With flowing fluid 179 going over the outside of surface 185, a Coriolis force distribution similar to that shown in FIG. 8 would result as surface 185 passes through its normally circular cross sectional shape. The resulting deflection of surface 185 from this Coriolis force distribution would then look similar in shape to tube 1 of FIG. 9, which results in a change in the amplitude of the motion sensed by the upstream magnet/coil pairs 194, 195 versus the downstream magnet/coil pairs 192, 193. Since the phase of the motion sensed by magnet/coil pairs 194, 195 and 192, 193 is directly in phase for the driven motion, and directly out of phase for the flow induced motion, by subtracting the signals sensed by the upstream magnet/coil pairs 194, 195 from those of the downstream magnet/coil pairs 192, 193, the resultant detected driven motion will be canceled out leaving a signal that is 2 times the Coriolis induced motion, which is proportional to flow rate. This change in the amplitude measurement technique has several unique advantages over a change in the phase measurement techniques including designs using higher frequencies of vibration since higher frequencies generate larger signals in the magnet coil pickoffs, and in general customers of this technology prefer shorter tube designs which will cause higher frequencies. In addition, by increasing the amplitude of the driven motion, more Coriolis induced deflection is generated allowing for larger amplitude signals to be measured. By contrast, increasing the driven amplitude has no effect on the amount of phase or time delay generated by a given design. In addition, for certain driven modes of vibration there will be places on the tube where phase is invariant with flow rate thereby requiring the use of an amplitude type measurement technique to extract the flow rate information. For example, a mode shape similar to that of tube 1 in FIG. 9 can be excited and used as the driven radial mode on surface 185 of FIG. 56 by electrically exciting magnet/coil pairs 194, 195 and 192, 193 in the appropriate phases. In this case the center of the tube (magnet/coil pairs 190 and 191) would not translate during this driven vibration and no fluid flow. With increasing flowing fluid 179, a Coriolis force distribution similar to that shown in FIG. 21 will result causing deflections at the center of the tube proportional to flow rate, which will be sensed by magnet/coil pairs 190 and 191. These induced signals will be either 0° or 180° phase relationship depending on the direction of flowing fluid 179, and will not appreciably phase shift with changes in the magnitude of the flow rate. As previously described for other embodiments, surface 185 can be excited in multiple modes of vibration and the changes in frequencies evaluated to thereby determine the density and the pressure of flowing fluid 179. In addition, as previously described for other embodiments, the power required to maintain the vibration of surface 185 is a function of the viscosity of flowing fluid 179. Therefore by measuring this power, a signal can be created proportional to fluid viscosity which can be used by the customer.

As an alternate method, surface 185 can be driven in a radial mode of vibration as just described by electrically exciting magnet/coil pairs 194, 195 and 192, 193 in the appropriate phases resulting in a driven mode shape similar to that of tube 1 of FIG. 9. In this case, dual windings are employed on the coils of magnet/coil pairs 194, 195 and 192, 193, with one winding being used for driving the motion, and the other winding being used for sensing the motion. The sensing coils can then be added together as previously described to cancel the sensed driven motion and create a resultant signal that is 2 times the induced Coriolis deflection which in turn is proportional to flow rate. This arrangement eliminates the need for magnet/coil pairs 190 and 191 thereby reducing complexity and cost.

Figure 71:
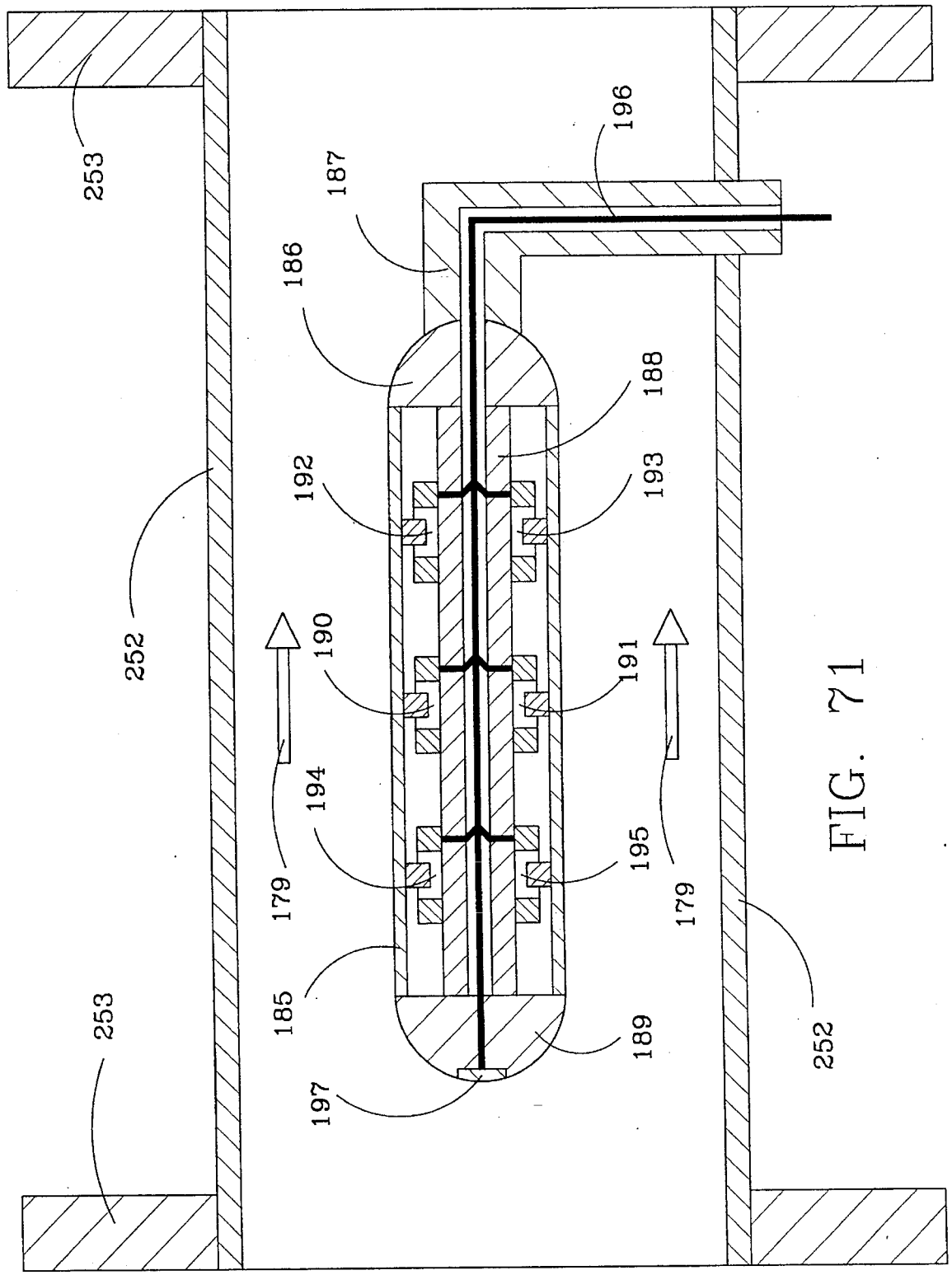
FIG. 71 is the embodiment of FIG. 56 mounted within a pipe.

In addition to the advantages previously described pertaining to the embodiment of FIG. 56, further advantages occur when this embodiment is mounted within a flow conduit. FIG. 71 shows the embodiment of FIG. 56 mounted within pipe 252 which includes pipe connections 253 at its ends thereby forming a short "spool-piece" which can easily be mounted in a pipe line. In this arrangement flowing fluid 179 passes in the annular space between surface 185 and pipe 252. This arrangement has the advantageous characteristics of reducing velocity profile effect, reducing the power required to measure a given size fluid stream, greatly increases the practical size limit for which this technology can be used, and eliminates pipeline induced stresses, as will later be described in detail.

Figure 57:
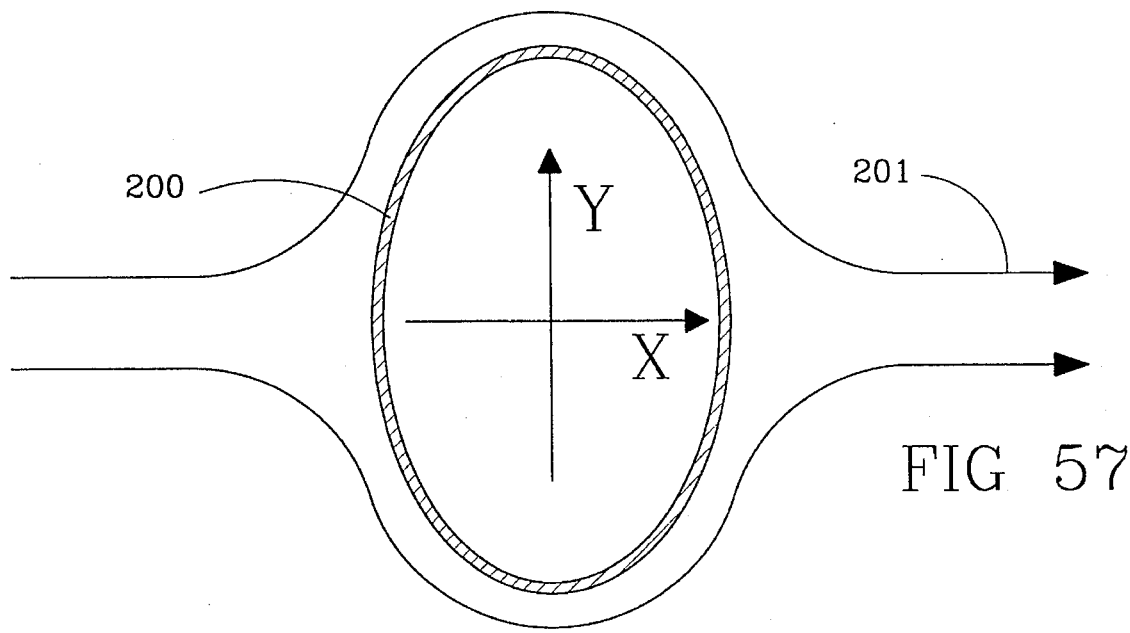
FIG. 57 is a cross sectional view of a flow tube of embodiment 63 showing the flow tube at its peak deflection in the Y direction.
Figure 58:
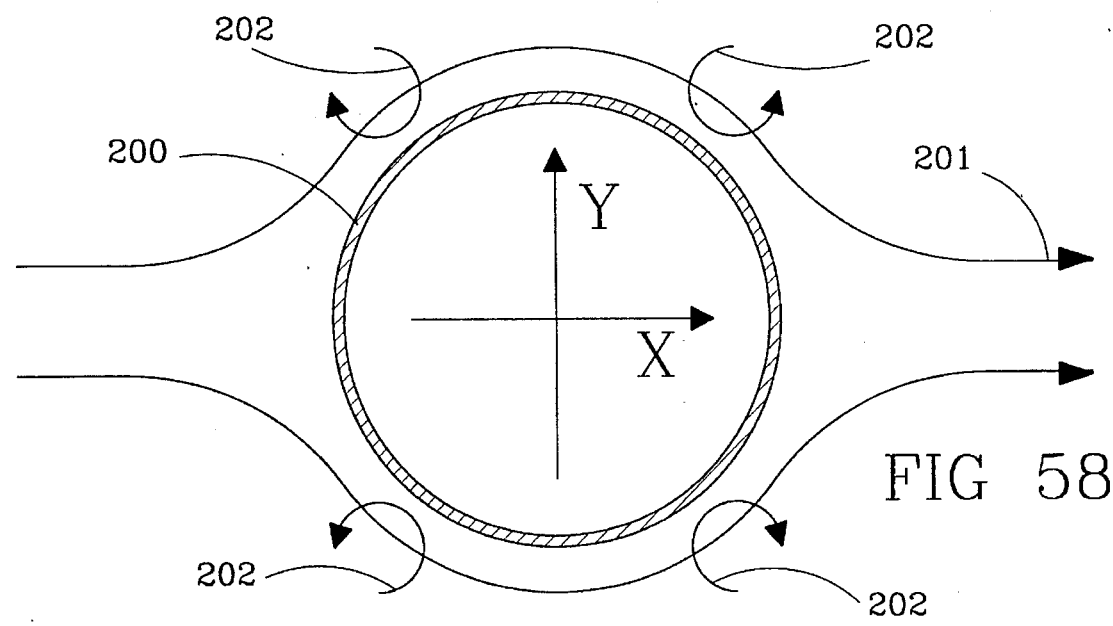
FIG. 58 is a cross sectional view of a flow tube of embodiment 63 showing the flow tube as it passes through its normally undeflected position
Figure 59:
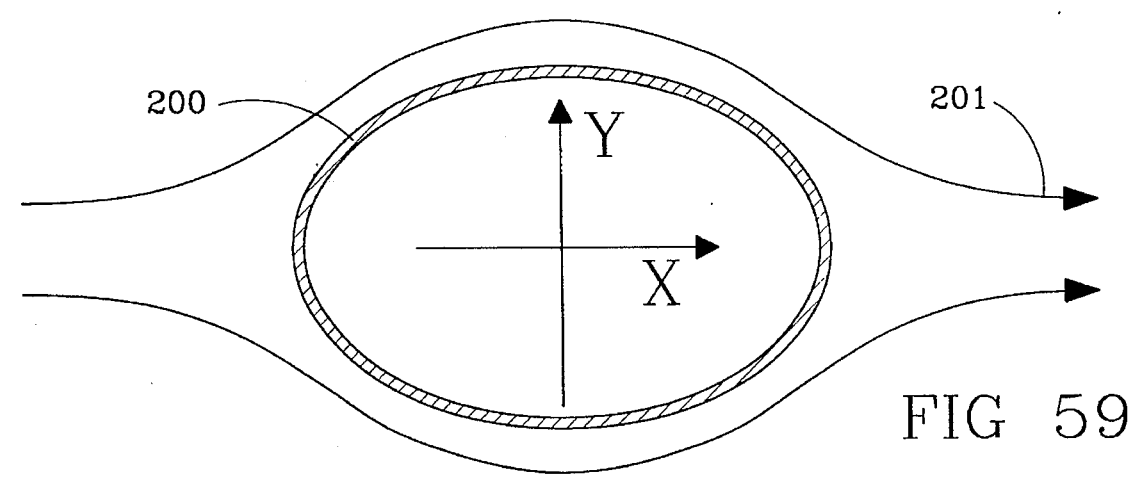
FIG. 59 is a cross sectional view of a flow tube of embodiment 63 showing the flow tube at its peak deflection in the X direction.
Figure 60:
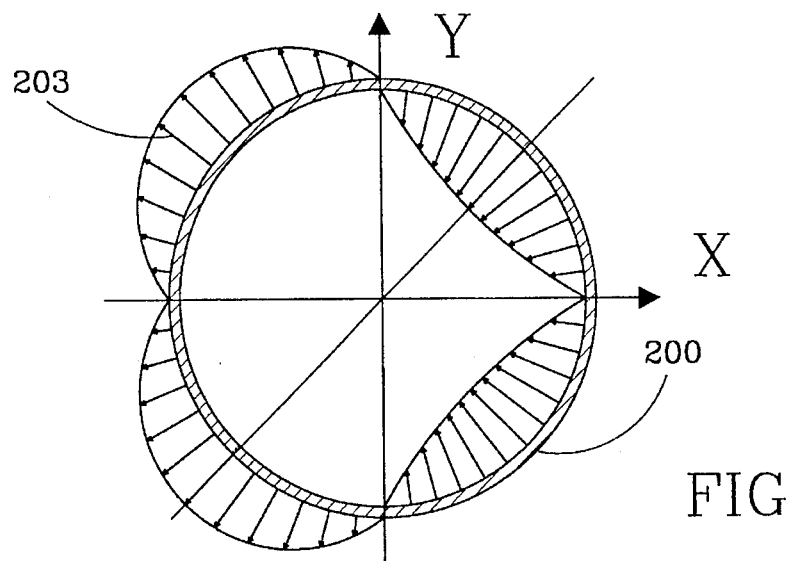
FIG. 60 is a cross sectional view of a flow tube of embodiment 63 showing the distribution of Coriolis forces around the outside of the flow tube.

As an alternate to the embodiment of FIGS. 56 or 71, a similar configuration can be used whereby the fluid flows transversely around the outside of a vibrating surface or tube such as in FIGS. 57 through 59. In these FIGS. tube 200 is vibrated in at least one radial mode of vibration causing deformation into an elliptical cross sectional shape, although any radial mode could be used. In FIGS. 57 through 59, the alignment of the vibratory pattern is shown to be along the X and Y axes and therefore aligned with the direction of the transverse fluid flow 201, however, other alignments of the vibratory pattern with flowing fluid 201 can also be used. FIG. 57 shows tube 200 when it has reached its peak deflection in the Y direction. FIG. 58 shows tube 200 passing through its circular shape after being deflected as in FIG. 57, and FIG. 59 shows tube 200 when it has reached its peak deflecting in the X direction. Fluid flow 201 flowing transverse to the axis of tube 200 changes its flow direction slightly as it conforms to the vibratory motion of tube 200. One result of this change in direction is a rotation 202 of fluid flow 201, which is most pronounced when tube 200 is passing through its circular shape (FIG. 58) thus having the maximum tube wall velocity and causing the maximum fluid rotational velocity. As described for earlier embodiments, the combination of fluid flow 201 and angular rotation 202 of the fluid flow 201, results in a Coriolis force distribution around the outside of tube 200. FIG. 60 shows a resultant Coriolis force distribution 203 that could result from this combination of fluid flow and angular rotation. During the first half of a vibration cycle of tube 200, Coriolis force distribution 203, bearing against tube 200 would in turn cause a small deflection of tube 200 similar to that shown in FIG. 61, where the axis of the deflected shape is displaced by some angle 234 from the axis of the forced vibration. During the second half of a vibration cycle of tube 200, the angular velocities 202 would reverse causing the sign of the Coriolis force distribution 203 to also reverse, in turn causing the deformation of tube 200 to be similar to that shown in FIG. 62. The magnitude of the resultant deflections shown in FIGS. 61 and 62 will therefore be proportional to the magnitude of the mass flow rate of fluid flow 201.

Figure 63:
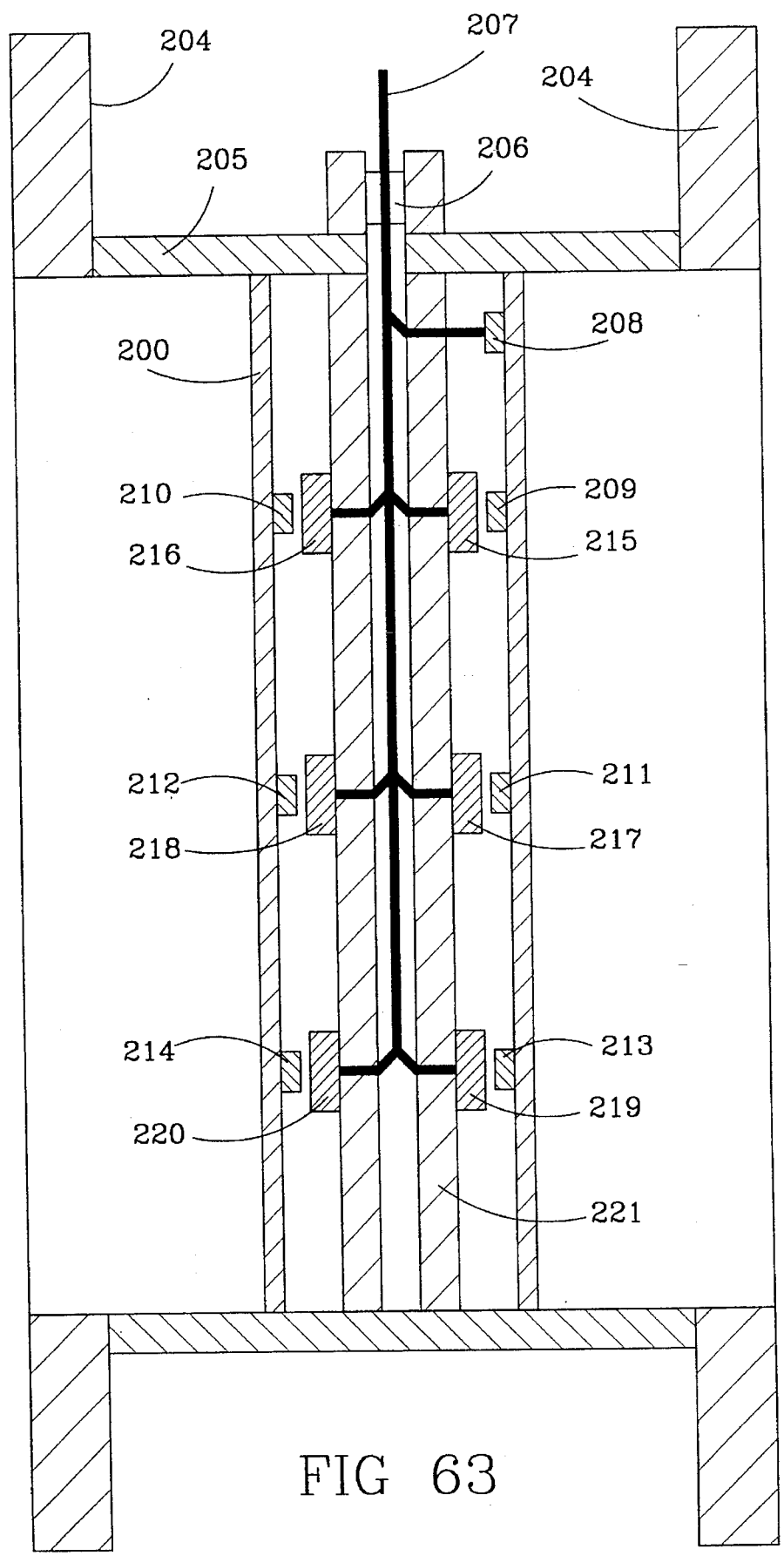
FIG. 63 is a cross sectional view of an alternate embodiment of the device.
Figure 64:
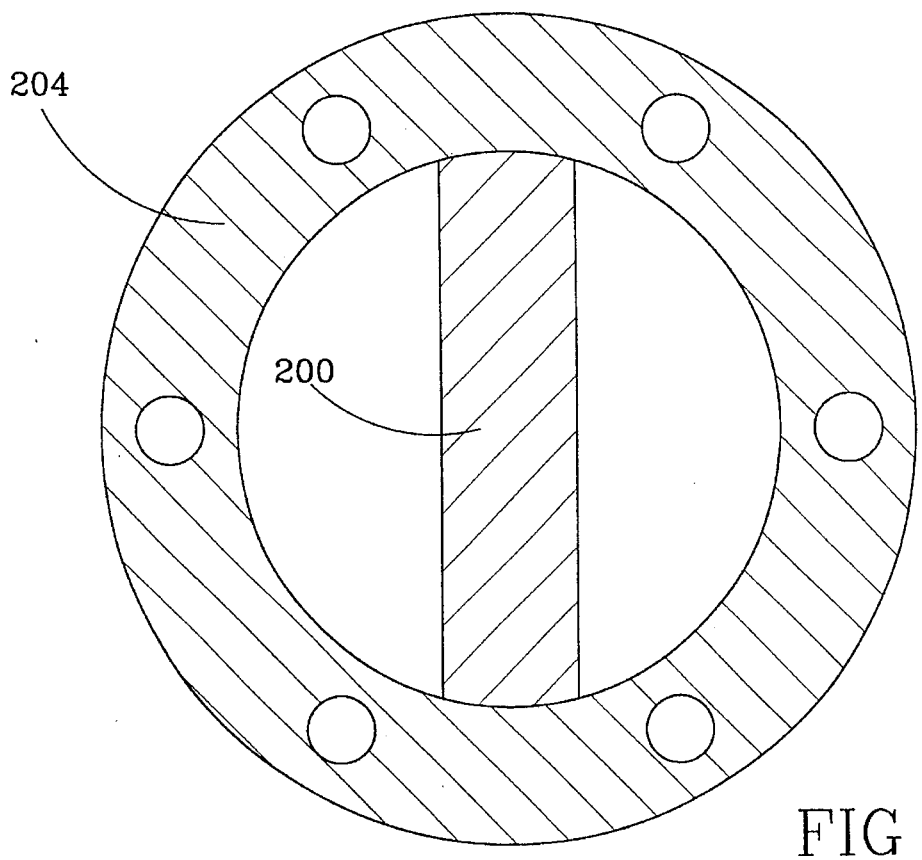
FIG. 64 is an axial view of the embodiment of FIG. 63.
Figure 65:
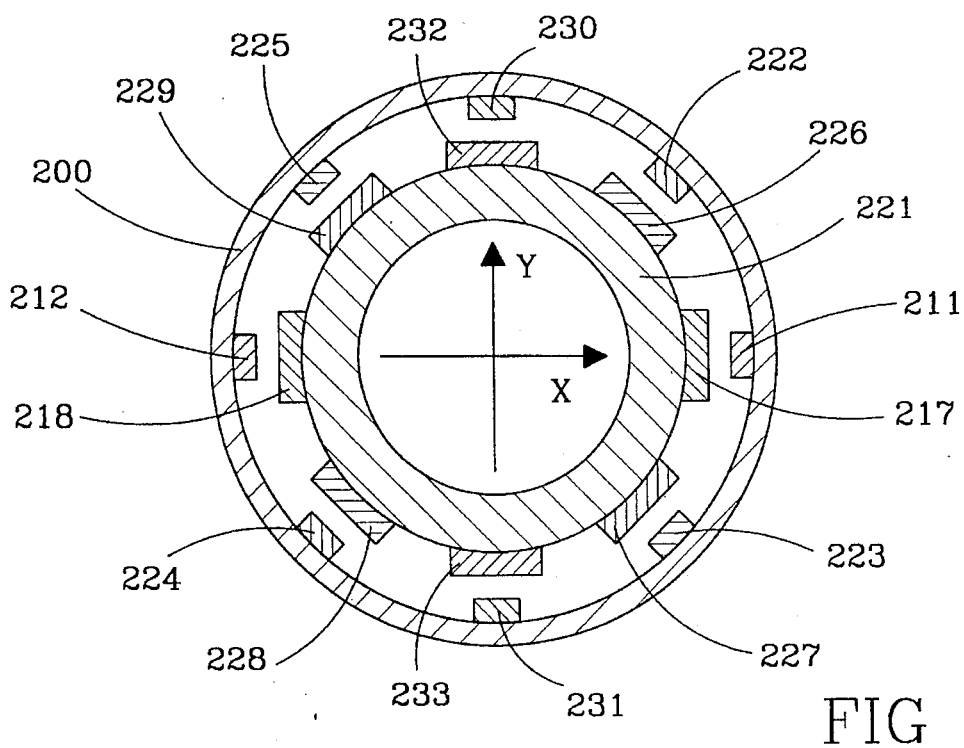
FIG. 65 is a cross sectional view of the embodiment of FIG. 63.

In order to utilize this transverse flow arrangement, an embodiment similar to that shown in FIG. 56 could be used as an insertion device. FIG. 63 shows another transverse flow embodiment in which flow tube 200 is mounted across the diameter of pipe 205, which in turn is mounted between pipe flanges 204, thereby forming a short "Spool Piece", which can easily be mounted in any pipe line. FIG. 64 shows an axial view (down the axis of pipe 205) of the embodiment of FIG. 63 showing flange 204 and the transverse mounted flow tube 200. FIG. 65 is a cross sectional view of flow tube 200 of the embodiments of FIGS. 63 and 64, showing the arrangement of motion drivers and sensors inside flow tube 200. A detailed explanation of the embodiment of FIG. 63 is hereinafter described.

FIG. 63 shows pipe 205 mounted in association with pipe flanges 204 thereby forming a simple spool piece which can easily be mounted in a pipe line. Pipe 205 and flanges 204 are made of steel, stainless steel, alloy steel or any material suitable for the conveyance of fluids. Feed through 206 mounted on pipe 205 allows the conveyance of signal carrier 207 through the wall of pipe 205 into the measuring portion of the device while maintaining a pressure tight seal between the inside of the measuring device and the outer environment. Flow tube 200 is transverse mounted across the diameter of pipe 205, and is preferably made of stainless steel although it could be made of any of the materials previously described for other embodiments. Mounted on the inside of flow tube 200 are motion driving magnets 209 through 214. These motion driving magnets are preferably made of samarium cobalt and are mounted to flow tube 200 by means of adhesive bonding, brazing, or mechanical attachment. Mounted co-axially within flow tube 200 is mounting bracket 221 which is used for the mounting of motion driving and sensing coils. FIG. 63 shows motion driving coils 215 through 220 mounted on bracket 221 and arranged in association with driving magnets 209 through 214, respectively. Driving coils 215 through 220 are electrically connected to an electronic circuit, similar to that of FIG. 26, via signal carrier 207. Temperature sensor 208 is also mounted in association with flow tube 200 and is electrically connected to an electronic circuit, similar to that of FIG. 26, via signal carrier 207, and is used to monitor the temperature of flow tube 200. The operation of the embodiment of FIG. 63 will hereinafter be described.

Excitation signals from electronics (such as in FIG. 26) are conveyed to motion driving coils 215 through 220. These signals therefore cause alternating forces upon motion driving magnets 209 through 214. These forces in turn cause flow tube 200 to vibrate in at least one and preferably two radial modes of vibration. The preferred primary radial mode of vibration is the two lobed elliptical mode similar to that shown in FIGS. 57 through 59, with no reversals in cross sectional shape (no nodes) along the length of tube 200. The preferred secondary radial mode of vibration is the four lobed mode of FIG. 13, again with no reversals (no nodes) along the length of tube 200.

The arrangement and the number of driving magnets and coils, and the phasing of the excitation signals to these coils can be designed to enhance the desired radial modes of vibration while suppressing the excitation of unwanted vibrations. For example, as a minimum, only one motion driving magnet and coil pair (such as 211 and 217, respectively) is necessary to cause the requisite radial vibration. However by using another diametrically opposed motion driving magnet coil pair (212 and 218, respectively), a better balanced situation is achieved and only alternating opposing forces are applied to tube 200 thereby eliminating the excitation of any bending modes of vibration. In addition, more motion driving magnet coil pairs (209 with 215, 210 with 216, 213 with 219, and 214 with 220) are used in FIG. 63 to distribute the driving force along the length of tube 200. Further, additional motion driving magnet coil pairs (230 with 232, and 231 with 233, of FIG. 65), radially displaced around the circumference of tube 200 can also be used.

The number and placement of motion driving magnets and coils around the circumference and along the length of tube 200 is determined by the desired radial modes to be excited, and the desired distribution of driving force along tube 200. For example, if a radial mode were chosen for the primary driven mode in which the elliptical cross sectional shape reverses once (one node) along the length of the tube (similar to that shown in FIG. 9), then the excitation of magnet coil pairs 209 with 215, and 210 with 216, would be excited in a 180° phase relationship with magnet coil pairs 213 with 219, and 214 with 220, while pairs 211 with 217 and 212 with 218 would not be needed, thereby causing one end of tube 200 to be deformed in the Y direction (as in FIG. 57) while the other end of tube 200 is deformed in the X direction (as in FIG. 59).

Using the preferred two lobed elliptical mode (with no reversals), as the primary mode and the 4 lobed mode (with no reversals) as the secondary mode, the combination of radial vibration and fluid flow causes an oscillating Coriolis force distribution similar to that shown in FIG. 60. The oscillating Coriolis force distribution in turn causes tube 200 to radially deform into shapes similar to those shown in FIGS. 61 and 62, as tube 200 passes through its normally (no flow) circular cross sectional shape as in FIG. 58. FIG. 65 shows an array of motion sensing magnets 222 through 225 and their respective motion sensing coils 226 through 229. These motion sensing magnets and coils are radially arranged and displaced from the motion driving magnets and coils, by an angle similar to angle 234 of FIGS. 61 and 62, so as to detect the maximum amount of resultant flow induced deflection of tube 200.

Figure 61:
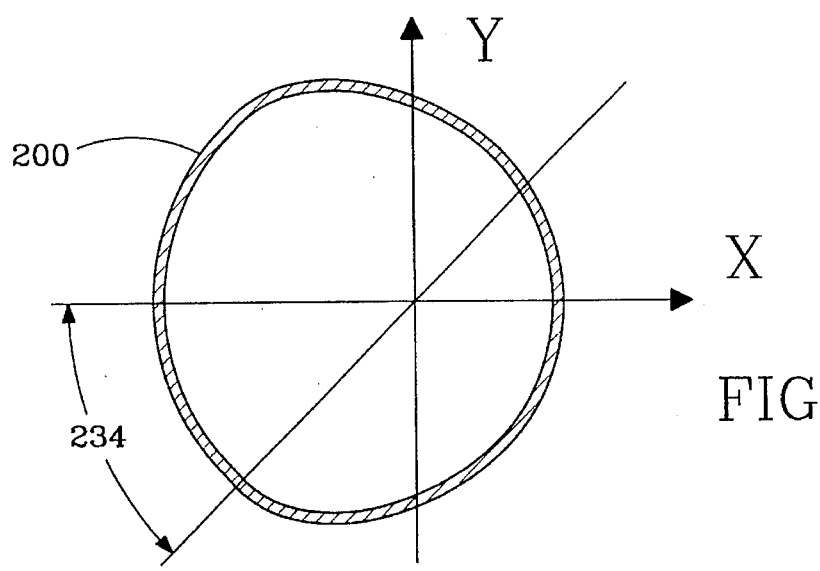
FIG. 61 is a cross sectional view of a flow tube of embodiment 63 showing the deflection that would result from the distribution of Coriolis forces shown in FIG. 60.
Figure 62:
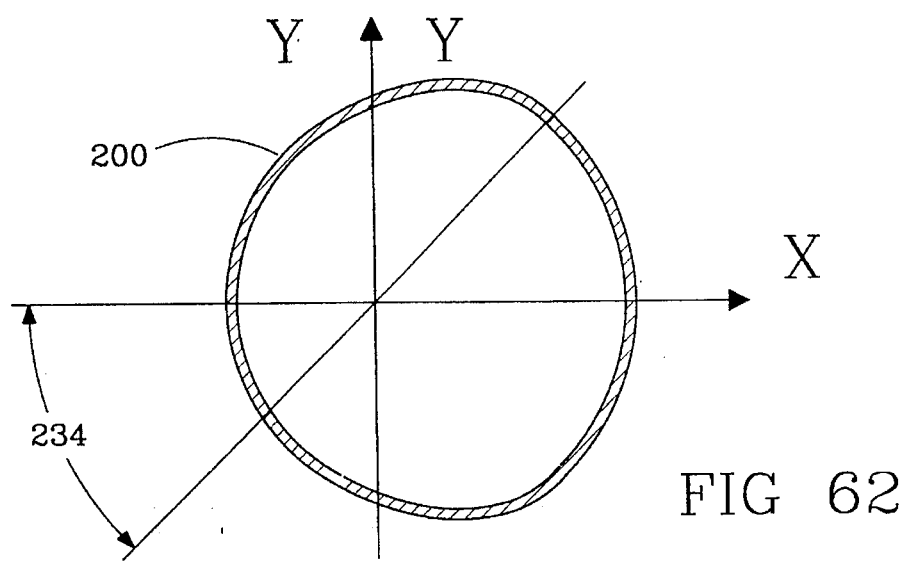
FIG. 62 is a cross sectional view of a flow tube of embodiment 63 showing the deflection that would result from the distribution of Coriolis forces shown in FIG. 60.

With no flow passing over the outside of tube 200, no Coriolis force distribution will result and tube 200 will simply vibrate in its primary mode as shown in FIGS. 57 through 59, and also vibrate in its secondary mode as shown in FIG. 13. As fluid flow 201 increases around the outside of tube 200, and the resultant Coriolis force distribution 203 causes tube 200 to deflect as shown in FIGS. 61 and 62, motion sensing coils 226 through 229 will detect an increasing change in the amplitude of vibration at their locations proportional to flow rate. If angle 234 is chosen to correspond to a translational radial node of tube 200 for the driven vibration (approximately 45°), then the motion signal generated in motion sensing coils 226 through 229 will be primarily proportional to flow rate 201, and will be primarily in phase with the velocity of the Coriolis deflection, which is 90° phase displaced from the velocity of the forced vibration. In this arrangement the phase of the signals produced at the motion sensing coils 226 through 229 will be substantially invariant with flow rate except that they will invert (180° phase change) for flow going in the opposite direction, thereby allowing for both the detection of flow direction, as well as flow rate.

As an alternate to locating the motion sensing magnets and coils at an angle 234 which corresponds to a radial translational node, so that only Coriolis induced deflection signals are excited in the motion sensing coils, an angle 234 could be chosen which does not correspond to a radial translational node. If this is done, the signals excited in motion sensing coils 226 through 229 will then be a combination of the driven motion and the Coriolis induced motion. Since these two motions are phase displaced from each other by substantially 90°, the resultant combination of motions and thus the resultant signals in motion sensing coils 226 through 229 will have a change in both amplitude and phase components which are proportional to flow rate. To determine the flow rate from these combined signals, either a change in amplitude or a change in phase measuring technique could be used as previously described for earlier embodiments. For example, signals in motion sensing coils 229 and 227 would be phase or time displaced from the signals in motion sensing coils 226 and 228. Therefore by electrically connecting coils 226 with 228 and coils 227 with 229, two signals can be attained which will be phase or time displaced from each other by an amount which is proportional to mass flow rate. Alternately these combined signals can be evaluated for their change in amplitude as referenced to the driven amplitude. The change in amplitude as-referenced to the driven amplitude will therefore be functionally related to the flow rate of the process fluid.

As described for earlier embodiments, the pressure and density of the process fluid can then also be determined by evaluating the relationship between the primary frequency and the secondary frequency. In addition the temperature of the fluid will be detected by temperature sensor 208. The signal from temperature sensor 208 will be conveyed back to the electronics via signal carrier 207, whereby the temperature signal can then be used for any requisite compensation or for an output for customer use. And as previously described, the viscosity of the process fluid can then also be determined by evaluating the power necessary to cause the driven vibration. In addition, as previously described for other embodiments, the power required to maintain the vibration of tube 200 is a function of the viscosity of flowing fluid 201. Therefore by measuring this power, a signal can be created proportional to fluid viscosity which can be used by the customer.

A fundamental difference between the use of radial modes and bending modes of vibration for causing Coriolis induced deflections of flow tubes with internal fluid flow, is that bending modes tend to impart a rotational velocity of the entire fluid stream which (except for compressibility effects) is fairly constant at any point of a cross section of the flow tube, while the rotational velocity caused by radial modes can vary throughout the cross section of the flow tube.

Figure 66:
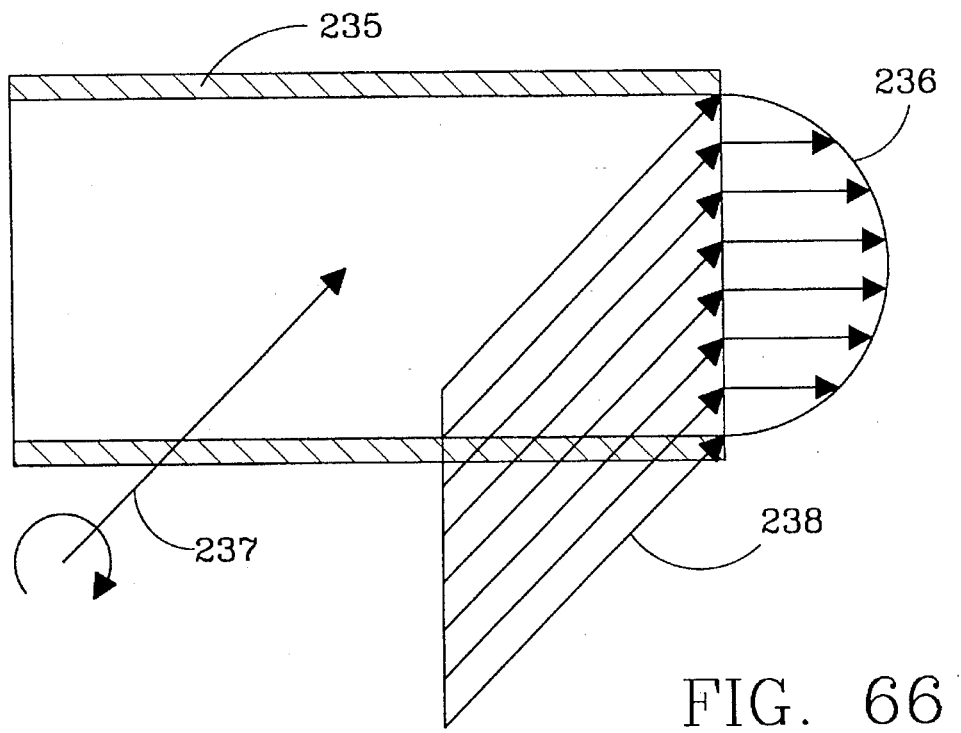
FIG. 66 is a drawing of the velocity profile and rotational velocity distribution for a flow tube operating in a bending mode of vibration.

FIG. 66 shows a section of a bending mode flow tube 235 in which fluid is flowing with a velocity profile 236 as shown. Since the entire flow tube is rotating 237 due to a bending mode, the rotational velocity distribution 238 at any point through the cross section of tube 235 will be nearly constant.

Figure 67:
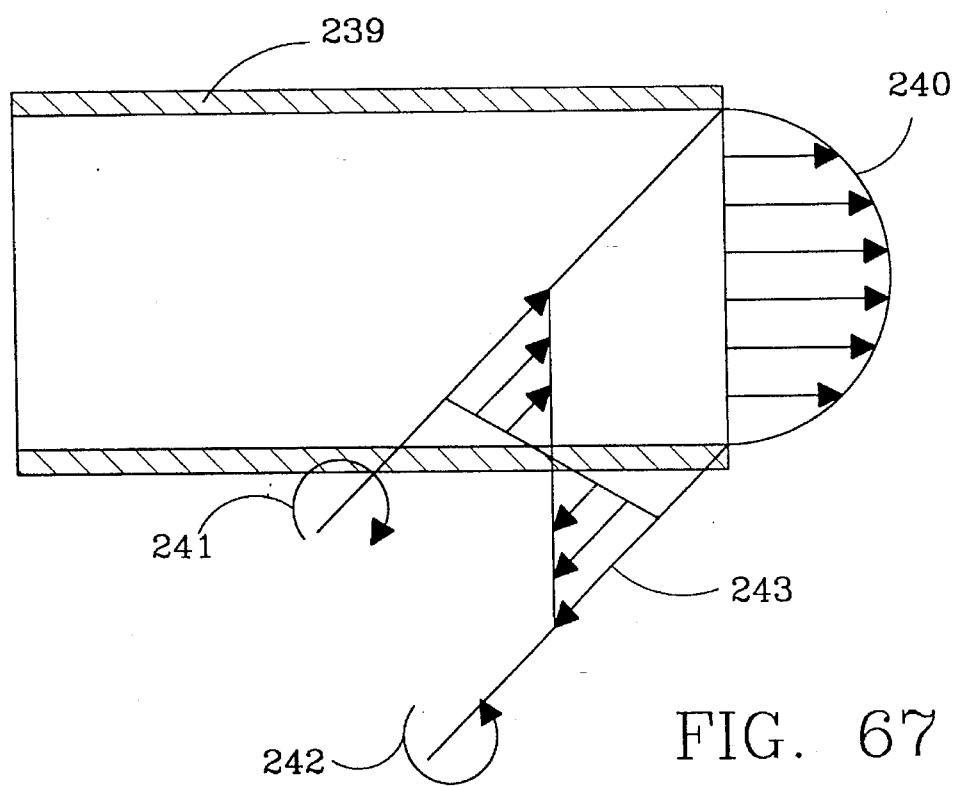
FIG. 67 is a drawing of the velocity profile and rotational velocity distribution for a flow tube operating in a radial mode of vibration.

By contrast, FIG. 67 shows a section of a radial mode flow tube 239 in which fluid is flowing with a velocity profile 240 as shown. Since tube 239 is being vibrated in a radial mode (such as shown in FIGS. 2 through 4), the top surface of tube 239 will rotate 241 in the opposite sense as that of the bottom surface rotation 242, thereby causing a varying rotational velocity distribution 243, which varies through the cross section of tube 239.

Since the Coriolis force contribution of each small unit of fluid is a function of its mass times its velocity 240 times its rotational velocity 243, and since these parameters can vary as a function of position within the flow tube, radial mode flow meters can have a dependency on the velocity profile 240 of the flowing fluid. In many cases, especially in gasses and in low viscosity fluids, the velocity profile will be nearly constant and can therefore be neglected or compensated for by using a simple mathematical relationship with the fluids temperature, flow rate, viscosity, etc. In higher viscosity fluids, or where upstream disturbances have caused an irregular velocity profile, other methods for determining and/or modifying the velocity profile of the fluid and thereby allowing for the compensation of any errors caused by velocity profile are hereinafter described.

As was earlier described for other embodiments, the flow rate, pressure, and density of a flowing fluid can be determined by the use of two simultaneous radial modes of vibration on a flow tube. It has also been stated that either of the two modes of vibration can be used to measure flow rate since either mode of vibration in combination with mass flow rate, will cause Coriolis induced deflections of the tube wall, which can be measured. A unique consequence of using two radial modes of vibration is that the resultant rotational velocity distribution (243 of FIG. 67) will be different for different radial modes of vibration, therefore giving rise to a unique method whereby the effects of velocity profile changes can be determined and compensated for.

Figure 68:
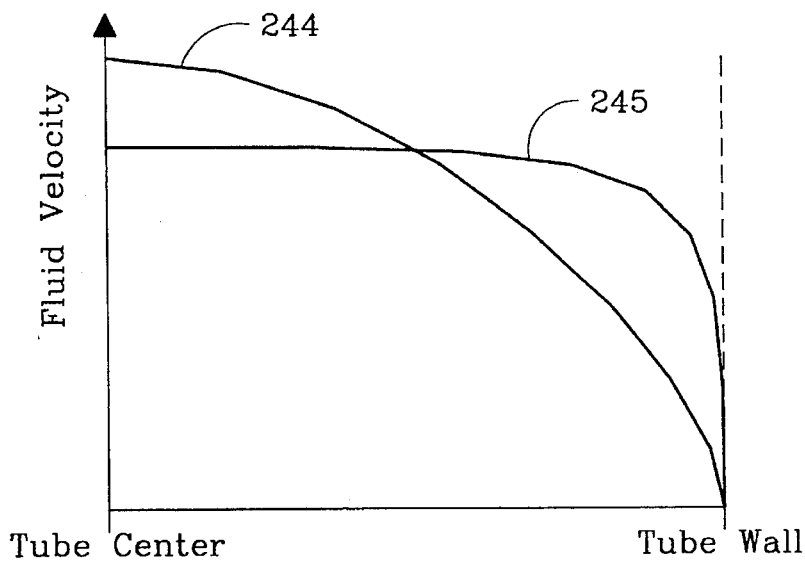
FIG. 68 is a drawing of two possible velocity profiles of fluid flowing in a tube.
Figure 69:
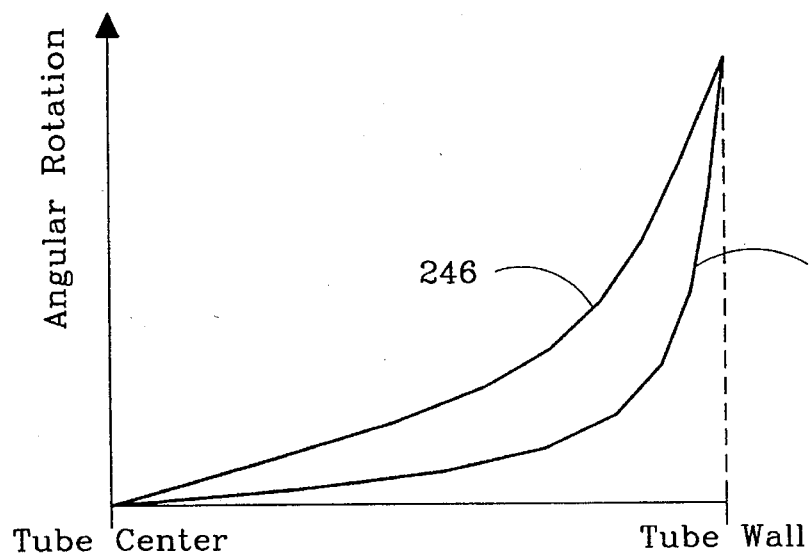
FIG. 69 is a drawing of two possible angular rotation distributions of fluid flowing in a tube, caused by two different radial modes of vibration.

FIG. 68 is a plot of two typical flow velocity profiles 244 and 245 which represent parabolic and "plug" flow, respectively. The area under velocity profiles 244 and 245 are scaled to be the same therefore representing the same mass flow rates. FIG. 69 is a plot of the rotational velocity distributions 246 and 247, which could be caused by the primary radial mode and the secondary radial mode, respectively. In this example, rotational velocity distribution 246 is a second order curve while 247 is a third order curve, and the precise curves for any given design will depend on, among other things, the geometry and on the chosen modes of primary and secondary vibration.

Figure 70:
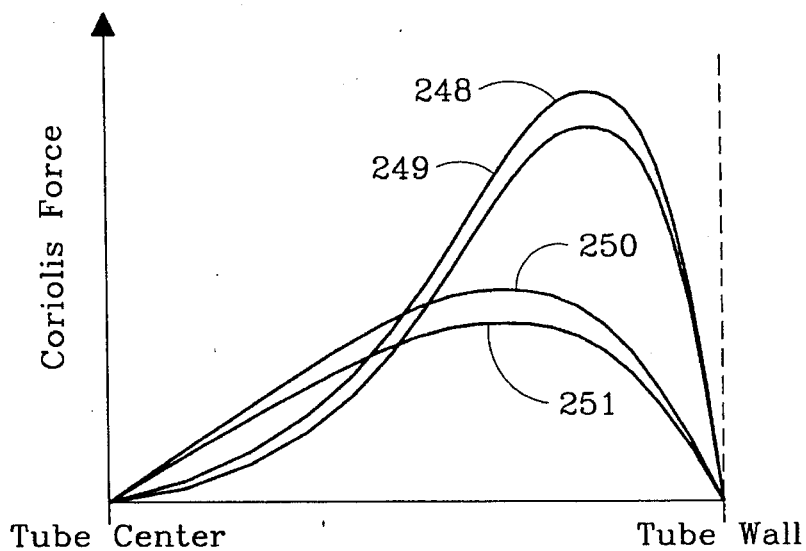
FIG. 70 is a drawing of four different Coriolis force distributions that could result from the combination of velocity profiles and angular rotations shown in FIGS. 68 and 69.

The Coriolis force contribution of any part of the fluid is therefore the product of the mass times the flow velocity times the rotational velocity. FIG. 70 shows four plots of resultant Coriolis force distributions. Coriolis force distributions 248 and 249 would result from parabolic velocity profile 245 times rotational velocity distributions 246 and 247, respectively, while Coriolis force distributions 250 and 251 would result from velocity profile 244 times rotational velocity distributions 246 and 247, respectively. Since the mass flow rates represented by velocity profiles 244 and 245 are the same, the final resultant flow measurement signals need to be the same.

The total Coriolis force for velocity profile 244 would be represented by the area under curves 250 (for the primary mode) and 251 (for the secondary mode), and the total Coriolis force for velocity profile 245 would be represented by the area under curves 248 (for the primary mode) and 249 (for the secondary mode). Visual inspection of FIG. 70 shows that the area under each curve is different and will therefor produce different amounts of tube wall deflection with different flow velocity profiles even though they represent the same mass flow rates.

By measuring the flow rate independently with each of the two driven modes of vibration, a compensation signal can be created, functionally related to the two independent flow results, and can be used to eliminate errors in either flow signal caused by changing velocity distribution. For this example the ratio of the resultant flow signals produced by the primary and the secondary modes, raised to the third power, is a-number which can then be multiplied by either one of the two flow signals to produce a result which is nearly constant for constant mass flow rates during large variations in velocity profile.

The precise mathematical compensation necessary will depend on, among other things, the design of the meter and the chosen modes of primary and secondary vibration. Therefore, many different mathematical relations can be created from the two flow signals and used to compensate the final result for errors caused by changing velocity profiles.

For still higher accuracy, three or more modes of vibration could be used, and more complex compensation factors can be created from the basic phase or amplitude measurement from each mode of vibration.

Other methods of compensating for the effects of velocity profile include calibrating the device with known flow rates, and determining the characteristic output curve for the device. This characteristic output curve can then be loaded into the memory of a microprocessor (look up table), and then used to compensate or linearize the resultant output signal for any effects caused by velocity profile. Mathematical relations based on Reynolds number, viscosity, temperature, density, etc. can also be used in compensation factors to corrects for any undesired non linear effects.

As a further improvement on the embodiment of FIG. 56, a similar embodiment can be located within a pipe or spool-piece to confine the fluid flow 179 in the annular space between vibrating surface 185 and pipe 252 as shown in FIG. 71. In this arrangement, a spool-piece would be formed by the combination of pipe 252 and flanges 253. One additional benefit of the embodiment of FIG. 71 is that effects due to variations in the velocity profile are greatly reduced. As was just described, the net Coriolis force resulting from flow rate can be influenced by changes in the velocity profile. This sensitivity to velocity profile is exacerbated by the geometry of the angular velocity profile (243 of FIG. 67) since it passes through zero in the middle of the tube. By shifting the geometry of the angular velocity profile (243 of FIG. 67) so that the zero point is moved toward one side or eliminated, any velocity profile effect will be greatly reduced or eliminated. Several methods of modifying the angular velocity gradient and thereby reducing or eliminating velocity profile effect will now be described.

Figure 72:
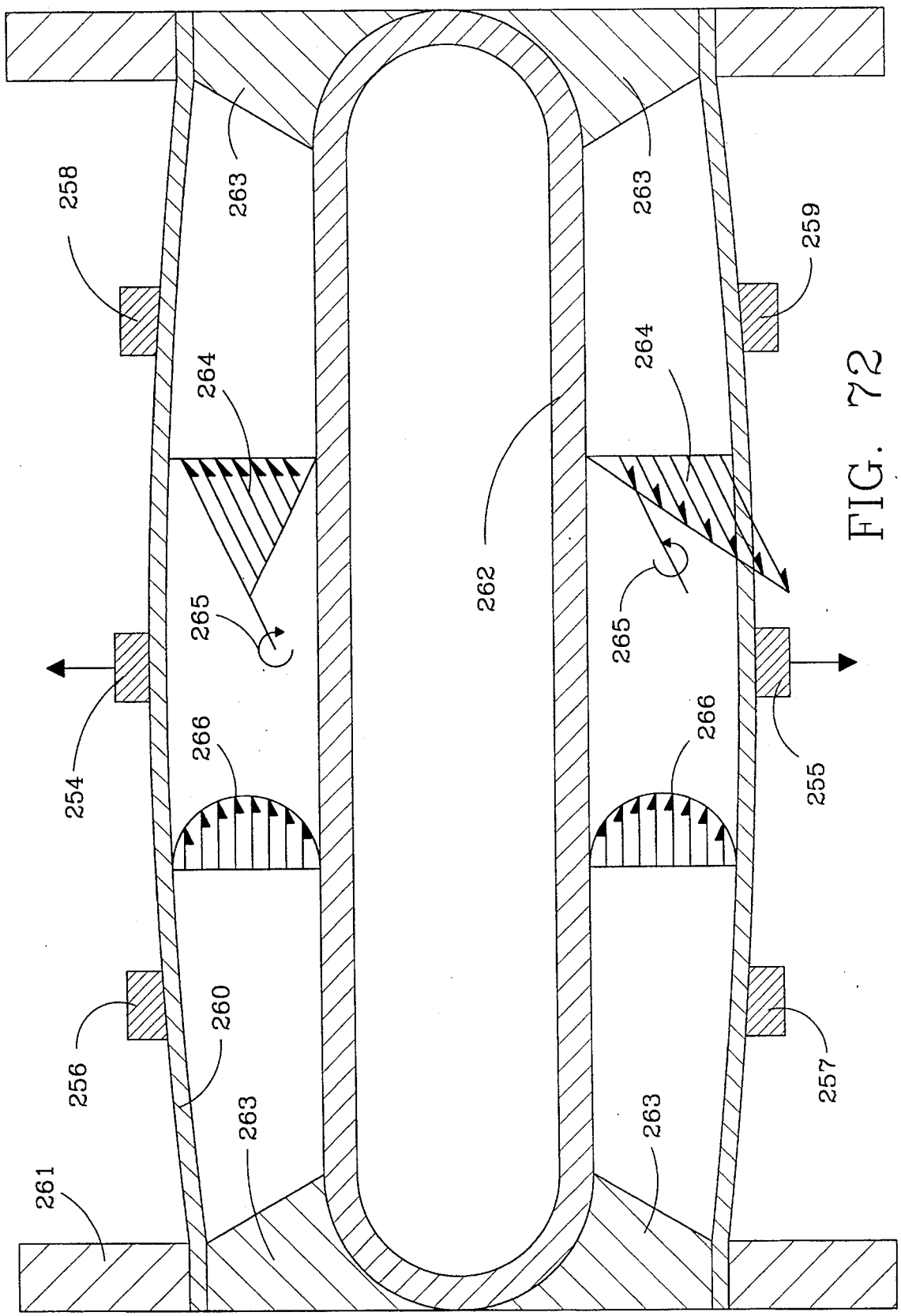
FIG. 72 is the embodiment of FIG. 1 including a stationary flow conditioner.

FIG. 72 is a drawing of an embodiment utilizing a flow conduit similar to that of several previously described embodiments, with the addition of a flow conditioner 262 in the flow stream to change the shape of the angular velocity profile 264 from having a zero point in the center of the fluid stream. In this embodiment, flow conditioner 262 is a stainless steel tube in the shape of a cylinder with rounded ends, suspended in the center of the vibrating flow tube 260 by supports 263 which are thin blades designed to rigidly hold flow conditioner 262 without disturbing the fluid flow 266. Flow tube 260 is instrumented with motion driver/sensors 254 through 259, and is vibrated in at least one and preferably two radial mode of vibration as previously described for other embodiments to both measure the flow rate and to determine the pressure and density of the flowing fluid. FIG. 72 shows the vibration of the tube 260 as the top and bottom surfaces of tube 260 are moving away from each other. At this time the flowing fluid 266 conforms to the deforming shape of tube 260 and thereby is caused to angularity rotate 265 about an axis perpendicular to the flow direction. The magnitude of angular rotation 265 will be a maximum at the moving surface of tube 260 and zero at the surface of flow conditioner 262 thereby describing an angular velocity gradient 264. Since this angular velocity gradient 264 does not pass through a zero value in the center of the tube (as did the gradient 243 of FIG. 67), fluid velocity profile 266 can experience large changes in shape (especially symmetrical changes) without significantly altering the resultant Coriolis forces thereby greatly improving the performance of the device under conditions where fluid velocity profiles are changing.

Figure 73:
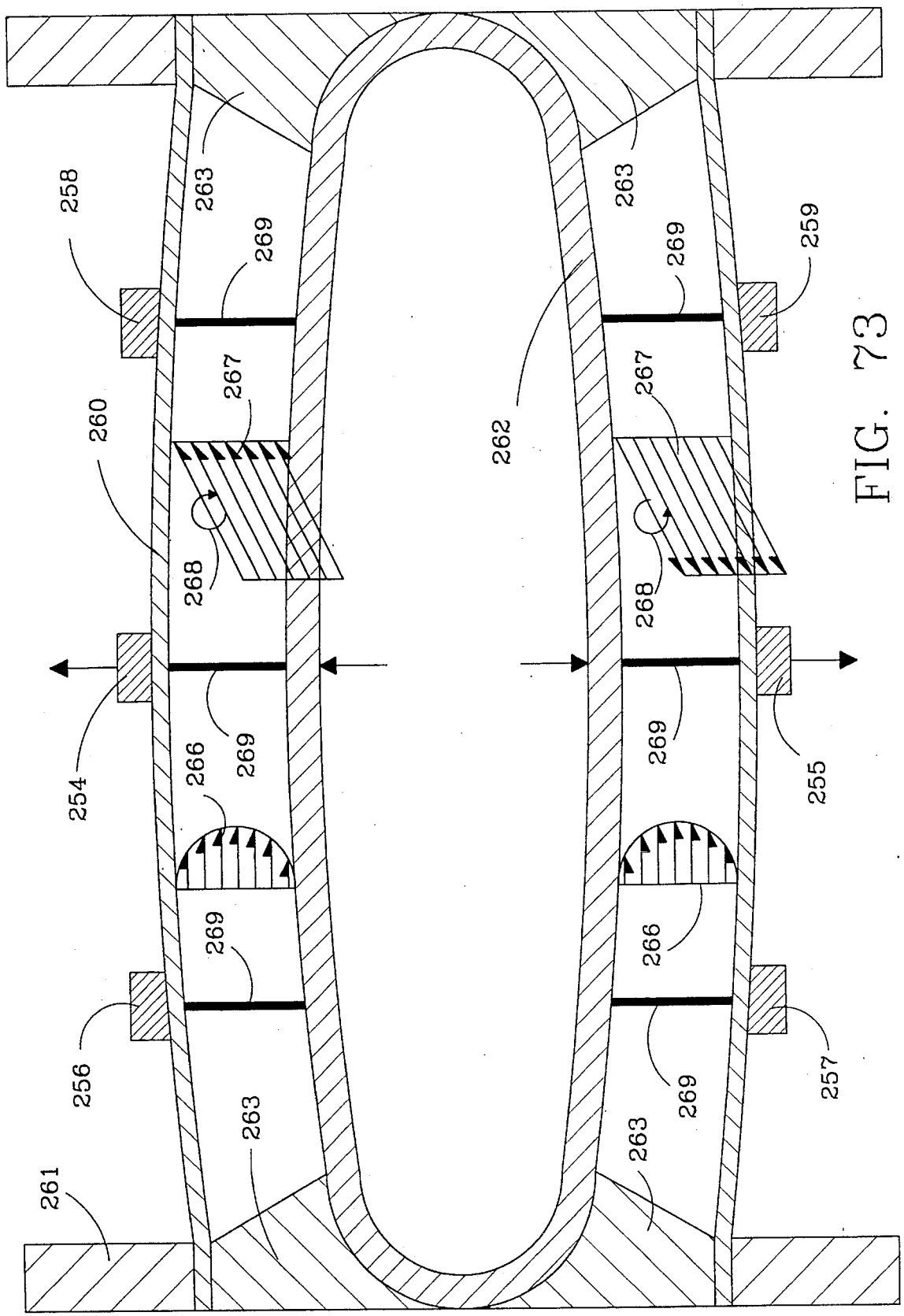
FIG. 73 is the embodiment of FIG. 1 including a dynamic flow conditioner.

FIG. 73 incorporates all the elements of FIG. 72 and additionally provides for vibrational couplings 269 between flow tube 260 and flow conditioner 262. In addition, flow conditioner 262 is designed to be flexible so that the vibration of the flow tube 260 is transmitted to flow conditioner 262 so that its motion is similar to that of flow tube 260. The advantage of this arrangement is that with flow conditioner 262 vibrating in a similar fashion to that of flow tube 260, the angular velocity profile 267 of the flowing fluid 266 will be substantially constant thereby eliminating any velocity profile effect completely. In this embodiment, vibrational coupling 269 can be mechanical connections arranged to transmit the vibration of the flow tube 260 into flow conditioner 262. Other means for coupling the vibration include metal strips, wires, magnetic fields, and the coupling afforded by the flowing fluid 266. With fluids that are highly incompressible such as liquids, the fluid itself would provide adequate vibrational coupling.

Figure 74:
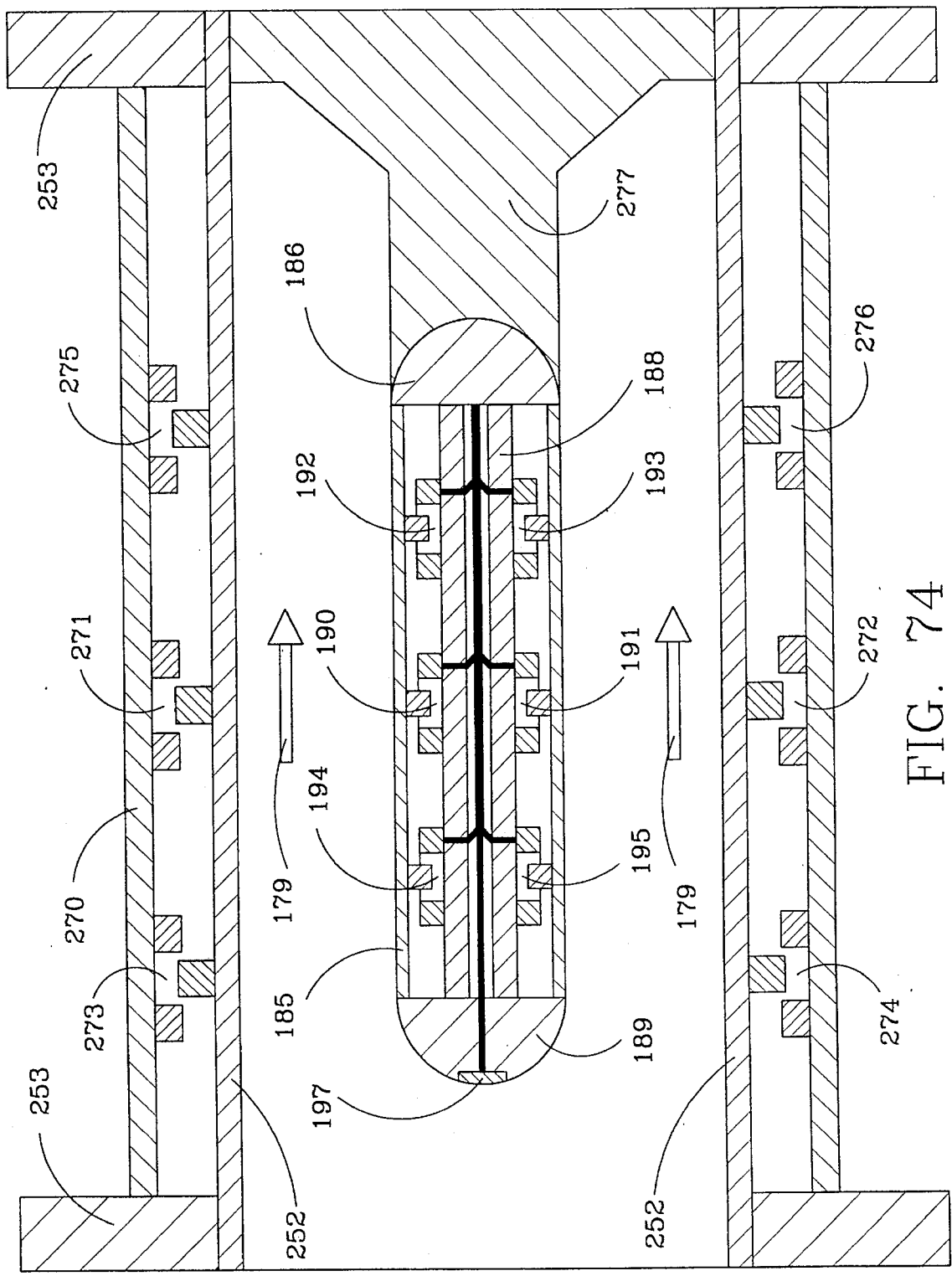
FIG. 74 is the embodiment of FIG. 71 including a pressure tight case and an active outer pipe.
Figure 75:
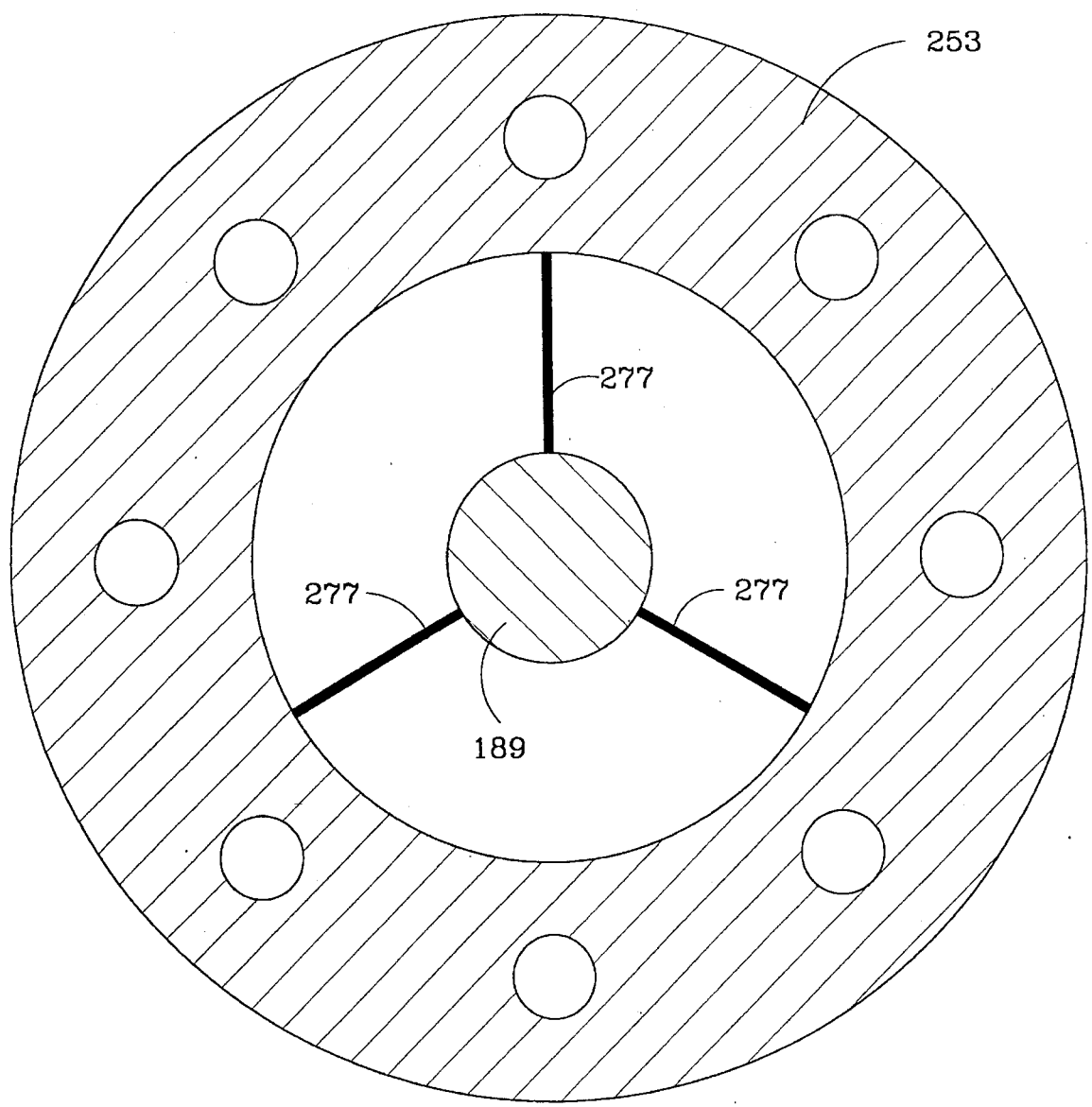
FIG. 75 is an axial view of the embodiment of FIG. 74.

FIG. 74 is similar to that of FIG. 71 with the addition of an outer case 270, and magnet/coil pairs 271 through 276. In this embodiment, surface 185 is excited in at least one radial mode as previously described to measure the flow rate. In addition, tube 252 can also be excited in another mode of vibration to simultaneously measure the flow rate using a mode of vibration at a different frequency than that of surface 185. In this arrangement the frequency of tube 252 would increase with pressure while that of surface 185 would decrease with increasing pressure, and both frequencies would decrease with increasing density, thereby allowing for far more precise pressure and density determinations than with other embodiments. In addition, the dual measurement methods previously described to determine and compensate for velocity profile can easily be implemented using the vibration on surface 185 and that on tube 252. In addition, surface 185 acts as a flow conditioner and thereby reduces velocity profile effect as previously described. Since the diameter of surface 185 can be small in relation to tube 252, the embodiment of FIG. 71 will be much less expensive, and will use less power than one where the outer tube 252 is vibrated. This attribute becomes more important as meter sizes increase since cost and fabrication difficulty increases greatly with pipe size. In addition, as previously described for other embodiments, the power required to maintain the vibration of surface 185 or tube 252 is a function of the viscosity of flowing fluid 179. Therefore by measuring this power, a signal can be created proportional to fluid viscosity which can be used by the customer.

The use of dual vibration modes has previously been described for measuring pressure and density and in the measuring and compensation for velocity profile effects. Both radial and bending modes of vibration have been described for these purposes. In addition to the use these types of vibration modes, torsional modes of vibration can be used for the secondary mode of vibration for the determination of pressure and density using methods previously described. An example of a torsional mode of vibration would be one where the flow conduit or surface rotates about its axis of symmetry. On the embodiment of FIG. 1, a torsional mode of vibration would therefore be described by flow conduit 1 rotating about its longitudinal axis which is the same as that of flowing fluid 28. The advantage of using a torsional mode of vibration as the reference mode to be used in conjunction with the primary radial mode for the determination of pressure and density is that the change in frequency of torsional modes of vibration due to changes in pressure and density is significantly different than that for either radial or bending modes thereby allowing for improved density and pressure determinations.

From the above, it is apparent that the present invention provides an apparatus for measuring attributes of a fluid comprising: (1) a body capable of being inserted into and surrounded by the fluid, (2) means, disposed within the body, for vibrating a surface of the body in a radial mode of vibration, the vibrating surface developing Coriolis forces within the fluid, (3) means, coupled to the surface, for measuring motion of the surface, the motion being a function of Coriolis forces developed in the fluid and (4) means, coupled to the measuring means, for determining an attribute of the fluid as a function of the motion of the surface.

Although the present invention and its advantages have been described in detail, it should be understood that various changes, substitutions and alterations can be made herein without departing from the spirit and scope of the invention as defined by the appended claims.

What is claimed is:

1. An apparatus for measuring an attribute of a fluid in a flow conduit, comprising:
   means for inducing a radial mode vibration in said conduit, said radial mode vibration causing deformation of said conduit;
   means for measuring a change in said deformation; and
   means for modifying an angular velocity gradient of said fluid in said conduit, said modifying means positioned within said conduit.

2. The apparatus as recited in claim 1 further comprising means for coupling a vibration of said conduit to a vibration of said modifying means to thereby cause said modifying means to vibrate in relation to said radial mode vibration.

3. The apparatus as recited in claim 1 wherein said inducing means vibrates said conduit in two radial modes of vibration.

4. The apparatus as recited in claim 1 wherein said measuring means measures a change in phase of said deformation of said conduit.

5. The apparatus as recited in claim 1 wherein said measuring means measures a change in amplitude of said deformation of said conduit.

6. The apparatus as recited in claim 1 wherein said fluid flows along a longitudinal axis of said body.

7. The apparatus as recited in claim 1 wherein said fluid flows along a transverse axis of said body.

8. The apparatus as recited in claim 1 wherein said attribute is a mass flow rate of said fluid.

9. The apparatus as recited in claim 1 wherein said attribute is a pressure of said fluid.

10. The apparatus as recited in claim 1 wherein said attribute is a density of said fluid.

11. The apparatus as recited in claim 1 wherein said attribute is a viscosity of said fluid.

12. The apparatus as recited in claim 1 further comprising:
    an inlet manifold affixed to an end of said conduit; and
    an outlet manifold affixed to an opposite end of said conduit.

13. The apparatus as recited in claim 1 further comprising:

a pressure-tight case, integral with said conduit, defining a pressure-tight chamber about said conduit, said chamber containing a prescribed amount of pressure.

14. The apparatus as recited in claim 13 further comprising:
an inlet manifold affixed to an end of said conduit and defining a first wall of said pressure-tight chamber; and
an outlet manifold affixed to an opposite end of said conduit and defining a second wall of said pressure-tight chamber.

15. The apparatus as recited in claim 14 wherein said pressure-tight case reduces axial stress on said conduit.

16. The apparatus as recited in claim 13 further comprising:
a first temperature sensor in thermal communication with an interior of said pressure tight case; and
a second temperature sensor in thermal communication with an exterior of said conduit.

17. The apparatus as recited in claim 1 further comprising means for isolating vibration associated with said conduit to a selected portion of said conduit.

18. A method of measuring a mass flow rate of a fluid in a flow conduit, comprising the steps of:
inducing a radial mode vibration in said conduit, said radial mode vibration causing deformation of said conduit; and
measuring a change in said deformation by means of a single sensor; and
modifying an angular velocity gradient of said fluid in said conduit with a means for modifying positioned within said conduit.

19. The method as recited in claim 18 further comprising the step of coupling a vibration of said conduit to a vibration of said modifying means to thereby cause said modifying means to vibrate in relation to said radial mode vibration.

20. The method as recited in claim 18 wherein said inducing means vibrates said conduit in two radial modes of vibration.

21. The method as recited in claim 18 wherein the step of measuring comprises the step of detecting motion with a motion detector located along a length of said conduit.

22. The method as recited in claim 21 wherein said change is determined by measuring a change in amplitude of said motion sensed by said motion detector.

23. The method as recited in claim 18 further comprising the step of applying a prescribed amount of pressure between said conduit and a pressure-tight case surrounding said conduit.

24. The method as recited in claim 23 further comprising the steps of:
sensing a first temperature of an interior of said pressure tight case; and
sensing a second temperature of an exterior of said conduit.

* * * * *

UNITED STATES PATENT AND TRADEMARK OFFICE
CERTIFICATE OF CORRECTION

PATENT NO.  : 5,576,500
DATED       : November 19, 1996
INVENTOR(S) : Donald R. Cage, et al.

It is certified that error appears in the above-indentified patent and that said Letters Patent is hereby corrected as shown below:

Col. 12, line 29, insert --6-- after "and."

Col. 17, line 35, "Land" should be --and--.

Col. 17, line 45, "it is" should be --its--.

Col. 23, line 6, "+130" should be --130--.

Signed and Sealed this

First Day of April, 1997

*Attest:*

BRUCE LEHMAN

*Attesting Officer*   *Commissioner of Patents and Trademarks*